US007732466B2

(12) United States Patent
Pfau et al.

(10) Patent No.: US 7,732,466 B2
(45) Date of Patent: *Jun. 8, 2010

(54) SUBSTITUTED THIOPHENE CARBOXAMIDES, PROCESS FOR THEIR PREPARATION AND THEIR USE AS MEDICAMENTS

(75) Inventors: Roland Pfau, Biberach (DE); Henning Priepke, Warthausen (DE); Kai Gerlach, Biberach (DE); Wolfgang Wienen, Biberach (DE); Annette Schuler-Metz, Ulm (DE); Herbert Nar, Ochsenhausen (DE); Sandra Handschuh, Warthausen (DE); Georg Dahmann, Attenweiler (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 163 days.

This patent is subject to a terminal disclaimer.

(21) Appl. No.: 11/125,734

(22) Filed: May 10, 2005

(65) Prior Publication Data

US 2006/0293300 A1 Dec. 28, 2006

(30) Foreign Application Priority Data

May 13, 2004 (EP) .................................. 04011395

(51) Int. Cl.
*A01N 43/36* (2006.01)
*A61K 31/44* (2006.01)
*A01N 43/50* (2006.01)
*C07D 487/04* (2006.01)
*C07D 401/00* (2006.01)

(52) U.S. Cl. ....................... 514/340; 514/397; 514/422; 548/300.4; 548/518; 546/276.4

(58) Field of Classification Search ................. 540/524; 544/146; 548/335.1, 407, 418, 542; 546/15, 546/209, 280.4
See application file for complete search history.

(56) References Cited

U.S. PATENT DOCUMENTS 7,476,663 B2 * 1/2009 Pfau et al. .............. 514/217.03

FOREIGN PATENT DOCUMENTS

WO WO 2004/031145 A2 4/2004
WO WO 2004/046138 A1 6/2004

OTHER PUBLICATIONS

Qiao et al., Bioorg Med Chem Lett. 17, 2007, 4419-4427.*
Orvim et al., http://atvb.ahajournals.org/cgi/content/full/atvbaha;15/12/2188, 17 pages.*
Fressinaud et al., Blood, vol. 80, 1992, 988-994.*
Lifeblood, The Thrombosis Charity fact sheet for Venous Thrombosis.*
Lifeblood, The Thrombosis Charity fact sheet for Arterial Thrombosis.*
http://www.webwire.com/ViewPressRel.asp?ald=41878.*
http://www.medscape.com/ viewarticle/559478.*
Han et al., caplus an 2008:831458.*
International Search Report of International Application No. PCT/EP2005/004976.
Bailey, et al., The British Library—"the world's knowledge", Amides, pp. 257-307.
Choi, et al., "Thrombin-Induced Microglial Activation Produces Degeneration of Nigral Dopaminergic Neurons in Vivo", The Journal of Neuroscience, Jul. 2, 2003—23(13):5877-5886.
Akiyama, et al., "Thrombin accumulation in brains of patients with Alzheimer's disease", Neuroscience Letters, 146 (1992) 152-154.
Mhatre, et al, "Thrombin, a mediator of neurotoxicity and memory impairment", Neurobiology of Aging 25 (2004) 783-793.

* cited by examiner

*Primary Examiner*—Golam M. M. Shameem
*Assistant Examiner*—Sun Jae Y Loewe
(74) *Attorney, Agent, or Firm*—Michael P. Morris; Alan R. Stempel; Edouard G. Lebel

(57) ABSTRACT

The present invention relates to new substituted thiophene-2-carboxylic acid amides of general formula (I)

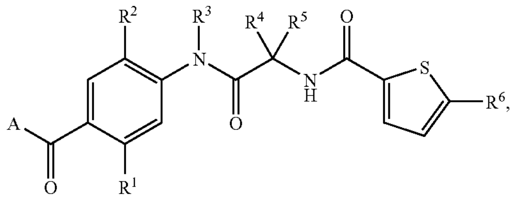

wherein A, and $R^1$ to $R^{8c}$ are defined as in claim 1, the tautomers, the enantiomers, the diastereomers, the mixtures thereof and the salts thereof, particularly the physiologically acceptable salts thereof with inorganic or organic acids or bases, which have valuable properties.

14 Claims, No Drawings

SUBSTITUTED THIOPHENE CARBOXAMIDES, PROCESS FOR THEIR PREPARATION AND THEIR USE AS MEDICAMENTS

The present invention relates to new substituted thiophene-2-carboxylic acid amides of general formula (I)

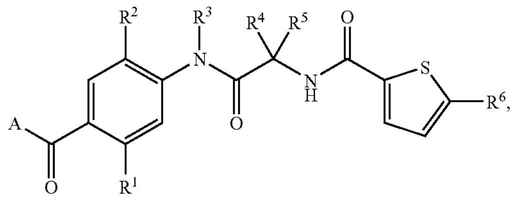

the tautomers, the enantiomers, the diastereomers, the mixtures thereof and the salts thereof, particularly the physiologically acceptable salts thereof with inorganic or organic acids or bases, which have valuable properties.

The compounds of the above general formula I as well as the tautomers, the enantiomers, the diastereomers, the mixtures thereof and the salts thereof, particularly the physiologically acceptable salts thereof with inorganic or organic acids or bases, and their stereoisomers have valuable pharmacological properties, particularly an antithrombotic activity and a factor Xa-inhibiting activity.

The present application thus relates to the new compounds of the above general formula I, the preparation thereof, the pharmaceutical compositions containing the pharmacologically effective compounds, the preparation and use thereof.

A 1st embodiment of the present invention comprises those compounds of general formula I, wherein A denotes a 4- to 7-membered cycloalkyleneimino group, while
- one or two methylene groups of the cycloalkyleneimino moiety may be substituted in each case by one or two $C_{1-3}$-alkyl groups optionally substituted by a hydroxy, $C_{1-3}$-alkoxy, amino, $C_{1-3}$-alkylamino, di-($C_{1-3}$-alkyl)-amino, a 4- to 7-membered cycloalkyleneimino, $C_{1-5}$-alkylcarbonylamino, $C_{1-5}$-alkylsulphonylamino or $C_{1-5}$-alkyloxycarbonylamino groups, or an aminocarbonyl, $C_{1-3}$-alkylaminocarbonyl or di-($C_{1-3}$-alkyl)-aminocarbonyl group and one or two methylene groups of the cycloalkyleneimino moiety not adjacent to the imino group may be substituted by one or two fluorine atoms or a hydroxy, $C_{1-3}$-alkoxy, amino, $C_{1-3}$-alkylamino or di-($C_{1-3}$-alkyl)-amino group and/or
- a methylene group in the 3 position of a 5-membered cycloalkyleneimino group may be replaced by a sulphur atom, or
- a methylene group in the 4 position of a 6- or 7-membered cycloalkyleneimino group may be replaced by an oxygen or sulphur atom, by a carbonyl, sulphinyl, sulphonyl or —$NR^{8c}$— group and additionally a methylene group adjacent to a above-mentioned —$NR^{8c}$— group may be replaced by a carbonyl group, or
- an 5- to 7-membered cycloalkenyleneimino group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{1-6}$-cycloalkylamino-$C_{1-3}$-alkyl, aryl, aryl-$C_{1-3}$-alkyl, heteroaryl, heteroaryl-$C_{1-3}$-alkyl, aminocarbonyl, $C_{1-3}$-alkylaminocarbonyl, di-($C_{1-3}$-alkyl)-aminocarbonyl or 4- to 7-membered cycloalkyleneiminocarbonyl groups, while the double bond is not bound to a nitrogen atom and may be fused to a 5- or 6-membered heteroaryl group, $R^1$ denotes a hydrogen or halogenatom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogenatom or a $C_{1-3}$-alkyl group, $R^3$ denotes a hydrogen atom or a $C_{1-3}$-alkyl group, $R^4$ and $R^5$ in each case independently of one another denote
- a hydrogen atom, a $C_{2-6}$-alkenyl or $C_{2-6}$-alkynyl group,
- a straight-chain or branched $C_{1-6}$-alkyl group,
  - while the hydrogen atoms of the straight-chain or branched $C_{1-6}$-alkyl group may optionally be wholly or partly replaced by fluorine atoms, and may optionally be substituted by a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino or $C_{1-5}$-alkylsulphonylamino group,
- a carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkoxycarbonyl, $C_{4-6}$-cycloalkyleneiminocarbonyl group,
- a phenyl, heteroaryl, phenyl-$C_{1-5}$-alkyl or heteroaryl-$C_{1-5}$-alkyl group,
  - which may optionally be mono- to trisubstituted in the phenyl or heteroaryl moiety by identical or different substituents selected from the group consisting of halogen atoms, $C_{1-5}$-alkyl, di-($C_{1-5}$-alkyl)-amino, hydroxy, $C_{1-5}$-alkyloxy, mono-, di- or trifluoromethoxy, carboxy and $C_{1-5}$-alkyloxycarbonyl groups,
- a 3- to 7-membered cycloalkyl, cycloalkyleneimino, cycloalkyl-$C_{1-5}$-alkyl or cycloalkyleneimino-$C_{1-3}$-alkyl group,
  - wherein in 4- to 7-membered cyclic groups in the cyclic moiety a methylene group may optionally be replaced by an —$N(R^{8c})$— group, an oxygen or sulphur atom or a —S(O) or —$S(O)_2$ group, or
  - wherein in 4- to 7-membered cyclic groups in the cyclic moiety two adjacent methylene groups may together optionally be replaced by a —$C(O)N(R^{8b})$— or —$S(O)_2N(R^{8b})$— group, or
  - wherein in 6- to 7-membered cyclic groups in the cyclic moiety three adjacent methylene groups may optionally be replaced together by a substituted —$OC(O)N(R^{8b})$— or —$N(R^{8b})C(O)N(R^{8b})$— or —$N(R^{8b})S(O)_2N(R^{8b})$— group,
  - with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms selected from among oxygen and nitrogen are separated from one another by precisely one optionally substituted —$CH_2$— group, is excluded, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —$CH_2$— groups by one or two $C_{1-3}$-alkyl groups in each case, or $R^4$ and $R^5$ together with the carbon atom to which they are bound form a $C_{3-8}$-cycloalkyl or $C_{3-8}$-cycloalkenyl group, while one of the methylene groups of a $C_{4-8}$-cycloalkyl group may be replaced by an oxygen or sulphur atom or an —N($R^{8c}$)—, or a carbonyl, sulphinyl or sulphonyl group, and/or two directly adjacent methylene groups of a $C_{4-8}$-cycloalkyl group may be replaced together by a —C(O)N($R^{8b}$)— or —$S(O)_2N(R^{8b})$— group, and/or three directly adjacent methylene groups of a $C_{6-8}$-cycloalkyl group may be replaced together by a —OC(O)N($R^{8b}$)—, —N($R^{8b}$)C(O)N($R^{8b}$)— or —N($R^{8b}$)$S(O)_2$N($R^{8b}$) group, while each of the carbon atoms of a $C_{3-8}$-cycloalkyl group may optionally be substituted independently of one another by in each case one or two identical or different halogen atoms or $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino groups, while each of the carbon atoms of a $C_{3-8}$-cycloalkenyl group may optionally be substituted independently of one another by in each case one or two identical or different $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl group, and each of the carbon atoms of a $C_{4-8}$-cycloalkenyl group which are not bound to another carbon atom by a double bond may optionally be substituted independently of one another by two identical or different fluorine atoms or hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkylsulphonylamino groups, with the proviso that a $C_{3-8}$-cycloalkyl or $C_{3-8}$-cycloalkenyl group of this kind, formed from $R^4$ and $R^5$ together, wherein two heteroatoms in the cyclic group selected from among oxygen and nitrogen are separated from one another by precisely one optionally substituted —$CH_2$— group, and/or wherein one or both methylene groups of the cyclic group which are directly connected to the carbon atom to which the groups $R^4$ and $R^5$ are bound, are replaced by a heteroatom selected from among oxygen, nitrogen and sulphur, and/or wherein a substituent bound to the cyclic group, which is characterised in that a heteroatom selected from among an oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are joined together directly, is excluded, $R^6$ denotes a fluorine, chlorine, bromine or iodine atom, a nitrile group, a $C_{1-3}$-alkyl or a $C_{1-3}$-alkoxy group, while the hydrogen atoms of the $C_{1-3}$-alkyl or $C_{1-3}$-alkoxy group may optionally be wholly or partly replaced by fluorine atoms, $R^{8b}$ in each case independently of one another denotes a hydrogen atom or a $C_{1-5}$-alkyl group, $R^{8c}$ in each case independently of one another denotes a hydrogen atom, a $C_{1-5}$-alkyl, $C_{1-5}$-alkylcarbonyl, $C_{1-5}$-alkyloxycarbonyl or $C_{1-5}$-alkylsulphonyl group, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, or an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a 4- to 7-membered cycloalkyleneimino-$C_{1-3}$-alkyl or phenyl-$C_{1-3}$-alkyl group, or an oxygen or sulphur atom and additionally a nitrogen atom or an imino group optionally substituted by a $C_{1-3}$-alkyl or phenyl-$C_{1-3}$-alkyl group, and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the foregoing definitions which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

Examples of monocyclic heteroaryl groups are the pyridyl, N-oxy-pyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thiophenyl, thiazolyl, isothiazolyl, [1,2,3]thiadiazolyl, [1,2,4]thiadiazolyl or [1,2,5]thiadiazolyl group.

Examples of bicyclic heteroaryl groups are the benzimidazolyl, benzofuranyl, benzo[c]furanyl, benzothiophenyl, benzo[c]thiophenyl, benzothiazolyl, benzo[c]-isothiazolyl, benzo[d]isothiazolyl, benzoxazolyl, benzo[c]isoxazolyl, benzo[d]-isoxazolyl, benzo[1,2,5]oxadiazolyl, benzo[1,2,5]thiadiazolyl, benzo[1,2,3]thia-diazolyl, benzo[d][1,2,3]triazinyl, benzo[1,2,4]triazinyl, benzotriazolyl, cinnolinyl, quinolinyl, N-oxy-quinolinyl, isoquinolinyl, quinazolinyl, N-oxy-quinazolinyl, quinoxalinyl, phthalazinyl, indolyl, isoindolyl or 1-oxa-2,3-diaza-indenyl group.

Examples of the $C_{1-6}$-alkyl groups mentioned hereinbefore in the definitions are the methyl, ethyl, 1-propyl, 2-propyl, n-butyl, sec-butyl, tert-butyl, 1-pentyl, 2-pentyl, 3-pentyl, neo-pentyl, 3-methyl-2-butyl, 1-hexyl, 2-hexyl, 3-hexyl, 3-methyl-2-pentyl, 4-methyl-2-pentyl, 3-methyl-3-pentyl, 2-methyl-3-pentyl, 2,2-dimethyl-3-butyl or 2,3-dimethyl-2-butyl group.

Examples of the $C_{1-5}$-alkyloxy groups mentioned hereinbefore in the definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy or neo-pentyloxy group.

Examples of the $C_{2-6}$-alkenyl groups mentioned hereinbefore in the definitions are the ethenyl, 1-propen-1-yl, 2-propen-1-yl, 1-buten-1-yl, 2-buten-1-yl, 3-buten-1-yl, 1-penten-1-yl, 2-penten-1-yl, 3-penten-1-yl, 4-penten-1-yl, 1-hexen-1-yl, 2-hexen-1-yl, 3-hexen-1-yl, 4-hexen-1-yl, 5-hexen-1-yl, but-1-en-2-yl, but-2-en-2-yl, but-1-en-3-yl, 2-methyl-prop-2-en-1-yl, pent-1-en-2-yl, pent-2-en-2-yl, pent-3-en-2-yl, pent-4-en-2-yl, pent-1-en-3-yl, pent-2-en-3-yl, 2-methyl-but-1-en-1-yl, 2-methyl-but-2-en-1-yl, 2-methyl-but-3-en-1-yl, 2-ethyl-prop-2-en-1-yl, hex-1-en-2-yl, hex-2-en-2-yl, hex-3-en-2-yl, hex-4-en-2-yl, hex-5-en-2-yl, hex-1-en-3-yl, hex-2-en-3-yl, hex-3-en-3-yl, hex-4-en-3-yl, hex-5-en-3-yl, hex-1-en-4-yl, hex-2-en-4-yl, hex-3-en-4-yl, hex-4-en-4-yl, hex-5-en-4-yl, 4-methyl-pent-1-en-3-yl, 3-methyl-pent-1-en-3-yl, 2-methyl-pent-1-en-3-yl, 2,3-dimethyl-but-1-en-3-yl, 3,3-dimethyl-but-1-en-2-yl or 2-ethyl-but-1-en-3-yl group, Examples for the $C_{2-6}$-alkynyl groups mentioned hereinbefore in the definitions are the ethynyl, 1-propynyl, 2-propynyl, 1-butyn-1-yl, 1-butyn-3-yl, 2-butyn-1-yl, 3-butyn-1-yl, 1-pentyn-1-yl, 1-pentyn-3-yl, 1-pentyn-4-yl, 2-pentyn-1-yl, 2-pentyn-3-yl, 3-pentyn-1-yl, 4-pentyn-1-yl, 2-methyl-1-butyn-4-yl, 3-methyl-1-butyn-1-yl, 3-methyl-1-butyn-3-yl, 1-hexyn-1-yl, 2-hexyn-1-yl, 3-hexyn-1-yl, 4-hexyn-1-yl, 5-hexyn-1-yl, 1-hexyn-3-yl, 1-hexyn-4-yl, 1-hexyn-5-yl, 2-hexyn-4-yl, 2-hexyn-5-yl, 3-hexyn-5-yl, 3-methyl-1-pentyn-3-yl, 4-methyl-1-pentyn-3-yl, 3-methyl-1-pentyn-4-yl, 4-methyl-1-pentyn-4-yl, 4-methyl-2-pentyn-4-yl, 4-methyl-2-pentyn-1-yl, 2,2-dimethyl-3-butyn-1-yl or 2-ethyl-3-butyn-1-yl group.

By a group which may be converted in vivo into a carboxy group is meant for example a carboxy group esterified with an alcohol wherein the alcoholic moiety preferably denotes a $C_{1-6}$-alkanol, a phenyl-$C_{1-3}$-alkanol, a $C_{3-9}$-cycloalkanol, a $C_{5-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom starts from a carbon atom which carries a double or triple bond, a $C_{3-8}$-cycloalkyl-$C_{1-3}$-alkanol or an alcohol of formula $$R^9—CO—O—(R^{10}CR^{11})—OH,$$

wherein $R^9$ denotes a $C_{1-8}$-alkyl, $C_{5-7}$-cycloalkyl, phenyl or phenyl-$C_{1-3}$-alkyl group, $R^{10}$ denotes a hydrogen atom, a $C_{1-3}$-alkyl, $C_{5-7}$-cycloalkyl or phenyl group and $R^{11}$ denotes a hydrogen atom or a $C_{1-3}$-alkyl group.

Preferred groups which may be cleaved from a carboxy group in vivo include a $C_{1-6}$-alkoxy group such as the methoxy, ethoxy, n-propyloxy, isopropyloxy, n-butyloxy, n-pentyloxy, n-hexyloxy or cyclohexyloxy group or a phenyl-$C_{1-3}$-alkoxy group such as the benzyloxy group.

By a group which may be converted in vivo into a hydroxyl group is meant for example a hydroxyl group esterified with a carboxylic acid wherein the carboxylic acid moiety is preferably a $C_{1-7}$-alkanoic acid, a phenyl-$C_{1-3}$-alkanoic acid, a $C_{3-9}$-cycloalkylcarboxylic acid, a $C_{5-7}$-cycloalkenecarboxylic acid, a $C_{3-7}$-alkenoic acid, a phenyl-$C_{3-5}$-alkenoic acid, a $C_{3-7}$-alkynoic acid or phenyl-$C_{3-5}$-alkynoic acid, while individual methylene groups of the carboxylic acid group may be replaced by oxygen atoms, with the proviso that no bond to the oxygen atom starts from a carbon atom which carries a double or triple bond.

Examples of preferred groups which may be cleaved in vivo from a hydroxyl group include a $C_{1-7}$-acyl group such as the formyl, acetyl, n-propionyl, isopropionyl, n-propanoyl, n-butanoyl, n-pentanoyl, n-hexanoyl or cyclohexylcarbonyl group or a benzoyl group and also a methoxyacetyl, 1-methoxypropionyl, 2-methoxypropionyl or 2-methoxy-ethoxy-acetyl group.

The compounds of general formula I, wherein A, $R^4$ and/or $R^5$ contains a group which may be converted in vivo into a carboxy or hydroxyl group are prodrugs for those compounds of general formula I wherein A, $R^4$ and/or $R^5$ contains a carboxy or hydroxyl group.

A 2nd embodiment of the present invention comprises those compounds of general formula I, wherein A denotes a 4- to 7-membered cycloalkyleneimino group, while one or two methylene groups of the cycloalkyleneimino moiety may be substituted in each case by one or two $C_{1-3}$-alkyl groups optionally substituted by a hydroxy, $C_{1-3}$-alkoxy, amino, $C_{1-3}$-alkylamino, di-($C_{1-3}$-alkyl)-amino, a 4- to 7-membered cycloalkyleneimino, $C_{1-5}$-alkylcarbonylamino, $C_{1-5}$-alkylsulphonylamino or $C_{1-5}$-alkyloxycarbonylamino groups or an aminocarbonyl, $C_{1-3}$-alkylaminocarbonyl or di-($C_{1-3}$-alkyl)-aminocarbonyl group and one or two methylene groups of the cycloalkyleneimino moiety not adjacent to the imino group may be substituted by one or two fluorine atoms or a hydroxy, $C_{1-3}$-alkoxy, amino, $C_{1-3}$-alkylamino or di-($C_{1-3}$-alkyl)-amino group and/or a methylene group in the 3 position of a 5-membered cycloalkyleneimino group may be replaced by a sulphur atom, or a methylene group in the 4 position of a 6- or 7-membered cycloalkyleneimino group may be replaced by an oxygen atom or by a —$NR^{8c}$— group and additionally a methylene group adjacent to an above-mentioned —$NR^{8c}$— group may be replaced by a carbonyl group, or an 5- to 7-membered cycloalkenyleneimino group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{1-6}$-cycloalkylamino-$C_{1-3}$-alkyl, aryl, aryl-$C_{1-3}$-alkyl, heteroaryl, heteroaryl-$C_{1-3}$-alkyl, aminocarbonyl, $C_{1-3}$-alkylaminocarbonyl, di-($C_{1-3}$-alkyl)-aminocarbonyl or 4- to 7-membered cycloalkyleneiminocarbonyl groups, while the double bond is not bound to a nitrogen atom and may be fused to a 5- or 6-membered heteroaryl group, $R^1$ denotes a fluorine, chlorine, bromine or iodine atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, or a nitrile group, $R^2$ denotes a hydrogen or halogenatom or a methyl group, $R^3$ denotes a hydrogen atom or a $C_{1-3}$-alkyl group, $R^4$ denotes a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and may optionally be substituted by a nitrile, hydroxy, a $C_{1-5}$-alkyloxy group, while the hydrogen atoms of the $C_{1-5}$-alkyloxy group may optionally be wholly or partly replaced by fluorine atoms, a benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino or $C_{1-5}$-alkylsulphonylamino group, a carboxy, aminocarbonyl, $C_{1-5}$-alkylaminocarbonyl, $C_{3-6}$-cycloalkylamino-carbonyl, di-($C_{1-5}$-alkyl)-aminocarbonyl, $C_{1-5}$-alkoxycarbonyl, $C_{4-6}$-cycloalkyleneiminocarbonyl group, a phenyl, heteroaryl, phenyl-$C_{1-5}$-alkyl or heteroaryl-$C_{1-5}$-alkyl group, which may optionally be mono- to trisubstituted in the phenyl or heteroaryl moiety by identical or different substituents selected from the group consisting of halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a 3- to 7-membered cycloalkyl, cycloalkyleneimino, cycloalkyl-$C_{1-5}$-alkyl or cycloalkyleneimino-$C_{1-3}$-alkyl group, wherein in 4- to 7-membered cyclic groups in the cyclic moiety a methylene group may optionally be replaced by a —N($R^{8c}$)— group, an oxygen or sulphur atom or a —S(O) or —$S(O)_2$ group, or wherein in 4- to 7-membered cyclic groups in the cyclic moiety two adjacent methylene groups may together optionally be replaced by a —C(O)N($R^{8b}$)— or —$S(O)_2$N($R^{8b}$)— group, or wherein in 6- to 7-membered cyclic groups in the cyclic moiety three adjacent methylene groups may together optionally be replaced by a substituted —OC(O)N($R^{8b}$)— or —N($R^{8b}$)C(O)N($R^{8b}$)— or —N($R^{8b}$)$S(O)_2$N($R^{8b}$)— group, with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms from the group oxygen and nitrogen are separated from one another by precisely one optionally substituted —$CH_2$— group, is excluded, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —$CH_2$— groups in each case by one or two $C_{1-3}$-alkyl groups, $R^5$ denotes a hydrogen atom, a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and may optionally be substituted by a $C_{1-5}$-alkyloxy group, while the hydrogen atoms of the $C_{1-5}$-alkyloxy group may optionally be wholly or partly replaced by fluorine atoms, or $R^4$ and $R^5$ together with the carbon atom to which they are bound form a $C_{3-8}$-cycloalkyl or $C_{3-8}$-cycloalkenyl group, while one of the methylene groups of a $C_{4-8}$-cycloalkyl group may be replaced by an oxygen atom or a —N($R^{8c}$)—, or a carbonyl, or sulphonyl group, and/or two directly adjacent methylene groups of a $C_{4-8}$-cycloalkyl group may together be replaced by a —C(O)N($R^{8b}$)— or —$S(O)_2$N($R^{8b}$)— group, and/or three directly adjacent methylene groups of a $C_{6-8}$-cycloalkyl group may together be replaced by a —OC(O)N($R^{8b}$)—, —N($R^{8b}$)C(O)N($R^{8b}$)— or —N($R^{8b}$)$S(O)_2$N($R^{8b}$)— group, while each of the carbon atoms of a $C_{3-8}$-cycloalkyl group may optionally be substituted independently of one another by in each case one or two identical or different halogen atoms or $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino groups, while each of the carbon atoms of a $C_{3-8}$-cycloalkenyl group may optionally be substituted independently of one another by in each case one or two identical or different $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl groups, and each of the carbon atoms of a $C_{4-8}$-cycloalkenyl group which are not bound to another carbon atom by a double bond, may optionally be substituted independently of one another by in each case one or two identical or different fluorine atoms or hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino or $C_{1-5}$-alkylsulphonylamino groups, with the proviso that a $C_{3-8}$-cycloalkyl or $C_{3-8}$-cycloalkenyl group of this kind formed from $R^4$ and $R^5$ together, wherein two heteroatoms in the cyclic group selected from oxygen and nitrogen are separated from one another by precisely one optionally substituted —$CH_2$— group, and/or wherein one or both methylene groups of the cyclic group which are directly connected to the carbon atom to which the groups $R^4$ and $R^5$ are bound, are replaced by a heteroatom from the group oxygen, nitrogen and sulphur, and/or wherein a substituent bound to the cyclic group which is characterised in that a heteroatom selected from among the oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are directly joined together, is excluded, $R^6$ denotes a fluorine, chlorine, bromine or iodine atom, a nitrile group, a $C_{1-3}$-alkyl group, or a $C_{1-3}$-alkoxy group, while the hydrogen atoms of the $C_{1-3}$-alkyl group or $C_{1-3}$-alkoxy group may be wholly or partly replaced by fluorine atoms, $R^{8b}$ in each case independently of one another denotes a hydrogen atom or a $C_{1-5}$-alkyl group, $R^{8c}$ in each case independently of one another denotes a hydrogen atom, a $C_{1-5}$-alkyl, $C_{1-5}$-alkylcarbonyl, $C_{1-5}$-alkyloxycarbonyl or $C_{1-5}$-alkylsulphonyl group, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while unless otherwise stated the alkyl, alkenyl, alkynyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

A 3rd embodiment of the present invention comprises those compounds of general formula I, wherein A denotes a 4- to 7-membered cycloalkyleneimino group, wherein one or two methylene groups of the cycloalkyleneimino moiety may be substituted in each case by one or two $C_{1-3}$-alkyl groups optionally substituted by a hydroxy, $C_{1-3}$-alkoxy, amino, $C_{1-3}$-alkylamino, di-($C_{1-3}$-alkyl)-amino, a 4- to 7-membered cycloalkyleneimino, $C_{1-5}$-alkylcarbonylamino, $C_{1-5}$-alkylsulphonylamino or $C_{1-5}$-alkyloxycarbonylamino groups or an aminocarbonyl, $C_{1-3}$-alkylaminocarbonyl or di-($C_{1-3}$-alkyl)-aminocarbonyl group and one or two methylene groups of the cycloalkyleneimino moiety not adjacent to the imino group may be substituted by one or two fluorine atoms or a hydroxy, $C_{1-3}$-alkoxy, amino, $C_{1-3}$-alkylamino or di-($C_{1-3}$-alkyl)-amino group and/or a methylene group in the 3 position of a 5-membered cycloalkyleneimino group may be replaced by a sulphur atom, or a methylene group in the 4 position of a 6- or 7-membered cycloalkyleneimino group may be replaced by an oxygen atom or by a —$NR^{8c}$— group and additionally a methylene group adjacent to an above-mentioned —$NR^{8c}$— group may be replaced by a carbonyl group, $R^1$ denotes a fluorine, chlorine, bromine or iodine atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, $R^2$ denotes a hydrogen or halogenatom or a methyl group, $R^3$ denotes a hydrogen atom or a methyl group, $R^4$ denotes a $C_{2-4}$-alkenyl or $C_{2-4}$-alkynyl group, a straight-chain or branched $C_{1-4}$-alkyl group, while the hydrogen atoms of the straight-chain or branched $C_{1-4}$-alkyl group may optionally be wholly or partly replaced by fluorine atoms, and may optionally be substituted by a nitrile, hydroxy, a $C_{1-3}$-alkyloxy group, while the hydrogen atoms of the $C_{1-3}$-alkyloxy group may optionally be wholly or partly replaced by fluorine atoms, a benzyloxy, $C_{1-3}$-alkylcarbonyloxy, $C_{1-3}$-alkyloxycarbonyl-$C_{1-3}$-alkyloxy, $C_{1-3}$-alkyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, amino, $C_{1-3}$-alkylamino, di-($C_{1-3}$-alkyl)-amino, $C_{1-3}$-alkylcarbonylamino or $C_{1-3}$-alkylsulphonylamino group, a phenyl, heteroaryl, phenyl-$C_{1-2}$-alkyl or heteroaryl-$C_{1-2}$-alkyl group, where the heteroaryl group is selected from the group consisting of pyrrolyl, oxazolyl, imidazolyl, furanyl, thiophenyl, 1,2,4-triazolyl, 1,2,3-triazolyl, tetrazolyl, pyridinyl, pyrimidinyl and pyrazinyl, and may optionally be mono- to disubstituted in the heteroaryl moiety by identical or different substituents selected from the group consisting of halogen atoms, $C_{1-3}$-alkyl, hydroxy, $C_{1-3}$-alkyloxy, mono-, di- and trifluoromethoxy groups, $R^5$ denotes a hydrogen atom, a $C_{2-4}$-alkenyl or $C_{2-4}$-alkynyl group, a straight-chain or branched $C_{1-4}$-alkyl group, while the hydrogen atoms of the straight-chain or branched $C_{1-4}$-alkyl group may optionally be wholly or partly replaced by fluorine atoms, and may optionally be substituted by a $C_{1-3}$-alkyloxy group, while the hydrogen atoms of the $C_{1-3}$-alkyloxy group may optionally be wholly or partly replaced by fluorine atoms, or $R^4$ and $R^5$ together with the carbon atom to which they are bound form a $C_{3-8}$-cycloalkyl or $C_{3-8}$-cycloalkenyl group, while one of the methylene groups of a $C_{4-8}$-cycloalkyl group may be replaced by an oxygen atom or a —N($R^{8c}$)— group, and/or two directly adjacent methylene groups of a $C_{4-8}$-cycloalkyl group may together be replaced by a —C(O)N($R^{8b}$)— or —S(O)$_2$N($R^{8b}$)— group, and/or three directly adjacent methylene groups of a $C_{6-8}$-cycloalkyl group may together be replaced by a —OC(O)N($R^{8b}$), —N($R^{8b}$)C(O)N($R^{8b}$)— or —N($R^{8b}$)S(O)$_2$N($R^{8b}$)— group, while one or two of the carbon atoms of a $C_{3-8}$-cycloalkyl group may optionally be substituted independently of one another by in each case one or two identical or different fluorine atoms or $C_{1-3}$-alkyl, hydroxy, $C_{1-3}$-alkyloxy, amino, $C_{1-3}$-alkylamino, di-($C_{1-3}$-alkyl)-amino or $C_{1-3}$-alkylcarbonylamino groups, while one or two of the carbon atoms of a $C_{3-8}$-cycloalkenyl group may optionally be substituted independently of one another by one or two $C_{1-3}$-alkyl groups, and one or two of the carbon atoms of a $C_{4-8}$-cycloalkenyl group which are not bound to another carbon atom by a double bond, may optionally be substituted independently of one another by one or two fluorine atoms or hydroxy, $C_{1-3}$-alkyloxy, di-($C_{1-3}$-alkyl)-amino groups, with the proviso that a $C_{3-8}$-cycloalkyl or $C_{3-8}$-cycloalkenyl group of this kind formed from $R^4$ and $R^5$ together, wherein two heteroatoms in the cyclic group selected from oxygen and nitrogen are separated from one another by precisely one optionally substituted —$CH_2$— group, and/or wherein one or both methylene groups of the cyclic group which are directly connected to the carbon atom to which the groups $R^4$ and $R^5$ are bound, are replaced by a heteroatom selected from among oxygen, nitrogen and sulphur, and/or wherein a substituent bound to the cyclic group which is characterised in that a heteroatom selected from among the oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are directly joined together, is excluded, $R^6$ denotes a fluorine, chlorine, bromine or iodine atom, a methyl group, or a methoxy group, while the hydrogen atoms of the methyl group or methoxy group may be wholly or partly replaced by fluorine atoms, $R^{8b}$ in each case independently of one another denotes a hydrogen atom or a $C_{1-3}$-alkyl group, $R^{8c}$ in each case independently of one another denotes a hydrogen atom, a $C_{1-3}$-alkyl, $C_{1-3}$-alkylcarbonyl, $C_{1-4}$-alkyloxycarbonyl or $C_{1-3}$-alkylsulphonyl group, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the previously mentioned definitions, which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

A 4th embodiment of the present invention comprises those compounds of general formula I, wherein A denotes a 4- to 7-membered cycloalkyleneimino group, while one or two methylene groups of the cycloalkyleneimino moiety may be substituted in each case by one or two $C_{1-3}$-alkyl groups optionally substituted by a hydroxy, $C_{1-3}$-alkoxy, amino, $C_{1-3}$-alkylamino, di-($C_{1-3}$-alkyl)-amino, a 4- to 7-membered cycloalkyleneimino, $C_{1-5}$-alkylcarbonylamino, $C_{1-5}$-alkylsulphonylamino or $C_{1-5}$-alkyloxycarbonylamino groups or an aminocarbonyl, $C_{1-3}$-alkylaminocarbonyl or di-($C_{1-3}$-alkyl)-aminocarbonyl group and one or two methylene groups of the cycloalkyleneimino moiety not adjacent to the imino group may be substituted by one or two fluorine atoms or a hydroxy, $C_{1-3}$-alkoxy, amino, $C_{1-3}$-alkylamino or di-($C_{1-3}$-alkyl)-amino group and/or a methylene group in the 3 position of a 5-membered cycloalkyleneimino group may be replaced by a sulphur atom, or a methylene group in the 4 position of a 6- or 7-membered cycloalkyleneimino group may be replaced by an oxygen atom or by a —$NR^{8c}$— group and additionally a methylene group adjacent to an above-mentioned —$NR^{8c}$— group may be replaced by a carbonyl group, $R^1$ denotes a fluorine, chlorine, bromine atom, a methyl, trifluoromethyl or methoxy group, $R^2$ denotes a hydrogen or fluorine atom, $R^3$ denotes a hydrogen atom, $R^4$ denotes a straight-chain or branched $C_{1-4}$-alkyl group, while the hydrogen atoms of the straight-chain or branched $C_{1-4}$-alkyl group may optionally be wholly or partly replaced by fluorine atoms, and may optionally be substituted by a hydroxy, a $C_{1-3}$-alkyloxy group, while the hydrogen atoms of the $C_{1-3}$-alkyloxy group may optionally be wholly or partly replaced by fluorine atoms, a benzyloxy, $C_{1-3}$-alkylcarbonyloxy, amino, $C_{1-3}$-alkylamino or di-($C_{1-3}$-alkyl)-amino group, a phenyl, heteroaryl, phenyl-$C_{1-2}$-alkyl or heteroaryl-$C_{1-2}$-alkyl group, while the heteroaryl group is selected from the group consisting of pyrrolyl, oxazolyl, imidazolyl, furanyl, thiophenyl, 1,2,3-triazolyl, 1,2,4-triazolyl, tetrazolyl, pyridinyl, pyrimidinyl and pyrazinyl, and may optionally be mono- to disubstituted in the heteroaryl moiety by identical or different substituents selected from the group consisting of halogen atoms, $C_{1-3}$-alkyl, hydroxy, $C_{1-3}$-alkyloxy, mono-, di- and trifluoromethoxy groups, $R^5$ denotes a hydrogen atom or a straight-chain or branched $C_{1-4}$-alkyl group, while the hydrogen atoms of the straight-chain or branched $C_{1-4}$-alkyl group may optionally be wholly or partly replaced by fluorine atoms, and may optionally be substituted by a $C_{1-3}$-alkyloxy group, while the hydrogen atoms of the $C_{1-3}$-alkyloxy group may be wholly or partly replaced by fluorine atoms, or $R^4$ and $R^5$ together with the carbon atom to which they are bound form a $C_{3-8}$-cycloalkyl group, while one of the methylene groups of a $C_{4-8}$-cycloalkyl group may be replaced by an oxygen atom or a —N($R^{8c}$)— group, while one or two carbon atoms of a $C_{3-8}$-cycloalkyl group may optionally be substituted independently of one another by in each case one or two $C_{1-3}$-alkyl, hydroxy, $C_{1-3}$-alkyloxy or di-($C_{1-3}$-alkyl)-amino groups, with the proviso that a $C_{3-8}$-cycloalkyl group of this kind formed from $R^4$ and $R^5$ together, wherein two heteroatoms in the cyclic group selected from oxygen and nitrogen are separated from one another by precisely one optionally substituted —$CH_2$— group, and/or wherein one or both methylene groups of the cyclic group which are directly connected to the carbon atom to which the groups $R^4$ and $R^5$ are bound are replaced by a heteroatom selected from oxygen and nitrogen, and/or wherein a substituent bound to the cyclic group which is characterised in that a heteroatom selected from oxygen and nitrogen is bound directly to the cyclic group, is separated from another heteroatom selected from oxygen and nitrogen by precisely one, optionally substituted, methylene group, and/or wherein two oxygen atoms are directly joined together, is excluded, $R^6$ denotes a chlorine or bromine atom, $R^{8c}$ in each case independently of one another denotes a hydrogen atom, a $C_{1-3}$-alkyl, $C_{1-3}$-alkylcarbonyl, or $C_{1-4}$-alkyloxycarbonyl group, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the previously mentioned definitions, which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions may be wholly or partly replaced by fluorine atoms, the tautomers, the enantiomers, the diastereomers, the mixtures thereof and the salts thereof.

A 5th embodiment of the present invention comprises those compounds of general formula I corresponding to the embodiments 1, 2, 3 and 4 wherein $R^4$ and $R^5$ do not represent hydrogen.

A 6th embodiment of the present invention comprises those compounds of general formula I corresponding to the embodiments 1, 2, 3, 4 and 5, wherein the group $R^6$ denotes a bromine atom.

A 7th embodiment of the present invention comprises those compounds of general formula I corresponding to the embodiments 1, 2, 3, 4, 5 and 6, wherein $R^4$ and $R^5$ do not represent hydrogen and $R^6$ denotes a bromine atom.

An 8th embodiment of the present invention comprises those compounds of general formula I, wherein A denotes a 4- to 7-membered cycloalkyleneimino group, while one or two methylene groups of the cycloalkyleneimino moiety may be substituted independently of one another by in each case one or two $C_{1-4}$-alkyl groups optionally substituted by a group $R^{7a}$, $R^{7b}$ or $R^{7c}$ or by groups $R^{7b}$ or $R^{7c}$ and/or one or two methylene groups of the cycloalkyleneimino moiety not adjacent to the imino group may be substituted by one or two fluorine atoms or a group $R^{7a}$ and/or a methylene group in the 3 position of a 5-membered cycloalkyleneimino group may be replaced by a sulphur atom, or a methylene group in the 4 position of a 6- or 7-membered cycloalkyleneimino group may be replaced by an oxygen or sulphur atom, by a carbonyl, sulphinyl, sulphonyl group or a $-NR^{8c}-$ group and additionally a methylene group adjacent to an above-mentioned $-NR^{8c}-$ group may be replaced by a carbonyl or sulphonyl group, with the proviso that in a cycloalkyleneimino group, where a methylene group has been replaced by an oxygen or sulphur atom or an $-NR^{8c}-$ group, the adjacent methylene groups may not be substituted by a substituent from the group $R^{7a}$, or a 5- to 7-membered cycloalkenyleneimino group optionally substituted by one or two $C_{1-4}$-alkyl groups optionally substituted by a group $R^{7a}$, $R^{7b}$ or $R^{7c}$, or a group $R^{7b}$ or $R^{7c}$ and/or in the methylene groups of the cycloalkenyleneimino moiety which are not adjacent to the imino group, substituted by one or two fluorine atoms or a group $R^{7a}$, while the ethenylene group is not directly bound to a nitrogen or oxygen atom and may be fused to a 5- or 6-membered heteroaryl group, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a $C_{1-3}$-alkyl group, $R^3$ denotes a hydrogen atom or a $C_{1-3}$-alkyl group, $R^4$ and $R^5$ in each case independently of one another denote a hydrogen atom, a $C_{2-6}$-alkenyl or $C_{2-4}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and may optionally be substituted by a $C_{3-5}$-cycloalkyl group, a group $R^{7a}$ or $R^{7b}$, a $C_{1-4}$-alkyloxy group which is substituted by a group $R^{7b}$, a mercapto, $C_{1-5}$-alkylsulphanyl, $C_{1-5}$-alkylsulphonyl group, a group $R^{7b}$, a group $R^{7c}$ or a $C_{1-5}$-alkyl group substituted by $R^{7c}$, a 3- to 7-membered cycloalkyl, cycloalkyl-$C_{1-5}$-alkyl or cycloalkyleneimino-$C_{1-3}$-alkyl group, wherein in 4- to 7-membered cyclic groups in the cyclic moiety a methylene group may optionally be replaced by a $-N(R^{8c})-$ group, an oxygen or sulphur atom or a $-S(O)$ or $-S(O)_2$ group, or wherein in 4- to 7-membered cyclic groups in the cyclic moiety two adjacent methylene groups may together optionally be replaced by a $-C(O)N(R^{8b})-$ or $-S(O)_2N(R^{8b})-$ group, or wherein in 6- to 7-membered cyclic groups in the cyclic moiety three adjacent methylene groups may together optionally be replaced by a substituted $-OC(O)N(R^{8b})-$ or $-N(R^{8b})C(O)N(R^{8b})-$ or $-N(R^{8b})S(O)_2N(R^{8b})-$ group, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may each be substituted at one or two $-CH_2-$ groups by one or two groups $R^{8a}$, with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms from the group oxygen and nitrogen are separated from one another by precisely one optionally substituted $-CH_2-$ group, is excluded, or $R^4$ and $R^5$ together with the carbon atom to which they are bound form a $C_{3-8}$-cycloalkyl or $C_{3-8}$-cycloalkenyl group, while a $C_{3-8}$-cycloalkyl or $C_{4-8}$-cycloalkenyl group may be substituted at an individual carbon atom by a $C_{2-5}$-alkylene group or simultaneously at two different carbon atoms by a $C_{1-4}$-alkylene group, forming a corresponding spirocyclic group or a bridged bicyclic group, while one of the methylene groups of a $C_{4-8}$-cycloalkyl or $C_{5-8}$-cycloalkenyl group or a corresponding spirocyclic group as described above or a corresponding bridged bicyclic group may be replaced by an oxygen or sulphur atom or a $-N(R^{8c})-$, or a carbonyl, sulphinyl or sulphonyl group, and/or two directly adjacent methylene groups of a $C_{4-8}$-cycloalkyl group may together be replaced by a $-C(O)N(R^{8b})-$, $-C(O)O-$ or $-S(O)_2N(R^{8b})-$ group, and/or three directly adjacent methylene groups of a $C_{6-8}$-cycloalkyl group may together be replaced by a $-OC(O)N(R^{8b})-$, $-N(R^{8b})C(O)N(R^{8b})-$ or $-N(R^{8b})S(O)_2N(R^{8b})-$ group, while 1 to 3 carbon atoms of a $C_{3-8}$-cycloalkyl group or a corresponding spirocyclic group as described above or a corresponding bridged bicyclic group may optionally be substituted independently of one another in each case by one or two fluorine atoms or one or two identical or different $C_{1-5}$-alkyl groups or groups $R^{7a}$ or $R^{7b}$ or carboxy-$C_{1-5}$-alkyl, $C_{1-5}$-alkyloxycarbonyl-$C_{1-5}$-alkyl, $C_{1-5}$-alkylsulphanyl or $C_{1-5}$-alkylsulphonyl groups, while 1 to 2 carbon atoms of a $C_{3-8}$-cycloalkenyl group may optionally be substituted independently of one another in each case by a $C_{1-5}$-alkyl group or a group $R^{7b}$, and 1 to 2 carbon atoms of a $C_{4-8}$-cycloalkenyl group which are not bound to another carbon atom by a double bond, may optionally be substituted independently of one another by one or two fluorine atoms or a group $R^{7a}$, with the proviso that a $C_{3-8}$-cycloalkyl or $C_{3-8}$-cycloalkenyl group of this kind formed from $R^4$ and $R^5$ together or a corresponding spirocyclic group as described above or a corresponding bridged bicyclic group, wherein two heteroatoms in the cyclic group selected from oxygen and nitrogen are separated from one another by precisely one optionally substituted $-CH_2-$ group, and/or wherein one or both methylene groups of the cyclic group which are directly connected to the carbon atom to which the groups $R^4$ and $R^5$ are bound are replaced by a heteroatom selected from among oxygen, nitrogen and sulphur, and/or wherein a substituent bound to the cyclic group which is characterised in that a heteroatom selected from among the oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are directly joined together, and/or wherein a heteroatom selected from among oxygen, nitrogen and sulphur is linked directly to a carbon atom which is linked to another carbon atom by a double bond, and/or which contains a cyclic group with three ring members, one or more of which corresponds to an oxygen or sulphur atom or —N($R^{8c}$)— group, is excluded, $R^6$ denotes a hydrogen, fluorine, chlorine, bromine or iodine atom, a nitrile group, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms, $R^{7a}$ in each case independently of one another denotes a hydroxy, $C_{1-4}$-alkoxy, while the hydrogen atoms of the $C_{1-4}$-alkoxy group may optionally be wholly or partly replaced by fluorine atoms, allyloxy, benzyloxy, propargyloxy, $C_{1-4}$-alkylcarbonyloxy, $C_{1-4}$-alkyloxycarbonyloxy, amino, $C_{1-3}$-alkylamino, $C_{3-6}$-cycloalkylamino, N—($C_{1-3}$-alkyl)-N—($C_{3-6}$-cycloalkyl)-amino, arylamino, heteroarylamino, di-($C_{1-3}$-alkyl)-amino, N—$C_{1-3}$-alkyl-N—($C_{3-6}$-cycloalkyl)-amino, a 4- to 7-membered cycloalkyleneimino, morpholin-4-yl, piperidin-4-yl, piperazin-1-yl, N—$C_{1-3}$-alkyl-piperidin-4-yl, 4-$C_{1-3}$-alkyl-piperazin-1-yl, N—$C_{1-3}$-alkylcarbonyl-piperidin-4-yl, 4-$C_{1-3}$-alkylcarbonyl-piperazin-1-yl, $C_{1-5}$-alkylcarbonylamino, $C_{3-6}$-cycloalkylcarbonylamino, $C_{1-5}$-alkylsulphonylamino, N—($C_{1-5}$-alkylsulphonyl)-$C_{1-5}$-alkylamino, $C_{1-5}$-alkoxycarbonylamino, aminocarbonylamino, $C_{1-4}$-alkylaminocarbonylamino or a di-($C_{1-3}$-alkyl)-aminocarbonylamino group, $R^{7b}$ in each case independently of one another denotes a carboxy, $C_{1-3}$-alkoxycarbonyl, aminocarbonyl, $C_{1-3}$-alkylaminocarbonyl, di-($C_{1-3}$-alkyl)-aminocarbonyl, a 4- to 7-membered cycloalkyleneiminocarbonyl, nitrile, aminosulphonyl, $C_{1-4}$-alkylaminosulphonyl, di-($C_{1-4}$-alkyl)-aminosulphonyl or $C_{3-6}$-cycloalkyleneiminosulphonyl group, $R^{7c}$ in each case independently of one another denotes an aryl or heteroaryl group, $R^{8a}$ in each case independently of one another denotes a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, $C_{3-6}$-cycloalkyleneimino, carboxy, nitrile, $C_{1-3}$-alkoxycarbonyl, aminocarbonyl, $C_{1-3}$-alkylaminocarbonyl or a di-($C_{1-3}$-alkyl)-aminocarbonyl group, $R^{8b}$ in each case independently of one another denotes a hydrogen atom or a $C_{1-5}$-alkyl group, $R^{8c}$ in each case independently of one another denotes a hydrogen atom, a hydroxyl, $C_{1-5}$-alkyl, $C_{3-5}$-cycloalkyl, $C_{1-5}$-alkoxy, formyl, $C_{1-5}$-alkylcarbonyl, $C_{1-5}$-alkyloxycarbonyl or $C_{1-5}$-alkylsulphonyl, aryl or heteroaryl group, while, unless otherwise stated, by the term "aryl group" mentioned hereinbefore in the definitions is preferably meant a phenyl group, which may optionally be substituted by one or two fluorine, chlorine or bromine atom or a group $R^{8a}$, and moreover a phenyl ring optionally substituted by a fluorine, chlorine or bromine atom or a group $R^{8a}$ may be fused to the above-mentioned monocyclic aryl groups via two adjacent carbon atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$cycloalkyleneimino-$C_{1-3}$-alkyl or phenyl-$C_{1-3}$-alkyl group or an oxygen or sulphur atom and additionally a nitrogen atom or an optionally by a $C_{1-3}$-alkyl or phenyl-$C_{1-3}$-alkyl group substituted imino group and two or three nitrogen atoms, and the above-mentioned monocyclic heteroaryl groups may be substituted in the carbon skeleton by one or two groups $R^{8a}$, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the previously mentioned definitions, which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

Examples of monocyclic heteroaryl groups are the pyridyl, N-oxy-pyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thiophenyl, thiazolyl, isothiazolyl, [1,2,3]thiadiazolyl, [1,2,4]thiadiazolyl or [1,2,5]thiadiazolyl group.

Examples of bicyclic heteroaryl groups are the benzimidazolyl, benzofuranyl, benzo[c]furanyl, benzothiophenyl, benzo[c]thiophenyl, benzothiazolyl, benzo[c]-isothiazolyl, benzo[d]isothiazolyl, benzooxazolyl, benzo[c]isoxazolyl, benzo[d]-isoxazolyl, benzo[1,2,5]oxadiazolyl, benzo[1,2,5]thiadiazolyl, benzo[1,2,3]thia-diazolyl, benzo[d][1,2,3]triazinyl, benzo[1,2,4]triazinyl, benzotriazolyl, cinnolinyl, quinolinyl, N-oxy-quinolinyl, isoquinolinyl, quinazolinyl, N-oxy-quinazolinyl, quinoxalinyl, phthalazinyl, indolyl, isoindolyl or 1-oxa-2,3-diaza-indenyl group.

Examples of the $C_{1-6}$-alkyl groups mentioned hereinbefore in the definitions are the methyl, ethyl, 1-propyl, 2-propyl, n-butyl, sec-butyl, tert-butyl, 1-pentyl, 2-pentyl, 3-pentyl, neo-pentyl, 3-methyl-2-butyl, 1-hexyl, 2-hexyl, 3-hexyl, 3-methyl-2-pentyl, 4-methyl-2-pentyl, 3-methyl-3-pentyl, 2-methyl-3-pentyl, 2,2-dimethyl-3-butyl or 2,3-dimethyl-2-butyl group.

Examples of the $C_{1-5}$-alkyloxy groups or $C_{1-5}$-alkoxy groups mentioned hereinbefore in the definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy or neo-pentyloxy group.

Examples of the $C_{2-6}$-alkenyl groups mentioned hereinbefore in the definitions are the ethenyl, 1-propen-1-yl, 2-propen-1-yl, 1-buten-1-yl, 2-buten-1-yl, 3-buten-1-yl, 1-penten-1-yl, 2-penten-1-yl, 3-penten-1-yl, 4-penten-1-yl, 1-hexen-1-yl, 2-hexen-1-yl, 3-hexen-1-yl, 4-hexen-1-yl, 5-hexen-1-yl, but-1-en-2-yl, but-2-en-2-yl, but-1-en-3-yl, 2-methyl-prop-2-en-1-yl, pent-1-en-2-yl, pent-2-en-2-yl, pent-3-en-2-yl, pent-4-en-2-yl, pent-1-en-3-yl, pent-2-en-3-yl, 2-methyl-but-1-en-1-yl, 2-methyl-but-2-en-1-yl, 2-methyl-but-3-en-1-yl, 2-ethyl-prop-2-en-1-yl, hex-1-en-2-yl, hex-2-en-2-yl, hex-3-en-2-yl, hex-4-en-2-yl, hex-5-en-2-yl, hex-1-en-3-yl, hex-2-en-3-yl, hex-3-en-3-yl, hex-4-en-3-yl, hex-5-en-3-yl, hex-1-en-4-yl, hex-2-en-4-yl, hex-3-en-4-yl, hex-4-en-4-yl, hex-5-en-4-yl, 4-methyl-pent-1-en-3-yl, 3-methyl-pent-1-en-3-yl, 2-methyl-pent-1-en-3-yl, 2,3-dimethyl-but-1-en-3-yl, 3,3-dimethyl-but-1-en-2-yl or 2-ethyl-but-1-en-3-yl group, Examples of the $C_{2-6}$-alkynyl groups mentioned hereinbefore in the definitions are die ethynyl, 1-propynyl, 2-propynyl, 1-butyn-1-yl, 1-butyn-3-yl, 2-butyn-1-yl, 3-butyn-1-yl, 1-pentyn-1-yl, 1-pentyn-3-yl, 1-pentyn-4-yl, 2-pentyn-1-yl, 2-pentyn-3-yl, 3-pentyn-1-yl, 4-pentyn-1-yl, 2-methyl-1-butyn-4-yl, 3-methyl-1-butyn-1-yl, 3-methyl-1-butyn-3-yl, 1-hexyn-1-yl, 2-hexyn-1-yl, 3-hexyn-1-yl, 4-hexyn-1-yl, 5-hexyn-1-yl, 1-hexyn-3-yl, 1-hexyn-4-yl, 1-hexyn-5-yl, 2-hexyn-4-yl, 2-hexyn-5-yl, 3-hexyn-5-yl, 3-methyl-1-pentyn-3-yl, 4-methyl-1-pentyn-3-yl, 3-methyl-1-pentyn-4-yl, 4-methyl-1-pentyn-4-yl, 4-methyl-2-pentyn-4-yl, 4-methyl-2-pentyn-1-yl, 2,2-dimethyl-3-butyn-1-yl or 2-ethyl-3-butyn-1-yl group.

By a group which may be converted in vivo into a carboxy group is meant for example a carboxy group esterified with an alcohol wherein the alcoholic moiety preferably denotes a $C_{1-6}$-alkanol, a phenyl-$C_{1-3}$-alkanol, a $C_{3-9}$-cycloalkanol, a $C_{5-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom starts from a carbon atom which carries a double or triple bond, a $C_{3-8}$-cycloalkyl-$C_{1-3}$-alkanol or an alcohol of formula $$R^9—CO—O—(R^{10}CR^{11})—OH,$$

wherein $R^9$ denotes a $C_{1-8}$-alkyl, $C_{5-7}$-cycloalkyl, phenyl or phenyl-$C_{1-3}$-alkyl group, $R^{10}$ denotes a hydrogen atom, a $C_{1-3}$-alkyl, $C_{5-7}$-cycloalkyl or phenyl group and $R^{11}$ denotes a hydrogen atom or a $C_{1-3}$-alkyl group.

Preferred groups which may be cleaved from a carboxy group in vivo include a $C_{1-6}$-alkoxy group such as the methoxy, ethoxy, n-propyloxy, isopropyloxy, n-butyloxy, n-pentyloxy, n-hexyloxy or cyclohexyloxy group or a phenyl-$C_{1-3}$-alkoxy group such as the benzyloxy group.

By a group which may be converted in vivo into a hydroxyl group is meant for example a hydroxyl group esterified with a carboxylic acid wherein the carboxylic acid moiety is preferably a $C_{1-7}$-alkanoic acid, a phenyl-$C_{1-3}$-alkanoic acid, a $C_{3-9}$-cycloalkylcarboxylic acid, a $C_{5-7}$-cycloalkenecarboxylic acid, a $C_{3-7}$-alkenoic acid, a phenyl-$C_{3-5}$-alkenoic acid, a $C_{3-7}$-alkynoic acid or phenyl-$C_{3-5}$-alkynoic acid, while individual methylene groups of the carboxylic acid group may be replaced by oxygen atoms, with the proviso that no bond to the oxygen atom starts from a carbon atom which carries a double or triple bond.

Examples of preferred groups which may be cleaved in vivo from a hydroxyl group include a $C_{1-7}$-acyl group such as the formyl, acetyl, n-propionyl, isopropionyl, n-propanoyl, n-butanoyl, n-pentanoyl, n-hexanoyl or cyclohexylcarbonyl group or a benzoyl group as well as also a methoxyacetyl, 1-methoxypropionyl, 2-methoxypropionyl or 2-methoxyethoxyacetyl group.

The compounds of general formula I, wherein A, $R^4$ and/or $R^5$ contains a group which may be converted in vivo into a carboxy or hydroxyl group are prodrugs for those compounds of general formula I wherein A, $R^4$ and/or $R^5$ contains a carboxy or hydroxyl group.

A 9th embodiment of the present invention comprises those compounds of general formula I, wherein A denotes a 4- to 7-membered cycloalkyleneimino group, where one or two methylene groups of the cycloalkyleneimino moiety may be substituted independently of one another by in each case one or two $C_{1-4}$-alkyl groups optionally substituted by a group $R^{7a}$, $R^{7b}$ or $R^{7c}$, or groups $R^{7b}$ or $R^{7c}$, and/or one or two methylene groups of the cycloalkyleneimino moiety not adjacent to the imino group may be substituted by one or two fluorine atoms or a group $R^{7a}$ and/or a methylene group in the 3 position of a 5-membered cycloalkyleneimino group may be replaced by a sulphur atom, or a methylene group in the 4 position of a 6- or 7-membered cycloalkyleneimino group may be replaced by an oxygen or sulphur atom, by a carbonyl, sulphinyl, sulphonyl group or a $—NR^{8c}—$ group and additionally a methylene group adjacent to an above-mentioned $—NR^{8c}—$ group may be replaced by a carbonyl or sulphonyl group, with the proviso that in a cycloalkyleneimino group wherein a methylene group has been replaced by an oxygen or sulphur atom or a $—NR^{8c}—$ group, the adjacent methylene groups may not be substituted by a substituent from the group $R^{7a}$, or denotes a 5- to 7-membered cycloalkenyleneimino group optionally substituted by one or two $C_{1-4}$-alkyl groups optionally substituted by a group $R^{7a}$, $R^{7b}$ or $R^{7c}$, or a group $R^{7b}$ or $R^{7c}$ and/or in the methylene groups of the cycloalkyleneimino moiety not adjacent to the imino group by one or two fluorine atoms or a group $R^{7a}$, while the ethenylene group is not bound directly to a nitrogen or oxygen atom and may be fused to a 5- or 6-membered heteroaryl group, $R^1$ denotes a hydrogen or fluorine, chlorine, bromine or iodine atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a nitrile, nitro or amino group, $R^2$ denotes a hydrogen or halogen atom or a methyl group, $R^3$ denotes a hydrogen atom or a $C_{1-3}$-alkyl group, $R^4$ and $R^5$ in each case independently of one another denote a hydrogen atom, a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and may optionally be substituted by a $C_{3-5}$-cycloalkyl group, a group $R^{7a}$ or $R^{7b}$, a $C_{1-4}$-alkyloxy group which is substituted by a group $R^{7b}$, a mercapto, $C_{1-5}$-alkylsulphanyl, $C_{1-5}$-alkylsulphonyl group, a group $R^{7b}$, a group $R^{7c}$ or a $C_{1-5}$-alkyl group substituted by $R^{7c}$, a 3- to 7-membered cycloalkyl, cycloalkyl-$C_{1-5}$-alkyl or cycloalkyleneimino-$C_{1-3}$-alkyl group, wherein in 4- to 7-membered cyclic groups in the cyclic moiety a methylene group may optionally be replaced by a —N($R^{8c}$)— group, an oxygen or sulphur atom or a —S(O) or —$S(O)_2$ group, or wherein in 4- to 7-membered cyclic groups in the cyclic moiety two adjacent methylene groups may together optionally be replaced by a —C(O)N($R^{8b}$)— or —$S(O)_2$N($R^{8b}$)— group, or wherein in 6- to 7-membered cyclic groups in the cyclic moiety three adjacent methylene groups may together optionally be replaced by a substituted —OC(O)N ($R^{8b}$)— or —N($R^{8b}$)C(O)N($R^{8b}$)— or —N($R^{8b}$)S $(O)_2$ N($R^{8b}$)— group, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may each be substituted at one or two —$CH_2$— groups by one or two groups $R^{8a}$, with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms from the group oxygen and nitrogen are separated from one another by precisely one optionally substituted —$CH_2$— group, is excluded, or $R^4$ and $R^5$ together with the carbon atom to which they are bound form a $C_{3-8}$-cycloalkyl or $C_{3-8}$-cycloalkenyl group, while a $C_{3-8}$-cycloalkyl or $C_{4-8}$-cycloalkenyl group may be substituted at an individual carbon atom by a $C_{2-5}$-alkylene group or simultaneously at two different carbon atoms by a $C_{1-4}$-alkylene group, forming a corresponding spirocyclic group or a bridged bicyclic group, while one of the methylene groups of a $C_{4-8}$-cycloalkyl or $C_{5-8}$-cycloalkenyl group or a corresponding spirocyclic group as described above or a corresponding bridged bicyclic group may be replaced by an oxygen or sulphur atom or a —N($R^{8c}$)—, or a carbonyl, sulphinyl or sulphonyl group, and/or two directly adjacent methylene groups of a $C_{4-8}$-cycloalkyl group may together be replaced by a —C(O)N ($R^{8b}$)—, —C(O)O— or —$S(O)_2$N($R^{8b}$)— group, and/or three directly adjacent methylene groups of a $C_{6-8}$-cycloalkyl group may together be replaced by a —OC(O) N($R^{8b}$)—, —N($R^{8b}$)C(O)N($R^{8b}$)— or —N($R^{8b}$)S$(O)_2$N ($R^{8b}$)— group, while 1 to 3 carbon atoms of a $C_{3-8}$-cycloalkyl group or a corresponding spirocyclic group as described above or a corresponding bridged bicyclic group may optionally be substituted independently of one another by in each case one or two fluorine atoms or one or two identical or different $C_{1-5}$-alkyl groups or groups $R^{7a}$ or $R^{7b}$ or carboxy-$C_{1-5}$-alkyl, $C_{1-5}$-alkyloxycarbonyl-$C_{1-5}$-alkyl, $C_{1-5}$-alkylsulphanyl or $C_{1-5}$-alkylsulphonyl groups, while 1 to 2 carbon atoms of a $C_{3-8}$-cycloalkenyl group may optionally be substituted independently of one another by in each case a $C_{1-5}$-alkyl groups or a group $R^{7b}$, and 1 to 2 carbon atoms of a $C_{4-8}$-cycloalkenyl group which are not bound to another carbon atom by a double bond may optionally be substituted independently of one another by one or two fluorine atoms or a group $R^{7a}$, with the proviso that a $C_{3-8}$-cycloalkyl or $C_{3-8}$-cycloalkenyl group of this kind formed from $R^4$ and $R^5$ together or a corresponding spirocyclic group as described above or a corresponding bridged bicyclic group, wherein two heteroatoms in the cyclic group selected from oxygen and nitrogen are separated from one another by precisely one optionally substituted —$CH_2$— group, and/or wherein one or both methylene groups of the cyclic group which are directly connected to the carbon atom to which the groups $R^4$ and $R^5$ are bound are replaced by a heteroatom selected from among oxygen, nitrogen and sulphur, and/or wherein a substituent bound to the cyclic group which is characterised in that a heteroatom selected from among the oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are directly joined together, and/or wherein a heteroatom selected from among oxygen, nitrogen and sulphur is linked directly to a carbon atom which is linked to another carbon atom by a double bond, and/or which contains a cyclic group with three ring members, one or more of which corresponds to an oxygen or sulphur atom or —N($R^{8c}$)— group, is excluded, $R^6$ denotes a fluorine, chlorine, bromine or iodine atom, a nitrile group, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms, $R^{7a}$ in each case independently of one another denotes a hydroxy, $C_{1-4}$-alkoxy, while the hydrogen atoms of the $C_{1-4}$-alkoxy group may optionally be wholly or partly replaced by fluorine atoms, allyloxy, benzyloxy, propargyloxy, $C_{1-4}$-alkylcarbonyloxy, $C_{1-4}$-alkyloxycarbonyloxy, amino, $C_{1-3}$-alkylamino, $C_{3-6}$-cycloalkylamino, N—($C_{1-3}$-alkyl)-N—($C_{3-6}$-cycloalkyl)-amino, arylamino, heteroarylamino, di-($C_{1-3}$-alkyl)-amino, N—$C_{1-3}$-alkyl-N—($C_{3-6}$-cycloalkyl)-amino, a 4- to 7-membered cycloalkyleneimino, morpholin-4-yl, piperidin-4-yl, piperazin-1-yl, N—$C_{1-3}$-alkyl-piperidin-4-yl, 4-$C_{1-3}$-alkyl-piperazin-1-yl, N—$C_{1-3}$-alkylcarbonyl-piperidin-4-yl, 4-$C_{1-3}$-alkylcarbonyl-piperazin-1-yl, $C_{1-5}$-alkylcarbonylamino, $C_{3-6}$-cycloalkylcarbonylamino, $C_{1-5}$-alkylsulphonylamino, N—($C_{1-5}$-alkylsulphonyl)-$C_{1-5}$-alkylamino, $C_{1-5}$-alkoxycarbonylamino, aminocarbonylamino, $C_{1-4}$-alkylaminocarbonylamino or a di-($C_{1-3}$-alkyl)-aminocarbonylamino group, $R^{7b}$ in each case independently of one another denotes a carboxy, $C_{1-3}$-alkoxycarbonyl, aminocarbonyl, $C_{1-3}$-alkylaminocarbonyl, di-($C_{1-3}$-alkyl)-aminocarbonyl, a 4- to 7-membered cycloalkyleneiminocarbonyl, nitrile, aminosulphonyl, $C_{1-4}$-alkylaminosulphonyl, di-($C_{1-4}$-alkyl)-aminosulphonyl or $C_{3-6}$-cycloalkyleneiminosulphonyl group, $R^{7c}$ in each case independently of one another denotes an aryl or heteroaryl group, $R^{8a}$ in each case independently of one another denotes a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, $C_{3-6}$-cycloalkyleneimino, carboxy, nitrile, $C_{1-3}$-alkoxycarbonyl, aminocarbonyl, $C_{1-3}$-alkylaminocarbonyl or a di-($C_{1-3}$-alkyl)-aminocarbonyl group, $R^{8b}$ in each case independently of one another denotes a hydrogen atom or a $C_{1-5}$-alkyl group, $R^{8c}$ in each case independently of one another denotes a hydrogen atom, a hydroxyl, $C_{1-5}$-alkyl, $C_{3-5}$-cycloalkyl, $C_{1-5}$-alkoxy, formyl, $C_{1-5}$-alkylcarbonyl, $C_{1-5}$-alkyloxycarbonyl or $C_{1-5}$-alkylsulphonyl, aryl or heteroaryl group, while, unless otherwise stated, by the term "aryl group" mentioned hereinbefore in the definitions is preferably meant a phenyl group, which may optionally be substituted by one or two fluorine, chlorine or bromine atoms or a group $R^{8a}$, and moreover a phenyl ring optionally substituted by a fluorine, chlorine or bromine atom or a group $R^{8a}$ may be fused to the above-mentioned monocyclic aryl groups via two adjacent carbon atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and the above-mentioned monocyclic heteroaryl groups in the carbon skeleton may be substituted by one or two groups $R^{8a}$, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the previously mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 10th embodiment of the present invention comprises those compounds of general formula I, wherein A denotes a 4- to 7-membered cycloalkyleneimino group, while one or two methylene groups of the cycloalkyleneimino moiety may be substituted independently of one another by in each case one or two $C_{1-4}$-alkyl groups optionally substituted by a group $R^{7a}$, $R^{7b}$ or $R^{7c}$, or groups $R^{7b}$ or $R^{7c}$, and/or one or two methylene groups of the cycloalkyleneimino moiety not adjacent to the imino group may be substituted by one or two fluorine atoms or a group $R^{7a}$ and/or a methylene group in the 3 position of a 5-membered cycloalkyleneimino group may be replaced by a sulphur atom, or a methylene group in the 4 position of a 6- or 7-membered cycloalkyleneimino group may be replaced by an oxygen or sulphur atom, by a carbonyl, sulphinyl, sulphonyl group or a —$NR^{8c}$— group and additionally a methylene group adjacent to an above-mentioned —$NR^{8c}$— group may be replaced by a carbonyl or sulphonyl group, with the proviso that in a cycloalkyleneimino group wherein a methylene group has been replaced by an oxygen or sulphur atom or a —$NR^{8c}$— group, the adjacent methylene groups may not be substituted by a substituent from the group $R^{7a}$, or denotes a 5- to 7-membered cycloalkenyleneimino group optionally substituted by one or two $C_{1-4}$-alkyl groups optionally substituted by a group $R^{7a}$, $R^{7b}$ or $R^{7c}$ or a group $R^{7b}$ or $R^{7c}$ and/or in the methylene groups of the cycloalkyleneimino moiety not adjacent to the imino group by one or two fluorine atoms or a group $R^{7a}$, while the ethenylene group is not bound directly to a nitrogen or oxygen atom and may be fused to a 5- or 6-membered heteroaryl group, $R^1$ denotes a hydrogen, fluorine, chlorine, bromine or iodine atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, $R^2$ denotes a hydrogen or halogen atom or a methyl group, $R^3$ denotes a hydrogen atom or a methyl group, $R^4$ denotes a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and may optionally be substituted by a $C_{3-5}$-cycloalkyl group, a group $R^{7a}$ or $R^{7b}$, a $C_{1-4}$-alkyloxy group which is substituted by a group $R^{7b}$, a mercapto, $C_{1-5}$-alkylsulphanyl, $C_{1-5}$-alkylsulphonyl group, a group $R^{7b}$, a group $R^{7c}$ or a $C_{1-5}$-alkyl group substituted by $R^{7c}$ a 3- to 7-membered cycloalkyl, cycloalkyl-$C_{1-5}$-alkyl or cycloalkyleneimino-$C_{1-3}$-alkyl group, wherein in 4- to 7-membered cyclic groups in the cyclic moiety a methylene group may optionally be replaced by a —$N(R^{8c})$— group, an oxygen or sulphur atom or a —S(O) or —$S(O)_2$ group, or wherein in 4- to 7-membered cyclic groups in the cyclic moiety two adjacent methylene groups may together optionally be replaced by a —$C(O)N(R^{8b})$— or —$S(O)_2N(R^{8b})$— group, or wherein in 6- to 7-membered cyclic groups in the cyclic moiety three adjacent methylene groups may together optionally be replaced by a substituted —OC(O)N($R^{8b}$)— or —N($R^{8b}$)C(O)N($R^{8b}$)— or —N($R^{8b}$)S(O)$_2$ N($R^{8b}$)— group, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may each be substituted at one or two —$CH_2$— groups by one or two groups $R^{8a}$, with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms from the group oxygen and nitrogen are separated from one another by precisely one optionally substituted —$CH_2$— group, is excluded, $R^5$ denotes a hydrogen atom, a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and may optionally be substituted by a $C_{1-5}$-alkyloxy group, while the hydrogen atoms of the $C_{1-5}$-alkyloxy group may optionally be wholly or partly replaced by fluorine atoms, or $R^4$ and $R^5$ together with the carbon atom to which they are bound form a $C_{3-8}$-cycloalkyl or $C_{3-8}$-cycloalkenyl group, while a $C_{3-8}$-cycloalkyl or $C_{4-8}$-cycloalkenyl group may be substituted at an individual carbon atom by a $C_{2-5}$-alkylene group or simultaneously at two different carbon atoms by a $C_{1-4}$-alkylene group, forming a corresponding spirocyclic group or a bridged bicyclic group, while one of the methylene groups of a $C_{4-8}$-cycloalkyl or $C_{5-8}$-cycloalkenyl group or a corresponding spirocyclic group as described above or a corresponding bridged bicyclic group may be replaced by an oxygen or sulphur atom or a —N($R^{8c}$)—, or a carbonyl, sulphinyl or sulphonyl group, and/or two directly adjacent methylene groups of a $C_{4-8}$-cycloalkyl group may together be replaced by a —C(O)N($R^{8b}$)—, —C(O)O— or —S(O)$_2$N($R^{8b}$)— group, and/or three directly adjacent methylene groups of a $C_{6-8}$-cycloalkyl group may together be replaced by a —OC(O)N($R^{8b}$)—, —N($R^{8b}$)C(O)N($R^{8b}$)— or —N($R^{8b}$)S(O)$_2$N($R^{8b}$)— group, while 1 to 3 carbon atoms of a $C_{3-8}$-cycloalkyl group or a corresponding spirocyclic group as described above or a corresponding bridged bicyclic group may optionally each be substituted independently of one another by one or two fluorine atoms or one or two identical or different $C_{1-5}$-alkyl groups or groups $R^{7a}$ or $R^{7b}$ or carboxy-$C_{1-5}$-alkyl, $C_{1-5}$-alkyloxycarbonyl-$C_{1-5}$-alkyl, $C_{1-5}$-alkylsulphanyl or $C_{1-5}$-alkylsulphonyl groups, while 1 to 2 carbon atoms of a $C_{3-8}$-cycloalkenyl group may optionally each be substituted independently of one another by a $C_{1-5}$-alkyl groups or a group $R^{7b}$, and 1 to 2 carbon atoms of a $C_{4-8}$-cycloalkenyl group which are not bound to another carbon atom by a double bond may optionally be substituted independently of one another by one or two fluorine atoms or a group $R^{7a}$, with the proviso that a $C_{3-8}$-cycloalkyl or $C_{3-8}$-cycloalkenyl group of this kind formed from $R^4$ and $R^5$ together or a corresponding spirocyclic group as described above or a corresponding bridged bicyclic group, wherein two heteroatoms in the cyclic group selected from oxygen and nitrogen are separated from one another by precisely one optionally substituted —$CH_2$— group, and/or wherein one or both methylene groups of the cyclic group which are directly connected to the carbon atom to which the groups $R^4$ and $R^5$ are bound are replaced by a heteroatom selected from among oxygen, nitrogen and sulphur, and/or wherein a substituent bound to the cyclic group which is characterised in that a heteroatom selected from among the oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are directly joined together, and/or wherein a heteroatom selected from among oxygen, nitrogen and sulphur is linked directly to a carbon atom which is linked to another carbon atom by a double bond, and/or which contains a cyclic group with three ring members, one or more of which corresponds to an oxygen or sulphur atom or —N($R^{8c}$)— group, is excluded, $R^6$ denotes a fluorine, chlorine, bromine or iodine atom, a nitrile group, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms, $R^{7a}$ in each case independently of one another denotes a hydroxy, $C_{1-4}$-alkoxy, while the hydrogen atoms of the $C_{1-4}$-alkoxy group may optionally be wholly or partly replaced by fluorine atoms, allyloxy, benzyloxy, propargyloxy, $C_{1-4}$-alkylcarbonyloxy, $C_{1-4}$-alkyloxycarbonyloxy, amino, $C_{1-3}$-alkylamino, $C_{3-6}$-cycloalkylamino, N—($C_{1-3}$-alkyl)-N—($C_{3-6}$-cycloalkyl)-amino, arylamino, heteroarylamino, di-($C_{1-3}$-alkyl)-amino, N—$C_{1-3}$-alkyl-N—($C_{3-6}$-cycloalkyl)-amino, a 4- to 7-membered cycloalkyleneimino, morpholin-4-yl, piperidin-4-yl, piperazin-1-yl, N—$C_{1-3}$-alkyl-piperidin-4-yl, 4-$C_{1-3}$-alkyl-piperazin-1-yl, N—$C_{1-3}$-alkylcarbonyl-piperidin-4-yl, 4-$C_{1-3}$-alkylcarbonyl-piperazin-1-yl, $C_{1-5}$-alkylcarbonylamino, $C_{3-6}$-cycloalkylcarbonylamino, $C_{1-5}$-alkylsulphonylamino, N—($C_{1-5}$-alkylsulphonyl)-$C_{1-5}$-alkylamino, $C_{1-5}$-alkoxycarbonylamino, aminocarbonylamino, $C_{1-4}$-alkylaminocarbonylamino or a di-($C_{1-3}$-alkyl)-aminocarbonylamino group, $R^{7b}$ in each case independently of one another denotes a carboxy, $C_{1-3}$-alkoxycarbonyl, aminocarbonyl, $C_{1-3}$-alkylaminocarbonyl, di-($C_{1-3}$-alkyl)-aminocarbonyl, a 4- to 7-membered cycloalkyleneiminocarbonyl, nitrile, aminosulphonyl, $C_{1-4}$-alkylaminosulphonyl, di-($C_{1-4}$-alkyl)-aminosulphonyl or $C_{3-6}$-cycloalkyleneiminosulphonyl group, $R^{7c}$ in each case independently of one another denotes an aryl or heteroaryl group, $R^{8a}$ in each case independently of one another denotes a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, $C_{3-6}$-cycloalkyleneimino, carboxy, nitrile, $C_{1-3}$-alkoxycarbonyl, aminocarbonyl, $C_{1-3}$-alkylaminocarbonyl or a di-($C_{1-3}$-alkyl)-aminocarbonyl group, $R^{8b}$ in each case independently of one another denotes a hydrogen atom or a $C_{1-5}$-alkyl group, $R^{8c}$ in each case independently of one another denotes a hydrogen atom, a hydroxyl, $C_{1-5}$-alkyl, $C_{3-5}$-cycloalkyl, $C_{1-5}$-alkoxy, formyl, $C_{1-5}$-alkylcarbonyl, $C_{1-5}$-alkyloxycarbonyl or $C_{1-5}$-alkylsulphonyl, aryl or heteroaryl group, while, unless otherwise stated, by the term "aryl group" mentioned hereinbefore in the definitions is preferably meant a phenyl group, which may optionally be substituted by one or two fluorine, chlorine or bromine atom or a group $R^{8a}$, and moreover a phenyl ring optionally substituted by a fluorine, chlorine or bromine atom or a group $R^{8a}$ may be fused to the above-mentioned monocyclic aryl groups via two adjacent carbon atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and the above-mentioned monocyclic heteroaryl groups in the carbon skeleton may be substituted by one or two groups $R^{8a}$, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the previously mentioned definitions, which have more than two carbon atoms, may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

An 11th embodiment of the present invention comprises those compounds of general formula I wherein A denotes a 4- to 7-membered cycloalkyleneimino group, while one or two methylene groups of the cycloalkyleneimino moiety may each be substituted independently of one another by one or two $C_{1-4}$-alkyl groups optionally substituted by a group $R^{7a}$, $R^{7b}$ or $R^{7c}$, or groups $R^{7b}$ or $R^{7c}$ and/or one or two methylene groups of the cycloalkyleneimino moiety not adjacent to the imino group may be substituted by one or two fluorine atoms or a group $R^{7a}$ and/or a methylene group in the 3 position of a 5-membered cycloalkyleneimino group may be replaced by a sulphur atom, or a methylene group in the 4 position of a 6- or 7-membered cycloalkyleneimino group may be replaced by an oxygen or sulphur atom, by a carbonyl, sulphinyl, sulphonyl group or a $R^{8c}$ group and additionally a methylene group adjacent to an above-mentioned —$NR^{8c}$— group may be replaced by a carbonyl or sulphonyl group, with the proviso that in a cycloalkyleneimino group wherein a methylene group has been replaced by an oxygen or sulphur atom or a —$NR^{8c}$— group, the adjacent methylene groups may not be substituted by a substituent from the group $R^{7a}$, or denotes a 5- to 7-membered cycloalkenyleneimino group optionally substituted by one or two $C_{1-4}$-alkyl groups optionally substituted by a group $R^{7a}$, $R^{7b}$ or $R^{7c}$, or a group $R^{7b}$ or $R^{7c}$ and/or in the methylene groups of the cycloalkyleneimino moiety not adjacent to the imino group may be substituted by one or two fluorine atoms or a group $R^{7a}$, while the ethenylene group is not bound directly to a nitrogen or oxygen atom and may be fused to a 5- or 6-membered heteroaryl group, $R^1$ denotes a hydrogen, fluorine, chlorine, bromine or iodine atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, $R^2$ denotes a hydrogen or halogen atom or a methyl group, $R^3$ denotes a hydrogen atom, $R^4$ denotes a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and may optionally be substituted by a $C_{3-5}$-cycloalkyl group, a group $R^{7d}$ or $R^{7e}$, a $C_{1-4}$-alkyloxy group which is substituted by a group $R^{7e}$, a $C_{1-5}$-alkylsulphanyl, $C_{1-5}$-alkylsulphonyl group, a group $R^{7c}$ or a $C_{1-5}$-alkyl group substituted by $R^{7c}$, $R^5$ denotes a hydrogen atom, a $C_{2-4}$-alkenyl or $C_{2-4}$-alkynyl group, a straight-chain or branched $C_{1-4}$-alkyl group, while the hydrogen atoms of the straight-chain or branched $C_{1-4}$-alkyl group may optionally be wholly or partly replaced by fluorine atoms, and may optionally be substituted by a $C_{1-4}$-alkyloxy group, while the hydrogen atoms of the $C_{1-4}$-alkyloxy group may optionally be wholly or partly replaced by fluorine atoms, or $R^4$ and $R^5$ together with the carbon atom to which they are bound form a $C_{3-8}$-cycloalkyl or $C_{3-8}$-cycloalkenyl group, while a $C_{3-8}$-cycloalkyl or $C_{4-8}$-cycloalkenyl group may be substituted at an individual carbon atom by a $C_{2-5}$-alkylene group or simultaneously at two different carbon atoms by a $C_{1-4}$-alkylene group, forming a corresponding spirocyclic group or a bridged bicyclic group, while one of the methylene groups of a $C_{4-8}$-cycloalkyl or $C_{5-8}$-cycloalkenyl group or a corresponding spirocyclic group as described above or a corresponding bridged bicyclic group may be replaced by an oxygen or sulphur atom or a —N($R^{8c}$)—, or a carbonyl, sulphinyl or sulphonyl group, and/or two directly adjacent methylene groups of a $C_{4-8}$-cycloalkyl group may together be replaced by a —C(O)N($R^{8b}$)—, —C(O)O— or —$S(O)_2N(R^{8b})$— group, and/or three directly adjacent methylene groups of a $C_{6-8}$-cycloalkyl group may together be replaced by a —OC(O)N($R^{8b}$)—, —N($R^{8b}$)C(O)N($R^{8b}$)— or —N($R^{8b}$)$S(O)_2N(R^{8b})$— group, while 1 to 3 carbon atoms of a $C_{3-8}$-cycloalkyl group or a corresponding spirocyclic group as described above or a corresponding bridged bicyclic group may optionally each be substituted independently of one another by one or two fluorine atoms or one or two identical or different $C_{1-5}$-alkyl groups or groups $R^{7d}$ or $R^{7e}$ or $C_{1-5}$-alkylsulphanyl or $C_{1-5}$-alkylsulphonyl groups, while 1 to 2 carbon atoms of a $C_{3-8}$-cycloalkenyl group may optionally each be substituted independently of one another by a $C_{1-5}$-alkyl groups or a group $R^{7e}$, and 1 to 2 carbon atoms of a $C_{4-8}$-cycloalkenyl group which are not bound to another carbon atom by a double bond may optionally be substituted independently of one another by one or two fluorine atoms or a group $R^{7d}$, with the proviso that a $C_{3-8}$-cycloalkyl or $C_{3-8}$-cycloalkenyl group of this kind formed from $R^4$ and $R^5$ together or a corresponding spirocyclic group as described above or a corresponding bridged bicyclic group, wherein two heteroatoms in the cyclic group selected from oxygen and nitrogen are separated from one another by precisely one optionally substituted —$CH_2$— group, and/or wherein one or both methylene groups of the cyclic group which are directly connected to the carbon atom to which the groups $R^4$ and $R^5$ are bound are replaced by a heteroatom selected from among oxygen, nitrogen and sulphur, and/or wherein a substituent bound to the cyclic group which is characterised in that a heteroatom selected from among the oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are directly joined together, and/or wherein a heteroatom selected from among oxygen, nitrogen and sulphur is linked directly to a carbon atom which is linked to another carbon atom by a double bond, and/or which contains a cyclic group with three ring members, one or more of which corresponds to an oxygen or sulphur atom or —N($R^{8c}$)— group, is excluded, $R^6$ denotes a fluorine, chlorine, bromine or iodine atom, a nitrile, methyl or methoxy group, while the hydrogen atoms of the methyl or methoxy group may optionally be wholly or partly replaced by fluorine atoms, $R^{7a}$ in each case independently of one another denotes a hydroxy, $C_{1-4}$-alkoxy, while the hydrogen atoms of the $C_{1-4}$-alkoxy group may optionally be wholly or partly replaced by fluorine atoms, allyloxy, benzyloxy, propargyloxy, $C_{1-4}$-alkylcarbonyloxy, $C_{1-4}$-alkyloxycarbonyloxy, amino, $C_{1-3}$-alkylamino, $C_{3-6}$-cycloalkylamino, N—($C_{1-3}$-alkyl)-N—($C_{3-6}$-cycloalkyl)-amino, arylamino, heteroarylamino, di-($C_{1-3}$-alkyl)-amino, N—$C_{1-3}$-alkyl-N—($C_{3-6}$-cycloalkyl)-amino, a 4- to 7-membered cycloalkyleneimino, morpholin-4-yl, piperidin-4-yl, piperazin-1-yl, N—$C_{1-3}$-alkyl-piperidin-4-yl, 4-$C_{1-3}$-alkyl-piperazin-1-yl, N—$C_{1-3}$-alkylcarbonyl-piperidin-4-yl, 4-$C_{1-3}$-alkylcarbonyl-piperazin-1-yl, $C_{1-5}$-alkylcarbonylamino, $C_{3-6}$-cycloalkylcarbonylamino, $C_{1-5}$-alkylsulphonylamino, N—($C_{1-5}$-alkylsulphonyl)-$C_{1-5}$-alkylamino, $C_{1-5}$-alkoxycarbonylamino, aminocarbonylamino, $C_{1-4}$-alkylaminocarbonylamino or a di-($C_{1-3}$-alkyl)-aminocarbonylamino group, $R^{7b}$ in each case independently of one another denotes a carboxy, $C_{1-3}$-alkoxycarbonyl, aminocarbonyl, $C_{1-3}$-alkylaminocarbonyl, di-($C_{1-3}$-alkyl)-aminocarbonyl, a 4- to 7-membered cycloalkyleneiminocarbonyl, nitrile, aminosulphonyl, $C_{1-4}$-alkylaminosulphonyl, di-($C_{1-4}$-alkyl)-aminosulphonyl or $C_{3-6}$-cycloalkyleneiminosulphonyl group, $R^{7c}$ in each case independently of one another denotes an aryl or heteroaryl group, $R^{7d}$ in each case independently of one another denotes a hydroxy, $C_{1-4}$-alkoxy, while the hydrogen atoms of the $C_{1-4}$-alkoxy group may optionally be wholly or partly replaced by fluorine atoms, $C_{1-4}$-alkylcarbonyloxy, $C_{1-3}$-alkylamino, di-($C_{1-3}$-alkyl)-amino, $C_{1-5}$-alkylcarbonylamino or $C_{1-5}$-alkoxycarbonylamino group, $R^{7e}$ in each case independently of one another denotes a $C_{1-3}$-alkoxycarbonyl, aminocarbonyl, $C_{1-3}$-alkylaminocarbonyl, di-($C_{1-3}$-alkyl)-aminocarbonyl, nitrile, aminosulphonyl, $C_{1-4}$-alkylaminosulphonyl or di-($C_{1-4}$-alkyl)-aminosulphonyl group, $R^{8a}$ in each case independently of one another denotes a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, $C_{3-6}$-cycloalkyleneimino, carboxy, nitrile, $C_{1-3}$-alkoxycarbonyl, aminocarbonyl, $C_{1-3}$-alkylaminocarbonyl or a di-($C_{1-3}$-alkyl)-aminocarbonyl group, $R^{8b}$ in each case independently of one another denotes a hydrogen atom or a $C_{1-5}$-alkyl group, $R^{8c}$ in each case independently of one another denotes a hydrogen atom, a hydroxyl, $C_{1-5}$-alkyl, $C_{3-5}$-cycloalkyl, $C_{1-5}$-alkoxy, formyl, $C_{1-5}$-alkylcarbonyl, $C_{1-5}$-alkyloxycarbonyl or $C_{1-5}$-alkylsulphonyl, aryl or heteroaryl group, while, unless otherwise stated, by the term "aryl group" mentioned hereinbefore in the definitions is preferably meant a phenyl group, which may optionally be substituted by one or two fluorine, chlorine or bromine atom or a group $R^{8a}$, and moreover a phenyl ring optionally substituted by a fluorine, chlorine or bromine atom or a group $R^{8a}$ may be fused to the above-mentioned monocyclic aryl groups via two adjacent carbon atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group, or an oxygen or sulphur atom and additionally a nitrogen atom or an imino group optionally substituted by a $C_{1-3}$-alkyl or phenyl-$C_{1-3}$-alkyl group, and two or three nitrogen atoms, and the above-mentioned monocyclic heteroaryl groups may be substituted in the carbon skeleton by one or two groups $R^{8a}$, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the previously mentioned definitions, which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 12th embodiment of the present invention comprises those compounds of general formula I, wherein A denotes a 4- to 7-membered cycloalkyleneimino group, while one or two methylene groups of the cycloalkyleneimino moiety may each be substituted independently of one another by one or two $C_{1-4}$-alkyl groups optionally substituted by a group $R^{7a}$, $R^{7b}$ or $R^{7c}$, or groups $R^{7b}$ or $R^{7c}$, and/or one or two methylene groups of the cycloalkyleneimino moiety not adjacent to the imino group may be substituted by one or two fluorine atoms or by a group $R^{7a}$ and/or a methylene group in the 3 position of a 5-membered cycloalkyleneimino group may be replaced by a sulphur atom, or a methylene group in the 4 position of a 6- or 7-membered cycloalkyleneimino group may be replaced by an oxygen or sulphur atom, by a carbonyl, sulphinyl, sulphonyl group or a —$NR^{8c}$— group and additionally a methylene group adjacent to an above-mentioned —$NR^{8c}$— group may be replaced by a carbonyl or sulphonyl group, with the proviso that in a cycloalkyleneimino group wherein a methylene group has been replaced by an oxygen or sulphur atom or a —$NR^{8c}$— group, the adjacent methylene groups may not be substituted by a substituent from the group $R^{7a}$, or denotes a 5- to 7-membered cycloalkenyleneimino group optionally substituted by one or two $C_{1-4}$-alkyl groups optionally substituted by a group $R^{7a}$, $R^{7b}$ or $R^{7c}$, or a group $R^{7b}$ or $R^{7c}$ and/or in the methylene groups of the cycloalkyleneimino moiety not adjacent to the imino group substituted by one or two fluorine atoms or a group $R^{7a}$, while the ethenylene group is not bound directly to a nitrogen or oxygen atom and may be fused to a 5- or 6-membered heteroaryl group, $R^1$ denotes a hydrogen, fluorine, chlorine, bromine or iodine atom, a methyl or methoxy group, while the hydrogen atoms of the methyl or methoxy group may optionally be wholly or partly replaced by fluorine atoms, $R^2$ denotes a hydrogen or fluorine atom or a methyl group, $R^3$ denotes a hydrogen atom, $R^4$ denotes a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and may optionally be substituted by a $C_{3-5}$-cycloalkyl group, a group $R^{7d}$ or $R^{7e}$, a $C_{1-4}$-alkyloxy group which is substituted by a group $R^{7e}$, a $C_{1-5}$-alkylsulphanyl, $C_{1-5}$-alkylsulphonyl group, a group $R^{7c}$ or a $C_{1-5}$-alkyl group substituted by $R^{7c}$, $R^5$ denotes a hydrogen atom, a $C_{2-4}$-alkenyl or $C_{2-4}$-alkynyl group, a straight-chain or branched $C_{1-4}$-alkyl group, while the hydrogen atoms of the straight-chain or branched $C_{1-4}$-alkyl group may optionally be wholly or partly replaced by fluorine atoms, and may optionally be substituted by a $C_{1-4}$-alkyloxy group, while the hydrogen atoms of the $C_{1-4}$-alkyloxy group may optionally be wholly or partly replaced by fluorine atoms, or $R^4$ and $R^5$ together with the carbon atom to which they are bound form a $C_{3-8}$-cycloalkyl or $C_{3-8}$-cycloalkenyl group, while a $C_{3-8}$-cycloalkyl or $C_{4-8}$-cycloalkenyl group may be substituted at an individual carbon atom by a $C_{2-5}$-alkylene group or simultaneously at two different carbon atoms by a $C_{1-4}$-alkylene group, forming a corresponding spirocyclic group or a bridged bicyclic group, while one of the methylene groups of a $C_{4-8}$-cycloalkyl or $C_{5-8}$-cycloalkenyl group or a corresponding spirocyclic group as described above or a corresponding bridged bicyclic group may be replaced by an oxygen or sulphur atom or a —$N(R^{8c})$— or sulphonyl group, and/or two directly adjacent methylene groups of a $C_{4-8}$-cycloalkyl group may together be replaced by a —C(O)N($R^{8b}$)—, —C(O)O— or —$S(O)_2N(R^{8b})$— group, and/or three directly adjacent methylene groups of a $C_{6-8}$-cycloalkyl group may together be replaced by a —OC(O)N($R^{8b}$)—, —N($R^{8b}$)C(O)N($R^{8b}$)— or —N($R^{8b}$)$S(O)_2$N($R^{8b}$)— group, while 1 to 2 carbon atoms of a $C_{3-8}$-cycloalkyl group or a corresponding spirocyclic group as described above or a corresponding bridged bicyclic group may optionally each be substituted independently of one another by one or two fluorine atoms or a $C_{1-3}$-alkyl groups or a group $R^{7d}$ or $R^{7e}$, with the proviso that a $C_{3-8}$-cycloalkyl or $C_{3-8}$-cycloalkenyl group of this kind formed from $R^4$ and $R^5$ together or a corresponding spirocyclic group as described above or a corresponding bridged bicyclic group, wherein two heteroatoms in the cyclic group selected from oxygen and nitrogen are separated from one another by precisely one optionally substituted $—CH_2—$ group, and/or wherein one or both methylene groups of the cyclic group which are directly connected to the carbon atom to which the groups $R^4$ and $R^5$ are bound are replaced by a heteroatom selected from among oxygen, nitrogen and sulphur, and/or wherein a substituent bound to the cyclic group which is characterised in that a heteroatom selected from among the oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are directly joined together, and/or wherein a heteroatom selected from among oxygen, nitrogen and sulphur is linked directly to a carbon atom which is linked to another carbon atom by a double bond, and/or which contains a cyclic group with three ring members, one or more of which corresponds to an oxygen or sulphur atom or $—N(R^{8c})—$ group, is excluded, $R^6$ denotes a fluorine, chlorine, bromine or iodine atom, a methyl or methoxy group, while the hydrogen atoms of the methyl or methoxy group may optionally be wholly or partly replaced by fluorine atoms, $R^{7a}$ in each case independently of one another denotes a hydroxy, $C_{1-4}$-alkoxy, while the hydrogen atoms of the $C_{1-4}$-alkoxy group may optionally be wholly or partly replaced by fluorine atoms, $C_{1-4}$-alkylcarbonyloxy, $C_{1-4}$-alkyloxycarbonyloxy, amino, $C_{1-3}$-alkylamino, $C_{3-6}$-cycloalkylamino, $N—(C_{1-3}$-alkyl)-$N—(C_{3-6}$-cycloalkyl)-amino, arylamino, heteroarylamino, di-($C_{1-3}$-alkyl)-amino, $N—C_{1-3}$-alkyl-$N—(C_{3-6}$-cycloalkyl)-amino, a 4- to 7-membered cycloalkyleneimino, morpholin-4-yl, piperidin-4-yl, piperazin-1-yl, $N—C_{1-3}$-alkyl-piperidin-4-yl, 4-$C_{1-3}$-alkyl-piperazin-1-yl, $N—C_{1-3}$-alkylcarbonyl-piperidin-4-yl, 4-$C_{1-3}$-alkylcarbonyl-piperazin-1-yl, $C_{1-5}$-alkylcarbonylamino, $C_{3-6}$-cycloalkylcarbonylamino, $C_{1-5}$-alkylsulphonylamino, $N—(C_{1-5}$-alkylsulphonyl)-$C_{1-5}$-alkylamino, $C_{1-5}$-alkoxycarbonylamino, aminocarbonylamino, $C_{1-4}$-alkylaminocarbonylamino or a di-($C_{1-3}$-alkyl)-aminocarbonylamino group, $R^{7b}$ in each case independently of one another denotes a carboxy, $C_{1-3}$-alkoxycarbonyl, aminocarbonyl, $C_{1-3}$-alkylaminocarbonyl, di-($C_{1-3}$-alkyl)-aminocarbonyl, a 4- to 7-membered cycloalkyleneiminocarbonyl, nitrile, aminosulphonyl, $C_{1-4}$-alkylaminosulphonyl, di-($C_{1-4}$-alkyl)-aminosulphonyl or $C_{3-6}$-cycloalkyleneiminosulphonyl group, $R^{7c}$ in each case independently of one another denotes an aryl or heteroaryl group, $R^{7d}$ in each case independently of one another denotes a hydroxy, $C_{1-4}$-alkoxy, while the hydrogen atoms of the $C_{1-4}$-alkoxy group may optionally be wholly or partly replaced by fluorine atoms, $C_{1-4}$-alkylcarbonyloxy, $C_{1-3}$-alkylamino, di-($C_{1-3}$-alkyl)-amino, $C_{1-5}$-alkylcarbonylamino or $C_{1-5}$-alkoxycarbonylamino group, $R^{7e}$ in each case independently of one another denotes a $C_{1-3}$-alkoxycarbonyl, aminocarbonyl, $C_{1-3}$-alkylaminocarbonyl, di-($C_{1-3}$-alkyl)-aminocarbonyl, nitrile, aminosulphonyl, $C_{1-4}$-alkylaminosulphonyl or di-($C_{1-4}$-alkyl)-aminosulphonyl group, $R^{8a}$ in each case independently of one another denotes a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, $C_{3-6}$-cycloalkyleneimino, carboxy, nitrile, $C_{1-3}$-alkoxycarbonyl, aminocarbonyl, $C_{1-3}$-alkylaminocarbonyl or a di-($C_{1-3}$-alkyl)-aminocarbonyl group, $R^{8b}$ in each case independently of one another denotes a hydrogen atom or a $C_{1-5}$-alkyl group, $R^{8c}$ in each case independently of one another denotes a hydrogen atom, a hydroxyl, $C_{1-5}$-alkyl, $C_{3-5}$-cycloalkyl, $C_{1-5}$-alkoxy, formyl, $C_{1-5}$-alkylcarbonyl, $C_{1-5}$-alkyloxycarbonyl or $C_{1-5}$-alkylsulphonyl, aryl or heteroaryl group, while, unless otherwise stated, by the term “aryl group” mentioned hereinbefore in the definitions is preferably meant a phenyl group, which may optionally be substituted by one or two fluorine, chlorine or bromine atom or a group $R^{8a}$, and moreover a phenyl ring optionally substituted by a fluorine, chlorine or bromine atom or a group $R^{8a}$, may be fused to the above-mentioned monocyclic aryl groups via two adjacent carbon atoms, while, unless otherwise stated, by the term “heteroaryl group” mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-4}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and the above-mentioned monocyclic heteroaryl groups may be substituted in the carbon skeleton by one or two groups $R^{8a}$, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term “halogen atom” mentioned hereinbefore in the definitions is meant an atom selected from among fluorine, chlorine, bromine and iodine, while the alkyl, alkynyl and alkoxy groups contained in the previously mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 13th embodiment of the present invention comprises those compounds of general formula I, wherein A denotes a 4- to 7-membered cycloalkyleneimino group, while one or two methylene groups of the cycloalkyleneimino moiety may each be substituted independently of one another by one or two $C_{1-4}$-alkyl groups optionally substituted by a group $R^{7a}$, $R^{7b}$ or $R^{7c}$, or groups $R^{7b}$ or $R^{7c}$, and/or one or two methylene groups of the cycloalkyleneimino moiety not adjacent to the imino group may be substituted by one or two fluorine atoms or a group $R^{7a}$ and/or a methylene group in the 3 position of a 5-membered cycloalkyleneimino group may be replaced by a sulphur atom, or a methylene group in the 4 position of a 6- or 7-membered cycloalkyleneimino group may be replaced by an oxygen or sulphur atom, by a sulphonyl group or a —$NR^{8c}$— group and additionally a methylene group adjacent to an above-mentioned —$NR^{8c}$— group may be replaced by a carbonyl or sulphonyl group, with the proviso that in a cycloalkyleneimino group wherein a methylene group has been replaced by an oxygen or sulphur atom or a —$NR^{8c}$— group, the adjacent methylene groups may not be substituted by a substituent from the group $R^{7a}$, or denotes a 5- to 7-membered cycloalkenyleneimino group optionally substituted by one or two $C_{1-4}$-alkyl groups optionally substituted by a group $R^{7a}$, $R^{7b}$ or $R^{7c}$, or a group $R^{7b}$ or $R^{7c}$, and/or, in the methylene groups of the cycloalkyleneimino moiety not adjacent to the imino group, substituted by one or two fluorine atoms or a group $R^{7a}$, while the ethenylene group is not bound directly to a nitrogen or oxygen atom, $R^1$ denotes a hydrogen, fluorine, chlorine, bromine or iodine atom, a methyl or methoxy group, while the hydrogen atoms of the methyl or methoxy group may optionally be wholly or partly replaced by fluorine atoms, $R^2$ denotes a hydrogen or fluorine atom, $R^3$ denotes a hydrogen atom, $R^4$ denotes a straight-chain or branched $C_{1-4}$-alkyl group, while the hydrogen atoms of the straight-chain or branched $C_{1-4}$-alkyl group may optionally be wholly or partly replaced by fluorine atoms, and may optionally be substituted by a $C_{3-5}$-cycloalkyl group, a group $R^{7d}$ or $R^{7e}$, a $C_{1-4}$-alkyloxy group which is substituted by a group $R^{7e}$, a $C_{1-4}$-alkylsulphanyl, $C_{1-4}$-alkylsulphonyl group, a group $R^{7c}$ or a $C_{1-3}$-alkyl group substituted by $R^{7c}$, $R^5$ denotes a hydrogen atom, a straight-chain or branched $C_{1-4}$-alkyl group, while the hydrogen atoms of the straight-chain or branched $C_{1-4}$-alkyl group may optionally be wholly or partly replaced by fluorine atoms, and may optionally be substituted by a $C_{1-4}$-alkyloxy group, while the hydrogen atoms of the $C_{1-4}$-alkyloxy group may optionally be wholly or partly replaced by fluorine atoms, or $R^4$ and $R^5$ together with the carbon atom to which they are bound form a $C_{3-7}$-cycloalkyl or $C_{4-7}$-cycloalkenyl group, while a $C_{3-7}$-cycloalkyl or $C_{4-7}$-cycloalkenyl group may be substituted at an individual carbon atom by a $C_{2-5}$-alkylene group or simultaneously at two different carbon atoms by a $C_{1-4}$-alkylene group, forming a corresponding spirocyclic group or a bridged bicyclic group, while one of the methylene groups of a $C_{4-7}$-cycloalkyl or $C_{5-7}$-cycloalkenyl group or a corresponding spirocyclic group as described above or a corresponding bridged bicyclic group may be replaced by an oxygen or sulphur atom or a —$N(R^{8c})$— or sulphonyl group, and/or two directly adjacent methylene groups of a $C_{4-7}$-cycloalkyl group may together be replaced by a —C(O)N($R^{8b}$)— or —C(O)O— group, while 1 to 2 carbon atoms of a $C_{3-8}$-cycloalkyl group or a corresponding spirocyclic group as described above or a corresponding bridged bicyclic group may optionally each be substituted independently of one another by one or two fluorine atoms or a $C_{1-3}$-alkyl groups or a group $R^{7d}$ or $R^{7e}$, with the proviso that a $C_{3-8}$-cycloalkyl or $C_{3-8}$-cycloalkenyl group of this kind formed from $R^4$ and $R^5$ together or a corresponding spirocyclic group as described above or a corresponding bridged bicyclic group, wherein two heteroatoms in the cyclic group selected from oxygen and nitrogen are separated from one another by precisely one optionally substituted —$CH_2$— group, and/or wherein one or both methylene groups of the cyclic group which are directly connected to the carbon atom to which the groups $R^4$ and $R^5$ are bound are replaced by a heteroatom selected from among oxygen, nitrogen and sulphur, and/or wherein a substituent bound to the cyclic group which is characterised in that a heteroatom selected from among the oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are directly joined together, and/or wherein a heteroatom selected from among oxygen, nitrogen and sulphur is linked directly to a carbon atom which is linked to another carbon atom by a double bond, and/or which contains a cyclic group with three ring members, one or more of which corresponds to an oxygen or sulphur atom or —$N(R^{8c})$— group, is excluded, $R^6$ denotes a chlorine or bromine atom, $R^{7a}$ in each case independently of one another denotes a hydroxy, $C_{1-4}$-alkoxy, while the hydrogen atoms of the $C_{1-4}$-alkoxy group may optionally be wholly or partly replaced by fluorine atoms, $C_{1-4}$-alkylcarbonyloxy, $C_{1-4}$-alkyloxycarbonyloxy, amino, $C_{1-3}$-alkylamino, phenylamino, di-($C_{1-3}$-alkyl)-amino, a 4- to 7-membered cycloalkyleneimino, morpholin-4-yl, piperidin-4-yl, piperazin-1-yl, N—$C_{1-3}$-alkyl-piperidin-4-yl, 4-$C_{1-3}$-alkyl-piperazin-1-yl, N—$C_{1-3}$-alkylcarbonyl-piperidin-4-yl, 4-$C_{1-3}$-alkylcarbonyl-piperazin-1-yl, $C_{1-5}$-alkylcarbonylamino, $C_{3-6}$-cycloalkylcarbonylamino, $C_{1-4}$-alkylaminocarbonylamino, $C_{1-5}$-alkylsulphonylamino, N—($C_{1-5}$-alkylsulphonyl)-$C_{1-5}$-alkylamino or $C_{1-5}$-alkoxycarbonylamino group, $R^{7b}$ in each case independently of one another denotes a $C_{1-3}$-alkoxycarbonyl, aminocarbonyl, $C_{1-3}$-alkylaminocarbonyl, di-($C_{1-3}$-alkyl)-aminocarbonyl, a 4- to 7-membered cycloalkyleneiminocarbonyl, nitrile, aminosulphonyl, $C_{1-4}$-alkylaminosulphonyl, di-($C_{1-4}$-alkyl)-aminosulphonyl or $C_{3-6}$-cycloalkyleneiminosulphonyl group, $R^{7c}$ in each case independently of one another denotes an aryl or heteroaryl group, $R^{7d}$ in each case independently of one another denotes a hydroxy, $C_{1-4}$-alkoxy, while the hydrogen atoms of the $C_{1-4}$-alkoxy group may optionally be wholly or partly replaced by fluorine atoms, $C_{1-4}$-alkylcarbonyloxy, $C_{1-3}$-alkylamino, di-($C_{1-3}$-alkyl)-amino, $C_{1-5}$-alkylcarbonylamino or $C_{1-5}$-alkoxycarbonylamino group, $R^{7e}$ in each case independently of one another denotes a $C_{1-3}$-alkoxycarbonyl, aminocarbonyl, $C_{1-3}$-alkylaminocarbonyl, di-($C_{1-3}$-alkyl)-aminocarbonyl, nitrile, aminosulphonyl, $C_{1-4}$-alkylaminosulphonyl or di-($C_{1-4}$-alkyl)-aminosulphonyl group, $R^{8a}$ in each case independently of one another denotes a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, nitrile, $C_{1-3}$-alkylaminocarbonyl or a di-($C_{1-3}$-alkyl)-aminocarbonyl group, $R^{8b}$ in each case independently of one another denotes a hydrogen atom or a $C_{1-3}$-alkyl group, $R^{8c}$ in each case independently of one another denotes a hydrogen atom, a $C_{1-3}$-alkyl, $C_{3-5}$-cycloalkyl, $C_{1-3}$-alkoxy, formyl, $C_{1-3}$-alkylcarbonyl or $C_{1-4}$-alkyloxycarbonyl group, while, unless otherwise stated, by the term "aryl group" mentioned hereinbefore in the definitions is meant a phenyl group, which may optionally be substituted by one or two fluorine, chlorine or bromine atom or a group $R^{8a}$, while the "heteroaryl group" mentioned in the definitions given hereinbefore is selected from the group consisting of pyrrolyl, oxazolyl, imidazolyl, furanyl, thiophenyl, thiazolyl, 1,2,3-triazolyl, 1,2,4-triazolyl, tetrazolyl, pyridinyl, pyrimidinyl and pyrazinyl, and may optionally be mono- to disubstituted in the carbon skeleton by identical or different substituents selected from the group consisting of halogen atoms and $R^{8a}$, while the NH groups contained in 5-membered heteroaryl groups may be substituted by a group $R^{8b}$, while, unless otherwise stated, by the term "halogen atom" mentioned hereinbefore in the definitions is meant an atom selected from among fluorine, chlorine, bromine and iodine, while the alkyl and alkoxy groups contained in the definitions given hereinbefore which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 14th embodiment of the present invention comprises those compounds of general formula I, wherein A denotes a 5- to 7-membered cycloalkyleneimino group, while one or two methylene groups of the cycloalkyleneimino moiety may each be substituted independently of one another by one or two $C_{1-4}$-alkyl groups optionally substituted by a group $R^{7a}$, $R^{7b}$ or $R^{7c}$, or groups $R^{7b}$ or $R^{7c}$, and/or one or two methylene groups of the cycloalkyleneimino moiety not adjacent to the imino group may be substituted by one or two fluorine atoms or a group $R^{7a}$ and/or a methylene group in the 3 position of a 5-membered cycloalkyleneimino group may be replaced by a sulphur atom, or a methylene group in the 4 position of a 6- or 7-membered cycloalkyleneimino group may be replaced by an oxygen or sulphur atom or a —$NR^{8c}$— group and additionally a methylene group adjacent to an above-mentioned —$NR^{8c}$— group may be replaced by a carbonyl group, with the proviso that in a cycloalkyleneimino group wherein a methylene group has been replaced by an oxygen or sulphur atom or a —$NR^{8c}$— group, the adjacent methylene groups may not be substituted by a substituent from the group $R^{7a}$, or denotes a 5- to 7-membered cycloalkenyleneimino group optionally substituted by one or two $C_{1-4}$-alkyl groups optionally substituted by a group $R^{7a}$, $R^{7b}$ or $R^{7c}$ or a group $R^{7b}$ or $R^{7c}$ and/or, in the methylene groups of the cycloalkyleneimino moiety not adjacent to the imino group, by one or two fluorine atoms or a group $R^{7a}$, while the ethenylene group is not bound directly to a nitrogen or oxygen atom, $R^1$ denotes a hydrogen, fluorine, chlorine, bromine atom or a methyl or methoxy group, while the hydrogen atoms of the methyl or methoxy group may optionally be wholly or partly replaced by fluorine atoms, $R^2$ denotes a hydrogen or fluorine atom, $R^3$ denotes a hydrogen atom, $R^4$ denotes a straight-chain or branched $C_{1-3}$-alkyl group which may optionally be substituted by a $C_{3-5}$-cycloalkyl group, a group $R^{7d}$ or $R^{7e}$, a $C_{1-2}$-alkyloxy group, a $C_{1-2}$-alkylsulphanyl, $C_{1-2}$-alkylsulphonyl group, a group $R^{7c}$ or a $C_{1-3}$-alkyl group substituted by $R^{7c}$, $R^5$ denotes a hydrogen atom, or a methyl group, or $R^4$ and $R^5$ together with the carbon atom to which they are bound form a $C_{3-6}$-cycloalkyl or $C_{5-6}$-cycloalkenyl group, while a $C_{3-6}$-cycloalkyl or $C_{5-6}$-cycloalkenyl group may be substituted at an individual carbon atom by a $C_{2-4}$-alkylene group or simultaneously at two different carbon atoms by a $C_{1-4}$-alkylene group, forming a corresponding spirocyclic group or a bridged bicyclic group, while one of the methylene groups of a $C_{4-6}$-cycloalkyl or $C_{5-6}$-cycloalkenyl group or a corresponding spirocyclic group as described above or a corresponding bridged bicyclic group may be replaced by an oxygen or sulphur atom or a —$N(R^{8c})$— or sulphonyl group, with the proviso that a $C_{3-7}$-cycloalkyl or $C_{5-6}$-cycloalkenyl group of this kind formed from $R^4$ and $R^5$ together or a corresponding spirocyclic group as described above or a corresponding bridged bicyclic group, wherein a methylene groups of the cyclic group which are directly connected to the carbon atom to which the groups $R^4$ and $R^5$ are bound are replaced by a heteroatom selected from among oxygen, nitrogen and sulphur, and/or wherein a heteroatom selected from among oxygen, nitrogen and sulphur is linked directly to a carbon atom which is linked to another carbon atom by a double bond, and/or which contains a cyclic group with three ring members, one of which corresponds to an oxygen or sulphur atom or the —$N(R^{8c})$— group, is excluded, $R^6$ denotes a chlorine or bromine atom, $R^{7a}$ in each case independently of one another denotes a hydroxy, $C_{1-4}$-alkoxy, $C_{1-4}$-alkylcarbonyloxy, amino, $C_{1-3}$-alkylamino, phenylamino, di-($C_{1-3}$-alkyl)-amino, a 4- to 7-membered cycloalkyleneimino, morpholin-4-yl, piperidin-4-yl, piperazin-1-yl, N—$C_{1-3}$-alkyl-piperidin-4-yl, 4-$C_{1-3}$-alkyl-piperazin-1-yl, N—$C_{1-3}$-alkylcarbonyl-piperidin-4-yl, 4-$C_{1-3}$-alkylcarbonyl-piperazin-1-yl, $C_{1-5}$-alkylcarbonylamino, $C_{3-6}$-cycloalkylcarbonylamino, $C_{1-4}$-alkylaminocarbonylamino, $C_{1-5}$-alkylsulphonylamino, N—($C_{1-5}$-alkylsulphonyl)-$C_{1-5}$-alkylamino or $C_{1-5}$-alkoxycarbonylamino group, $R^{7b}$ in each case independently of one another denotes a $C_{1-3}$-alkoxycarbonyl, aminocarbonyl, $C_{1-3}$-alkylaminocarbonyl, di-($C_{1-3}$-alkyl)-aminocarbonyl, a 4- to 7-membered cycloalkyleneiminocarbonyl, aminosulphonyl, $C_{1-4}$-alkylaminosulphonyl, di-($C_{1-4}$-alkyl)-aminosulphonyl or $C_{3-6}$-cycloalkyleneiminosulphonyl group, $R^{7c}$ in each case independently of one another denotes an aryl or heteroaryl group, $R^{7d}$ in each case independently of one another denotes a hydroxy, $C_{1-4}$-alkoxy, while the hydrogen atoms of the $C_{1-4}$-alkoxy group may optionally be wholly or partly replaced by fluorine atoms, $C_{1-4}$-alkylcarbonyloxy, $C_{1-3}$-alkylamino, di-($C_{1-3}$-alkyl)-amino, $C_{1-5}$-alkylcarbonylamino or $C_{1-5}$-alkoxycarbonylamino group, $R^{7e}$ in each case independently of one another denotes a $C_{1-3}$-alkoxycarbonyl, aminocarbonyl, $C_{1-3}$-alkylaminocarbonyl, di-($C_{1-3}$-alkyl)-aminocarbonyl, nitrile, aminosulphonyl, $C_{1-4}$-alkylaminosulphonyl or di-($C_{1-4}$-alkyl)-aminosulphonyl group, $R^{8a}$ in each case independently of one another denotes a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, nitrile, $C_{1-3}$-alkylaminocarbonyl or a di-($C_{1-3}$-alkyl)-aminocarbonyl group, $R^{8c}$ in each case independently of one another denotes a hydrogen atom, a $C_{1-3}$-alkyl, $C_{3-5}$-cycloalkyl, $C_{1-3}$-alkoxy, formyl, $C_{1-3}$-alkylcarbonyl or $C_{1-4}$-alkyloxycarbonyl group, while, unless otherwise stated, by the term "aryl group" mentioned hereinbefore in the definitions is meant a phenyl group, which may optionally be substituted by one or two fluorine, chlorine or bromine atoms or a group $R^{8a}$, while the "heteroaryl group" mentioned in the definitions given hereinbefore is selected from the group consisting of imidazolyl, furanyl, oxazolyl, tetrazolyl, pyridinyl, pyrimidinyl and pyrazinyl, while one or two carbon atoms or the NH group contained in 5-membered heteroaryl groups may be substituted by a group $R^{8b}$, while, unless otherwise stated, by the term "halogen atom" mentioned hereinbefore in the definitions is meant an atom selected from among fluorine, chlorine, bromine and iodine, while the alkyl and alkoxy groups contained in the definitions given hereinbefore which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 15th embodiment of the present invention comprises those compounds of general formula I, wherein A denotes a 5- to 7-membered cycloalkyleneimino group, while one or two methylene groups of the cycloalkyleneimino moiety may each be substituted independently of one another by one or two $C_{1-3}$-alkyl groups optionally substituted by a group $R^{7a}$, $R^{7b}$ or $R^{7c}$, or groups $R^{7b}$ or $R^{7c}$, and/or one or two methylene groups of the cycloalkyleneimino moiety not adjacent to the imino group may be substituted by one or two fluorine atoms or a group $R^{7a}$ and/or a methylene group in the 3 position of a 5-membered cycloalkyleneimino group may be replaced by a sulphur atom, or a methylene group in the 4 position of a 6- or 7-membered cycloalkyleneimino group may be replaced by an oxygen or sulphur atom or a —$NR^{8c}$— group and additionally a methylene group adjacent to an above-mentioned —$NR^{8c}$— group may be replaced by a carbonyl group, with the proviso that in a cycloalkyleneimino group wherein a methylene group has been replaced by an oxygen or sulphur atom or a —$NR^{8c}$— group, the adjacent methylene groups may not be substituted by a substituent from the group $R^{7a}$, or denotes a 5- to 7-membered cycloalkenyleneimino group, while the ethenylene group is not bound directly to a nitrogen atom, $R^1$ denotes a hydrogen, chlorine or bromine atom or a methyl group, $R^2$ denotes a hydrogen or fluorine atom, $R^3$ denotes a hydrogen atom, $R^4$ denotes a straight-chain or branched $C_{1-3}$-alkyl group which may optionally be substituted by a group $R^{7d}$, a group $R^{7c}$ or a $C_{1-3}$-alkyl group substituted by $R^{7c}$, $R^5$ denotes a hydrogen atom, or a methyl group, or $R^4$ and $R^5$ together with the carbon atom to which they are bound form a $C_{3-6}$-cycloalkyl group, while one of the methylene groups of a $C_{4-6}$-cycloalkyl group may be replaced by an oxygen atom or a —$N(R^{8c})$— group, with the proviso that a $C_{3-7}$-cycloalkyl group of this kind formed from $R^4$ and $R^5$ together, wherein a methylene groups of the cyclic group which are directly connected to the carbon atom to which the groups $R^4$ and $R^5$ are bound are replaced by a heteroatom selected from oxygen and nitrogen, is excluded, $R^6$ denotes a chlorine or bromine atom, $R^{7a}$ in each case independently of one another denotes a hydroxy, $C_{1-4}$-alkoxy, amino, $C_{1-3}$-alkylamino, phenylamino, di-($C_{1-3}$-alkyl)-amino, a 4- to 7-membered cycloalkyleneimino, $C_{1-5}$-alkylsulphonylamino, or $C_{1-4}$-alkylaminocarbonylamino group, $R^{7b}$ in each case independently of one another denotes a $C_{1-3}$-alkoxycarbonyl, aminocarbonyl, $C_{1-3}$-alkylaminocarbonyl or di-($C_{1-3}$-alkyl)-aminocarbonyl group, $R^{7c}$ in each case independently of one another denotes an aryl or heteroaryl group, $R^{7d}$ in each case independently of one another denotes a hydroxy or $C_{1-3}$-alkoxy group, $R^{8c}$ in each case independently of one another denotes a hydrogen atom, a $C_{1-3}$-alkyl, formyl, or $C_{1-3}$-alkylcarbonyl group, while, unless otherwise stated, by the term "aryl group" mentioned hereinbefore in the definitions is meant a phenyl group, while the "heteroaryl group" mentioned in the definitions given hereinbefore is selected from the group consisting of imidazolyl and pyridinyl, while, unless otherwise stated, by the term "halogen atom" mentioned hereinbefore in the definitions is meant an atom selected from among fluorine, chlorine, bromine and iodine, while the alkyl and alkoxy groups contained in the definitions given hereinbefore which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 16th embodiment of the present invention comprises those compounds of general formula I corresponding to the embodiments 8, 9, 10, 11, 12, 13, 14 or 15, wherein $R^4$ and $R^5$ do not represent hydrogen.

A 17th embodiment of the present invention comprises those compounds of general formula I corresponding to the embodiments 9, 10, 11, 12, 13, 14, 15 or 16, wherein $R^4$ and $R^5$ together with the carbon atom to which they are bound form a cyclic group which is defined in each case as in the 9th, 10th, 11th, 12th, 13th, 14th or 15th embodiment.

An 18th embodiment of the present invention comprises those compounds of general formula I corresponding to the embodiments 9, 10, 11, 12, 13, 14, 15, 16 or 17, wherein $R^4$ and $R^5$ together with the carbon atom to which they are bound form a cyclic group which is defined in each case as in the 9th, 10th, 11th, 12th, 13th, 14th or 15th embodiment, while in the cyclic group or the corresponding bridged bicyclic group or the spirocyclic group according to the measures described a methylene group is replaced by an oxygen atom or a $N(R^{8c})$ group.

A 19th embodiment of the present invention comprises those compounds of general formula I corresponding to the embodiments 9, 10, 11, 12, 13, 14, 16, 17 or 18, wherein $R^4$ and $R^5$ together with the carbon atom to which they are bound form a cyclic group, which by corresponding substitution as described in the 9th, 10th, 11th, 12th, 13th or 14th embodiment denotes a bridged bicyclic group or a spirocyclic group.

A 20th embodiment of the present invention comprises those compounds of general formula I corresponding to the embodiments 9, 10, 11, 12, 13, 14, 15, 16, 17 or 18, wherein $R^4$ and $R^5$ together with the carbon atom to which they are bound denote a cyclic group

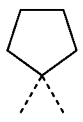

or

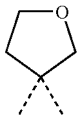

A 21st embodiment of the present invention comprises those compounds of general formula I corresponding to the embodiments 9, 10, 11, 12, 13, 14, 16, 17, 18 or 19, wherein $R^4$ and $R^5$ together with the carbon atom to which they are bound denote a bridged bicyclic group

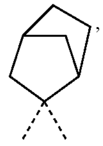

,

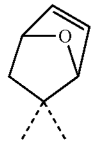

or

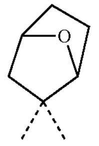

A 22nd embodiment of the present invention comprises those compounds of general formula I corresponding to the embodiments 9, 10, 11, 12, 13, 14, 15, 16, 17, 18, 19, 20 or 21, wherein A denotes a 5- to 7-membered cycloalkyleneimino group, while a methylene group of the cycloalkyleneimino moiety may be substituted by a $C_{1-3}$-alkyl or pyridyl group optionally substituted by a hydroxy, $C_{1-3}$-alkoxy, di-($C_{1-3}$-alkyl)-amino, a 5- to 6-membered cycloalkyleneimino, $C_{1-3}$-alkylcarbonylamino or $C_{1-3}$-alkylsulphonylamino group.

A 23rd embodiment of the present invention comprises those compounds of general formula I corresponding to the embodiments 9, 10, 11, 12, 13, 14, 15, 16, 17, 18, 19, 20, 21 or 22, wherein A denotes a 5- to 7-membered cycloalkyleneimino group, while a methylene group in the 4 position of a 6- or 7-membered cycloalkyleneimino group may be replaced by an oxygen atom or by a $—NR^{8c}—$ group and additionally a methylene group adjacent to an above-mentioned $—NR^{8c}—$ group may be replaced by a carbonyl group.

A 24th embodiment of the present invention comprises those compounds of general formula I corresponding to the embodiments 9, 10, 11, 12, 13, 14, 15, 16, 17, 18, 19, 20, 21, 22 and 23, wherein $R^6$ denotes a bromine atom.

A 25th embodiment of the present invention comprises those compounds of general formula I corresponding to the embodiments 9, 10, 11, 12, 13, 14, 15, 16, 17, 18, 19, 20, 21, 22 and 23, wherein $R^6$ denotes a chlorine atom.

The following preferred compounds of general formula I will now be mentioned by way of example:

(1) 5-chloro-thiophene-2-carboxylic acid-N-{1-[3-chloro-4-(pyrrolidin-1-yl-carbonyl)-phenylcarbamoyl]-ethyl}-amide, (2) 5-chloro-thiophene-2-carboxylic acid-N-{(1R)-2-methoxy-1-[3-methyl-4-(pyrrolidin-1-yl-carbonyl)-phenylcarbamoyl]-ethyl}-amide, (3) 5-chloro-thiophene-2-carboxylic acid-N-{(1S)-2-methoxy-1-[3-methyl-4-(pyrrolidin-1-yl-carbonyl)-phenylcarbamoyl]-ethyl}-amide, (4) 5-bromo-thiophene-2-carboxylic acid-N-{(1R)-2-methoxy-1-methyl-1-[3-methyl-4-(pyrrolidin-1-yl-carbonyl)-phenylcarbamoyl]-ethyl}-amide, (5) 5-bromo-thiophene-2-carboxylic acid-N-{(1S)-2-methoxy-1-methyl-1-[3-methyl-4-(pyrrolidin-1-yl-carbonyl)-phenylcarbamoyl]-ethyl}-amide, (6) 5-bromo-thiophene-2-carboxylic acid-N-{1-methyl-1-[3-methyl-4-(pyrrolidin-1-yl-carbonyl)-phenylcarbamoyl]-ethyl}-amide, (7) 5-chloro-thiophene-2-carboxylic acid-N-{1-methyl-1-[3-methyl-4-(pyrrolidin-1-yl-carbonyl)-phenylcarbamoyl]-ethyl}-amide, (8) 5-bromo-thiophene-2-carboxylic acid-N-{1-methyl-1-[3-chloro-4-(pyrrolidin-1-yl-carbonyl)-phenylcarbamoyl]-ethyl}-amide, (9) 5-chloro-thiophene-2-carboxylic acid-N-{1-methyl-1-[3-chloro-4-(pyrrolidin-1-yl-carbonyl)-phenylcarbamoyl]-ethyl}-amide,

(10) 5-bromo-thiophene-2-carboxylic acid-N-{1-methyl-1-[3-bromo-4-(pyrrolidin-1-yl-carbonyl)-phenylcarbamoyl]-ethyl}-amide,

(11) 5-chloro-thiophene-2-carboxylic acid-N-{1-methyl-1-[3-bromo-4-(pyrrolidin-1-yl-carbonyl)-phenylcarbamoyl]-ethyl}-amide,

(12) 5-bromo-thiophene-2-carboxylic acid-N-{1-methyl-1-[3-methyl-4-(2,5-dihydropyrrol-1-yl-carbonyl)-phenylcarbamoyl]-ethyl}-amide,

(13) 5-bromo-thiophene-2-carboxylic acid-N-{1-methyl-1-[3-methyl-4-(thiazolidin-3-yl-carbonyl)-phenylcarbamoyl]-ethyl}-amide,

(14) 5-bromo-thiophene-2-carboxylic acid-N-{1-methyl-1-[3-methyl-4-(2-dimethylaminomethylpyrrolidin-1-yl-carbonyl)-phenylcarbamoyl]-ethyl}-amide,

(15) 5-bromo-thiophene-2-carboxylic acid-N-{1-methyl-1-[3-methyl-4-(3-fluorpyrrolidin-1-yl-carbonyl)-phenylcarbamoyl]-ethyl}-amide,

(16) 5-bromo-thiophene-2-carboxylic acid-N-{1-methyl-1-[3-methyl-4-(2-methylpyrrolidin-1-yl-carbonyl)-phenylcarbamoyl]-ethyl}-amide,

(17) 5-bromo-thiophene-2-carboxylic acid-N-{1-methyl-1-[3-methyl-4-(piperidin-1-yl-carbonyl)-phenylcarbamoyl]-ethyl}-amide,

(18) 5-bromo-thiophene-2-carboxylic acid-N-{1-methyl-1-[3-methyl-4-(morpholin-4-yl-carbonyl)-phenylcarbamoyl]-ethyl}-amide,

(19) 5-bromo-thiophene-2-carboxylic acid-N-{1-methyl-1-[3-chloro-4-(morpholin-4-yl-carbonyl)-phenylcarbamoyl]-ethyl}-amide,

(20) 5-bromo-thiophene-2-carboxylic acid-N-{1-methyl-1-[3-methyl-4-(1-methypiperazin-4-yl-carbonyl)-phenylcarbamoyl]-ethyl}-amide,

(21) 5-bromo-thiophene-2-carboxylic acid-N-{1-methyl-1-[3-methyl-4-(1-methyl-1,4-diazepan-4-yl-carbonyl)-phenylcarbamoyl]-ethyl}-amide,

(22) 5-bromo-thiophene-2-carboxylic acid-N-{(1R)-2-methoxy-1-[3-methyl-4-(pyrrolidin-1-yl-carbonyl)-phenylcarbamoyl]-ethyl}-amide,

(23) 5-bromo-thiophene-2-carboxylic acid-N-{(1S)-2-methoxy-1-[3-methyl-4-(pyrrolidin-1-yl-carbonyl)-phenylcarbamoyl]-ethyl}-amide,

(24) 5-bromo-thiophene-2-carboxylic acid-N-{2-methoxy-1-[3-methyl-4-(pyrrolidin-1-yl-carbonyl)-phenylcarbamoyl]-propyl}-amide,

(25) 5-bromo-thiophene-2-carboxylic acid-N-{3-methylsulphanyl-1-[3-methyl-4-(pyrrolidin-1-yl-carbonyl)-phenylcarbamoyl]-propyl}-amide,

(26) 5-bromo-thiophene-2-carboxylic acid-N-{3-methyl-1-[3-methyl-4-(pyrrolidin-1-yl-carbonyl)-phenylcarbamoyl]-butyl}-amide,

(27) 5-bromo-thiophene-2-carboxylic acid-N-{3-methyloxycarbonyl-1-[3-methyl-4-(pyrrolidin-1-yl-carbonyl)-phenylcarbamoyl]-propyl}-amide,

(28) 5-bromo-thiophene-2-carboxylic acid-N-{3-dimethylaminocarbonyl-1-[3-methyl-4-(pyrrolidin-1-yl-carbonyl)-phenylcarbamoyl]-propyl}-amide,

(29) 5-bromo-thiophene-2-carboxylic acid-N-{2-phenyl-1-[3-methyl-4-(pyrrolidin-1-yl-carbonyl)-phenylcarbamoyl]-ethyl}-amide,

(30) 5-bromo-thiophene-2-carboxylic acid-N-{1-(thiophenyl-3-yl)-1-[3-methyl-4-(pyrrolidin-1-yl-carbonyl)-phenylcarbamoyl]-methyl}-amide,

(31) 5-bromo-thiophene-2-carboxylic acid-N-{5-dimethylamino-1-[3-methyl-4-(pyrrolidin-1-yl-carbonyl)-phenylcarbamoyl]-pentyl}-amide,

(32) 5-bromo-thiophene-2-carboxylic acid-N-{1-[3-methyl-4-(2,2-dimethyl-pyrrolidin-1-yl-carbonyl)-phenylcarbamoyl]-cyclopentyl}-amide,

(33) 5-bromo-thiophene-2-carboxylic acid-N-{1-[3-methyl-4-(pyrrolidin-1-yl-carbonyl)-phenylcarbamoyl]-cyclopentyl}-amide,

(34) 5-bromo-thiophene-2-carboxylic acid-N-{1-[3-methyl-4-(pyrrolidin-1-yl-carbonyl)-phenylcarbamoyl]-cyclohexyl}-amide,

(35) 5-bromo-thiophene-2-carboxylic acid-N-{3-[3-chloro-4-(2-oxo-piperazin-4-yl-carbonyl)-phenylcarbamoyl]-tetrahydrofuran-3-yl}-amide,

(36) 5-bromo-thiophene-2-carboxylic acid-N-{3-[3-chloro-4-(pyrrolidin-1-yl-carbonyl)-phenylcarbamoyl]-tetrahydrofuran-3-yl}-amide,

(37) 5-bromo-thiophene-2-carboxylic acid-N-{4-[3-bromo-4-(2-oxo-piperazin-4-yl-carbonyl)-phenylcarbamoyl]-tetrahydropyran-4-yl}-amide,

(38) 5-bromo-thiophene-2-carboxylic acid-N-{4-[3-bromo-4-(pyrrolidin-1-yl-carbonyl)-phenylcarbamoyl]-tetrahydropyran-4-yl}-amide,

(39) 5-bromo-thiophene-2-carboxylic acid-N-{1-methyl-4-[3-trifluoromethyl-4-(2-oxo-piperazin-4-yl-carbonyl)-phenylcarbamoyl]-piperazin-4-yl}-amide,

(40) 5-bromo-thiophene-2-carboxylic acid-N-{1-methyl-4-[3-chloro-4-(pyrrolidin-1-yl-carbonyl)-phenylcarbamoyl]-piperazin-4-yl}-amide,

(41) 5-bromo-thiophene-2-carboxylic acid-N-{1-[3-methoxy-4-(2-oxo-piperazin-4-yl-carbonyl)-phenylcarbamoyl]-cycloheptyl}-amide,

(42) 5-chloro-thiophene-2-carboxylic acid-N-{(1R)-1-[3-chloro-4-(pyrrolidin-1-yl-carbonyl)-phenylcarbamoyl]-ethyl}-amide,

(43) 5-chloro-thiophene-2-carboxylic acid-N-{2-methoxy-1-[3-methyl-4-(pyrrolidin-1-yl-carbonyl)-phenylcarbamoyl]-ethyl}-amide,

(44) 5-chloro-thiophene-2-carboxylic acid-N-{(1R)-1-phenyl-1-[3-methyl-4-(pyrrolidin-1-yl-carbonyl)-phenylcarbamoyl]-methyl}-amide,

(45) 5-bromo-thiophene-2-carboxylic acid-N-{1-[3-methyl-4-(pyrrolidin-1-yl-carbonyl)-phenylcarbamoyl]-cyclobut-1-yl}-amide,

(46) 5-bromo-thiophene-2-carboxylic acid-N-{1-methyl-1-[4-(pyrrolidin-1-yl-carbonyl)-phenylcarbamoyl]-ethyl}-amide,

(47) 5-bromo-thiophene-2-carboxylic acid-N-{(1R)-2-[1-methyl-1H-imidazol-4-yl]-1-[3-methyl-4-(pyrrolidin-1-yl-carbonyl)-phenylcarbamoyl]-ethyl}-amide,

(48) 5-bromo-thiophene-2-carboxylic acid-N-{(1R)-2-[pyridin-4-yl]-1-[3-methyl-4-(pyrrolidin-1-yl-carbonyl)-phenylcarbamoyl]-ethyl}-amide,

(49) 5-chloro-thiophene-2-carboxylic acid-N-{(1R)-2-[pyridin-4-yl]-1-[3-methyl-4-(pyrrolidin-1-yl-carbonyl)-phenylcarbamoyl]-ethyl}-amide,

(50) 5-bromo-thiophene-2-carboxylic acid-N-{(1R)-2-[1H-imidazol-4-yl]-1-[3-methyl-4-(pyrrolidin-1-yl-carbonyl)-phenylcarbamoyl]-ethyl}-amide,

(51) 5-bromo-thiophene-2-carboxylic acid-N-{3-[3-methyl-4-(pyrrolidin-1-yl-carbonyl)-phenylcarbamoyl]-tetrahydrofuran-3-yl}-amide,

(52) 5-bromo-thiophene-2-carboxylic acid-N-{3-[4-(pyrrolidin-1-yl-carbonyl)-phenylcarbamoyl]-tetrahydrofuran-3-yl}-amide,

(53) 5-bromo-thiophene-2-carboxylic acid-N-{1-[3-methyl-4-(morpholin-4-yl-carbonyl)-phenylcarbamoyl]-cyclopent-1-yl}-amide,

(54) 5-bromo-thiophene-2-carboxylic acid-N-{1-methyl-1-[2-fluoro-4-(pyrrolidin-1-yl-carbonyl)-phenylcarbamoyl]-ethyl}-amide,

(55) 5-bromo-thiophene-2-carboxylic acid-N-{1-methyl-1-[3-methyl-4-((2S)-2-hydroxymethyl-pyrrolidin-1-yl-carbonyl)-phenylcarbamoyl]-ethyl}-amide,

(56) 5-bromo-thiophene-2-carboxylic acid-N-{1-methyl-1-[3-methyl-4-((2S)-2-methoxymethyl-pyrrolidin-1-yl-carbonyl)-phenylcarbamoyl]-ethyl}-amide,

(57) 5-bromo-thiophene-2-carboxylic acid-N-{1-methyl-1-[3-methyl-4-((2S)-2-{pyrrolidin-1-yl-methyl}-pyrrolidin-1-yl-carbonyl)-phenylcarbamoyl]-ethyl}-amide,

(58) 5-bromo-thiophene-2-carboxylic acid-N-{1-methyl-1-[3-methyl-4-(3-oxo-piperazin-1-yl-carbonyl)-phenylcarbamoyl]-ethyl}-amide,

(59) 5-bromo-thiophene-2-carboxylic acid-N-{1-methyl-1-[3-methyl-4-(5-oxo-[1,4]diazepan-1-yl-carbonyl)-phenylcarbamoyl]-ethyl}-amide,

(60) 5-bromo-thiophene-2-carboxylic acid-N-{1-methyl-1-[3-methyl-4-(3-oxo-[1,4]diazepan-1-yl-carbonyl)-phenylcarbamoyl]-ethyl}-amide,

(61) 5-bromo-thiophene-2-carboxylic acid-N-{1-methyl-1-[3-methyl-4-(4-formyl-piperazin-1-yl-carbonyl)-phenylcarbamoyl]-ethyl}-amide,

(62) 5-bromo-thiophene-2-carboxylic acid-N-{1-methyl-1-[3-methyl-4-(4-acetyl-piperazin-1-yl-carbonyl)-phenylcarbamoyl]-ethyl}-amide,

(63) 5-chloro-thiophene-2-carboxylic acid-N-{1-methyl-1-[3-methyl-4-((2S)-2-hydroxymethyl-pyrrolidin-1-yl-carbonyl)-phenylcarbamoyl]-ethyl}-amide,

(64) 5-chloro-thiophene-2-carboxylic acid-N-{1-methyl-1-[3-methyl-4-((2S)-2-methoxymethyl-pyrrolidin-1-yl-carbonyl)-phenylcarbamoyl]-ethyl}-amide,

(65) 5-chloro-thiophene-2-carboxylic acid-N-{1-methyl-1-[3-methyl-4-((2S)-2-{pyrrolidin-1-yl-methyl}-pyrrolidin-1-yl-carbonyl)-phenylcarbamoyl]-ethyl}-amide,

(66) 5-chloro-thiophene-2-carboxylic acid-N-{1-methyl-1-[3-methyl-4-(3-oxo-piperazin-1-yl-carbonyl)-phenylcarbamoyl]-ethyl}-amide,

(67) 5-chloro-thiophene-2-carboxylic acid-N-{1-methyl-1-[3-methyl-4-(5-oxo-[1,4]diazepan-1-yl-carbonyl)-phenylcarbamoyl]-ethyl}-amide,

(68) 5-chloro-thiophene-2-carboxylic acid-N-{1-methyl-1-[3-methyl-4-(3-oxo-[1,4]diazepan-1-yl-carbonyl)-phenylcarbamoyl]-ethyl}-amide,

(69) 5-chloro-thiophene-2-carboxylic acid-N-{1-methyl-1-[3-methyl-4-(4-formyl-piperazin-1-yl-carbonyl)-phenylcarbamoyl]-ethyl}-amide,

(70) 5-chloro-thiophene-2-carboxylic acid-N-{1-methyl-1-[3-methyl-4-(4-acetyl-piperazin-1-yl-carbonyl)-phenylcarbamoyl]-ethyl}-amide,

(71) 5-chloro-thiophene-2-carboxylic acid-N-{1-methyl-1-[3-methyl-4-(2-{3-hydroxy-prop-1-yl}-piperidin-1-yl-carbonyl)-phenylcarbamoyl]-ethyl}-amide,

(72) 5-chloro-thiophene-2-carboxylic acid-N-{1-methyl-1-[3-methyl-4-(1-oxo-thiomorpholin-4-yl-carbonyl)-phenylcarbamoyl]-ethyl}-amide,

(73) 5-chloro-thiophene-2-carboxylic acid-N-{1-methyl-1-[3-methyl-4-((2S,4R)-2-methoxycarbonyl-4-hydroxy-pyrrolidin-1-yl-carbonyl)-phenylcarbamoyl]-ethyl}-amide,

(74) 5-chloro-thiophene-2-carboxylic acid-N-{1-methyl-1-[3-methyl-4-(3,5-dimethyl-piperidin-1-yl-carbonyl)-phenylcarbamoyl]-ethyl}-amide,

(75) 5-chloro-thiophene-2-carboxylic acid-N-{1-methyl-1-[3-methyl-4-(4-aminocarbonyl-piperidin-1-yl-carbonyl)-phenylcarbamoyl]-ethyl}-amide,

(76) 5-chloro-thiophene-2-carboxylic acid-N-{1-methyl-1-[3-methyl-4-(3-methyl-piperidin-1-yl-carbonyl)-phenylcarbamoyl]-ethyl}-amide,

(77) 5-chloro-thiophene-2-carboxylic acid-N-{1-methyl-1-[3-methyl-4-(4-methyl-piperidin-1-yl-carbonyl)-phenylcarbamoyl]-ethyl}-amide,

(78) 5-chloro-thiophene-2-carboxylic acid-N-{1-methyl-1-[3-methyl-4-(3-{3-butyl-ureido}-piperidin-1-yl-carbonyl)-phenylcarbamoyl]-ethyl}-amide,

(79) 5-chloro-thiophene-2-carboxylic acid-N-{1-methyl-1-[3-methyl-4-((2S)-2-{dimethylaminocarbonyl}-pyrrolidin-1-yl-carbonyl)-phenylcarbamoyl]-ethyl}-amide,

(80) 5-chloro-thiophene-2-carboxylic acid-N-{1-methyl-1-[3-methyl-4-((2S)-2-{methylaminocarbonyl}-pyrrolidin-1-yl-carbonyl)-phenylcarbamoyl]-ethyl}-amide,

(81) 5-chloro-thiophene-2-carboxylic acid-N-{1-methyl-1-[3-methyl-4-(2-methoxycarbonyl-piperidin-1-yl-carbonyl)-phenylcarbamoyl]-ethyl}-amide,

(82) 5-chloro-thiophene-2-carboxylic acid-N-{1-methyl-1-[3-methyl-4-((2R)-2-aminocarbonyl-pyrrolidin-1-yl-carbonyl)-phenylcarbamoyl]-ethyl}-amide,

(83) 5-chloro-thiophene-2-carboxylic acid-N-{1-methyl-1-[3-methyl-4-(3-{1-butyl-sulphonylamino}-piperidin-1-yl-carbonyl)-phenylcarbamoyl]-ethyl}-amide,

(84) 5-chloro-thiophene-2-carboxylic acid-N-{1-methyl-1-[3-methyl-4-(4-hydroxy-piperazin-1-yl-carbonyl)-phenylcarbamoyl]-ethyl}-amide,

(85) 5-chloro-thiophene-2-carboxylic acid-N-{1-methyl-1-[3-methyl-4-(2-methoxycarbonyl-pyrrolidin-1-yl-carbonyl)-phenylcarbamoyl]-ethyl}-amide,

(86) 5-chloro-thiophene-2-carboxylic acid-N-{1-methyl-1-[3-methyl-4-(2-{pyridin-3-yl}-piperidin-1-yl-carbonyl)-phenylcarbamoyl]-ethyl}-amide,

(87) 5-chloro-thiophene-2-carboxylic acid-N-{1-methyl-1-[3-methyl-4-(2-{4-dimethylamino-but-1-yl}-piperidin-1-yl-carbonyl)-phenylcarbamoyl]-ethyl}-amide,

(88) 5-chloro-thiophene-2-carboxylic acid-N-{1-methyl-1-[3-methyl-4-((2R)-2-hydroxymethyl-pyrrolidin-1-yl-carbonyl)-phenylcarbamoyl]-ethyl}-amide,

(89) 5-chloro-thiophene-2-carboxylic acid-N-{1-methyl-1-[3-methyl-4-(thiomorpholin-4-yl-carbonyl)-phenylcarbamoyl]-ethyl}-amide,

(90) 5-chloro-thiophene-2-carboxylic acid-N-{1-methyl-1-[3-methyl-4-(2-methyl-morpholin-4-yl-carbonyl)-phenylcarbamoyl]-ethyl}-amide,

(91) 5-chloro-thiophene-2-carboxylic acid-N-{1-methyl-1-[3-methyl-4-((2R)-2-methoxymethyl-pyrrolidin-1-yl-carbonyl)-phenylcarbamoyl]-ethyl}-amide,

(92) 5-chloro-thiophene-2-carboxylic acid-N-{1-methyl-1-[3-methyl-4-(2-{2-diethylamino-eth-1-yl}-piperidin-1-yl-carbonyl)-phenylcarbamoyl]-ethyl}-amide,

(93) 5-chloro-thiophene-2-carboxylic acid-N-{1-methyl-1-[3-methyl-4-(4-methyl-[1,4]diazepan-1-yl-carbonyl)-phenylcarbamoyl]-ethyl}-amide,

(94) 5-chloro-thiophene-2-carboxylic acid-N-{1-methyl-1-[3-methyl-4-(thiazolidin-1-yl-carbonyl)-phenylcarbamoyl]-ethyl}-amide,

(95) 5-chloro-thiophene-2-carboxylic acid-N-{1-methyl-1-[3-methyl-4-(3,6-dihydro-2H-pyridin-1-yl-carbonyl)-phenylcarbamoyl]-ethyl}-amide,

(96) 5-chloro-thiophene-2-carboxylic acid-N-{1-methyl-1-[3-methyl-4-(azepan-1-yl-carbonyl)-phenylcarbamoyl]-ethyl}-amide,

(97) 5-chloro-thiophene-2-carboxylic acid-N-{1-methyl-1-[3-methyl-4-(3,3-dimethyl-piperidin-1-yl-carbonyl)-phenylcarbamoyl]-ethyl}-amide,

(98) 5-chloro-thiophene-2-carboxylic acid-N-{1-methyl-1-[3-methyl-4-(2-ethyl-piperidin-1-yl-carbonyl)-phenylcarbamoyl]-ethyl}-amide,

(99) 5-chloro-thiophene-2-carboxylic acid-N-{1-methyl-1-[3-methyl-4-(3-ethoxycarbonyl-piperidin-1-yl-carbonyl)-phenylcarbamoyl]-ethyl}-amide, (100) 5-chloro-thiophene-2-carboxylic acid-N-{1-methyl-1-[3-methyl-4-(2-{N-ethyl-N-methyl-amino-methyl}-piperidin-1-yl-carbonyl)-phenylcarbamoyl]-ethyl}-amide, (101) 5-chloro-thiophene-2-carboxylic acid-N-{1-methyl-1-[3-methyl-4-(2-{3-dimethylamino-prop-1-yl}-piperidin-1-yl-carbonyl)-phenylcarbamoyl]-ethyl}-amide, (102) 5-chloro-thiophene-2-carboxylic acid-N-{1-methyl-1-[3-methyl-4-(2-{piperidin-1-yl-methyl}-piperidin-1-yl-carbonyl)-phenylcarbamoyl]-ethyl}-amide, (103) 5-chloro-thiophene-2-carboxylic acid-N-{1-methyl-1-[3-methyl-4-(2-{methoxy-carbonyl-methyl}-piperidin-1-yl-carbonyl)-phenylcarbamoyl]-ethyl}-amide, (104) 5-chloro-thiophene-2-carboxylic acid-N-{1-methyl-1-[3-methyl-4-(3-hydroxyl-piperidin-1-yl-carbonyl)-phenylcarbamoyl]-ethyl}-amide, (105) 5-chloro-thiophene-2-carboxylic acid-N-{1-methyl-1-[3-methyl-4-(4-methoxy-piperidin-1-yl-carbonyl)-phenylcarbamoyl]-ethyl}-amide, (106) 5-chloro-thiophene-2-carboxylic acid-N-{1-methyl-1-[3-methyl-4-(2-methyl-pyrrolidin-1-yl-carbonyl)-phenylcarbamoyl]-ethyl}-amide, (107) 5-chloro-thiophene-2-carboxylic acid-N-{1-methyl-1-[3-methyl-4-((2R)-2-{phenylamino-methyl}-pyrrolidin-1-yl-carbonyl)-phenylcarbamoyl]-ethyl}-amide, (108) 5-chloro-thiophene-2-carboxylic acid-N-{1-methyl-1-[3-methyl-4-(4-methyl-piperazin-1-yl-carbonyl)-phenylcarbamoyl]-ethyl}-amide, (109) 5-chloro-thiophene-2-carboxylic acid-N-{1-methyl-1-[3-methyl-4-(piperidin-1-yl-carbonyl)-phenylcarbamoyl]-ethyl}-amide, (110) 5-chloro-thiophene-2-carboxylic acid-N-{1-methyl-1-[3-methyl-4-(2-methyl-piperidin-1-yl-carbonyl)-phenylcarbamoyl]-ethyl}-amide, (111) 5-chloro-thiophene-2-carboxylic acid-N-{1-methyl-1-[3-methyl-4-(3-aminocarbonyl-piperidin-1-yl-carbonyl)-phenylcarbamoyl]-ethyl}-amide, (112) 5-chloro-thiophene-2-carboxylic acid-N-{1-methyl-1-[3-methyl-4-(4-hydroxyl-piperidin-1-yl-carbonyl)-phenylcarbamoyl]-ethyl}-amide, (113) 5-chloro-thiophene-2-carboxylic acid-N-{1-methyl-1-[3-methyl-4-(morpholin-4-yl-carbonyl)-phenylcarbamoyl]-ethyl}-amide, (114) 5-chloro-thiophene-2-carboxylic acid-N-{1-methyl-1-[3-methyl-4-(2-methyl-4-phenyl-pyrrolidin-1-yl-carbonyl)-phenylcarbamoyl]-ethyl}-amide, (115) 5-chloro-thiophene-2-carboxylic acid-N-{1-methyl-1-[3-methyl-4-(2,5-dimethyl-pyrrolidin-1-yl-carbonyl)-phenylcarbamoyl]-ethyl}-amide, (116) 5-chloro-thiophene-2-carboxylic acid-N-{1-methyl-1-[3-methyl-4-(3-dimethylamino-pyrrolidin-1-yl-carbonyl)-phenylcarbamoyl]-ethyl}-amide, (117) 5-chloro-thiophene-2-carboxylic acid-N-{1-methyl-1-[3-methyl-4-(3-{4-diethylamino-but-1-yl}-piperidin-1-yl-carbonyl)-phenylcarbamoyl]-ethyl}-amide, (118) 5-chloro-thiophene-2-carboxylic acid-N-{1-methyl-1-[3-methyl-4-(4-{dimethylamino-methyl}-piperidin-1-yl-carbonyl)-phenylcarbamoyl]-ethyl}-amide, (119) 5-chloro-thiophene-2-carboxylic acid-N-{1-methyl-1-[3-methyl-4-(2-{pyridin-2-yl}-pyrrolidin-1-yl-carbonyl)-phenylcarbamoyl]-ethyl}-amide, (120) 5-chloro-thiophene-2-carboxylic acid-N-{1-methyl-1-[3-methyl-4-(2-{pyridin-4-yl}-pyrrolidin-1-yl-carbonyl)-phenylcarbamoyl]-ethyl}-amide, (121) 5-chloro-thiophene-2-carboxylic acid-N-{1-methyl-1-[3-methyl-4-((2S)-2-{phenylamino-methyl}-pyrrolidin-1-yl-carbonyl)-phenylcarbamoyl]-ethyl}-amide, (122) 5-chloro-thiophene-2-carboxylic acid-N-{1-[3-methyl-4-(4-ethyl-piperazin-1-yl-carbonyl)-phenylcarbamoyl]-ethyl}-amide, (123) 5-chloro-thiophene-2-carboxylic acid-N-{3-[3-methyl-4-((2S)-2-hydroxymethyl-pyrrolidin-1-yl-carbonyl)-phenylcarbamoyl]-tetrahydrofuran-3-yl}-amide, (124) 5-chloro-thiophene-2-carboxylic acid-N-{3-[3-methyl-4-((2S)-2-{pyrrolidin-1-yl-methyl}-pyrrolidin-1-yl-carbonyl)-phenylcarbamoyl]-tetrahydrofuran-3-yl}-amide, (125) 5-chloro-thiophene-2-carboxylic acid-N-{3-[3-methyl-4-(3-oxo-piperazin-1-yl-carbonyl)-phenylcarbamoyl]-tetrahydrofuran-3-yl}-amide, (126) 5-chloro-thiophene-2-carboxylic acid-N-{3-[3-methyl-4-(5-oxo-[1,4]diazepan-1-yl-carbonyl)-phenylcarbamoyl]-tetrahydrofuran-3-yl}-amide, (127) 5-chloro-thiophene-2-carboxylic acid-N-{3-[3-methyl-4-(3-oxo-[1,4]diazepan-1-yl-carbonyl)-phenylcarbamoyl]-tetrahydrofuran-3-yl}-amide, (128) 5-chloro-thiophene-2-carboxylic acid-N-{3-[3-methyl-4-(4-formyl-piperazin-1-yl-carbonyl)-phenylcarbamoyl]-tetrahydrofuran-3-yl}-amide, (129) 5-chloro-thiophene-2-carboxylic acid-N-{3-[3-methyl-4-(4-acetyl-piperazin-1-yl-carbonyl)-phenylcarbamoyl]-tetrahydrofuran-3-yl}-amide, (130) 5-bromo-thiophene-2-carboxylic acid-N-{3-[3-methyl-4-((2S)-2-hydroxymethyl-pyrrolidin-1-yl-carbonyl)-phenylcarbamoyl]-tetrahydrofuran-3-yl}-amide, (131) 5-bromo-thiophene-2-carboxylic acid-N-{3-[3-methyl-4-((2S)-2-{pyrrolidin-1-yl-methyl}-pyrrolidin-1-yl-carbonyl)-phenylcarbamoyl]-tetrahydrofuran-3-yl}-amide, (132) 5-bromo-thiophene-2-carboxylic acid-N-{3-[3-methyl-4-(3-oxo-piperazin-1-yl-carbonyl)-phenylcarbamoyl]-tetrahydrofuran-3-yl}-amide, (133) 5-bromo-thiophene-2-carboxylic acid-N-{3-[3-methyl-4-(5-oxo-[1,4]diazepan-1-yl-carbonyl)-phenylcarbamoyl]-tetrahydrofuran-3-yl}-amide, (134) 5-bromo-thiophene-2-carboxylic acid-N-{3-[3-methyl-4-(3-oxo-[1,4]diazepan-1-yl-carbonyl)-phenylcarbamoyl]-tetrahydrofuran-3-yl}-amide, (135) 5-bromo-thiophene-2-carboxylic acid-N-{3-[3-methyl-4-(4-formyl-piperazin-1-yl-carbonyl)-phenylcarbamoyl]-tetrahydrofuran-3-yl}-amide, (136) 5-bromo-thiophene-2-carboxylic acid-N-{3-[3-methyl-4-(4-acetyl-piperazin-1-yl-carbonyl)-phenylcarbamoyl]-tetrahydrofuran-3-yl}-amide, (137) 5-bromo-thiophene-2-carboxylic acid-N-{2-[3-chloro-4-((2S)-2-{pyrrolidin-1-yl-methyl}-pyrrolidin-1-yl-carbonyl)-phenylcarbamoyl]-bicyclo[2.2.1]hept-2-yl}-amide, (138) 5-chloro-thiophene-2-carboxylic acid-N-{3-[3-chloro-4-(3-oxo-piperazin-1-yl-carbonyl)-phenylcarbamoyl]-tetrahydrofuran-3-yl}-amide, (139) 5-chloro-thiophene-2-carboxylic acid-N-{2-[3-methyl-4-(5-oxo-[1,4]diazepan-1-yl-carbonyl)-phenylcarbamoyl]-7-oxa-bicyclo[2.2.1]hept-2-yl}-amide, (140) 5-chloro-thiophene-2-carboxylic acid-N-{2-[3-methyl-4-(3-oxo-[1,4]diazepan-1-yl-carbonyl)-phenylcarbamoyl]-bicyclo[2.2.1]hept-2-yl}-amide, (141) 5-chloro-thiophene-2-carboxylic acid-N-{2-[4-(4-formyl-piperazin-1-yl-carbonyl)-phenylcarbamoyl]-7-oxa-bicyclo[2.2.1]hept-2-yl}-amide, (142) 5-chloro-thiophene-2-carboxylic acid-N-{2-[3-chloro-4-(4-acetyl-piperazin-1-yl-carbonyl)-phenylcarbamoyl]-7-oxa-bicyclo[2.2.1]hept-2-yl}-amide, the tautomers, the enantiomers, the diastereomers, the mixtures thereof and the salts thereof, while the compounds (1) 5-chloro-thiophene-2-carboxylic acid-N-{1-[3-chloro-4-(pyrrolidin-1-yl-carbonyl)-phenylcarbamoyl]-ethyl}-amide, (2) 5-chloro-thiophene-2-carboxylic acid-N-{(1R)-2-methoxy-1-[3-methyl-4-(pyrrolidin-1-yl-carbonyl)-phenylcarbamoyl]-ethyl}-amide, (3) 5-chloro-thiophene-2-carboxylic acid-N-{(1S)-2-methoxy-1-[3-methyl-4-(pyrrolidin-1-yl-carbonyl)-phenylcarbamoyl]-ethyl}-amide, (4) 5-bromo-thiophene-2-carboxylic acid-N-{(1R)-2-methoxy-1-methyl-1-[3-methyl-4-(pyrrolidin-1-yl-carbonyl)-phenylcarbamoyl]-ethyl}-amide, (5) 5-bromo-thiophene-2-carboxylic acid-N-{(1S)-2-methoxy-1-methyl-1-[3-methyl-4-(pyrrolidin-1-yl-carbonyl)-phenylcarbamoyl]-ethyl}-amide, (6) 5-bromo-thiophene-2-carboxylic acid-N-{1-methyl-1-[3-methyl-4-(pyrrolidin-1-yl-carbonyl)-phenylcarbamoyl]-ethyl}-amide, (7) 5-chloro-thiophene-2-carboxylic acid-N-{1-methyl-1-[3-methyl-4-(pyrrolidin-1-yl-carbonyl)-phenylcarbamoyl]-ethyl}-amide, (8) 5-bromo-thiophene-2-carboxylic acid-N-{1-methyl-1-[3-chloro-4-(pyrrolidin-1-yl-carbonyl)-phenylcarbamoyl]-ethyl}-amide, (9) 5-chloro-thiophene-2-carboxylic acid-N-{1-methyl-1-[3-chloro-4-(pyrrolidin-1-yl-carbonyl)-phenylcarbamoyl]-ethyl}-amide,

(10) 5-bromo-thiophene-2-carboxylic acid-N-{1-methyl-1-[3-bromo-4-(pyrrolidin-1-yl-carbonyl)-phenylcarbamoyl]-ethyl}-amide,

(11) 5-chloro-thiophene-2-carboxylic acid-N-{1-methyl-1-[3-bromo-4-(pyrrolidin-1-yl-carbonyl)-phenylcarbamoyl]-ethyl}-amide,

(12) 5-bromo-thiophene-2-carboxylic acid-N-{1-methyl-1-[3-methyl-4-(2-dimethylaminomethylpyrrolidin-1-yl-carbonyl)-phenylcarbamoyl]-ethyl}-amide,

(13) 5-bromo-thiophene-2-carboxylic acid-N-{1-methyl-1-[3-methyl-4-(2-methylpyrrolidin-1-yl-carbonyl)-phenylcarbamoyl]-ethyl}-amide,

(14) 5-bromo-thiophene-2-carboxylic acid-N-{1-methyl-1-[3-methyl-4-(piperidin-1-yl-carbonyl)-phenylcarbamoyl]-ethyl}-amide,

(15) 5-bromo-thiophene-2-carboxylic acid-N-{1-methyl-1-[3-methyl-4-(morpholin-4-yl-carbonyl)-phenylcarbamoyl]-ethyl}-amide,

(16) 5-bromo-thiophene-2-carboxylic acid-N-{1-methyl-1-[3-chloro-4-(morpholin-4-yl-carbonyl)-phenylcarbamoyl]-ethyl}-amide,

(17) 5-bromo-thiophene-2-carboxylic acid-N-{1-methyl-1-[3-methyl-4-(1-methypiperazin-4-yl-carbonyl)-phenylcarbamoyl]-ethyl}-amide,

(18) 5-bromo-thiophene-2-carboxylic acid-N-{1-methyl-1-[3-methyl-4-(1-methyl-1,4-diazepan-4-yl-carbonyl)-phenylcarbamoyl]-ethyl}-amide,

(19) 5-bromo-thiophene-2-carboxylic acid-N-{(1R)-2-methoxy-1-[3-methyl-4-(pyrrolidin-1-yl-carbonyl)-phenylcarbamoyl]-ethyl}-amide,

(20) 5-bromo-thiophene-2-carboxylic acid-N-{(1S)-2-methoxy-1-[3-methyl-4-(pyrrolidin-1-yl-carbonyl)-phenylcarbamoyl]-ethyl}-amide,

(21) 5-bromo-thiophene-2-carboxylic acid-N-{2-methoxy-1-[3-methyl-4-(pyrrolidin-1-yl-carbonyl)-phenylcarbamoyl]-propyl}-amide,

(22) 5-bromo-thiophene-2-carboxylic acid-N-{3-methyl-1-[3-methyl-4-(pyrrolidin-1-yl-carbonyl)-phenylcarbamoyl]-butyl}-amide,

(23) 5-bromo-thiophene-2-carboxylic acid-N-{3-methyloxycarbonyl-1-[3-methyl-4-(pyrrolidin-1-yl-carbonyl)-phenylcarbamoyl]-propyl}-amide,

(24) 5-bromo-thiophene-2-carboxylic acid-N-{3-dimethylaminocarbonyl-1-[3-methyl-4-(pyrrolidin-1-yl-carbonyl)-phenylcarbamoyl]-propyl}-amide,

(25) 5-bromo-thiophene-2-carboxylic acid-N-{2-phenyl-1-[3-methyl-4-(pyrrolidin-1-yl-carbonyl)-phenylcarbamoyl]-ethyl}-amide,

(26) 5-bromo-thiophene-2-carboxylic acid-N-{1-(thiophenyl-3-yl)-1-[3-methyl-4-(pyrrolidin-1-yl-carbonyl)-phenylcarbamoyl]-methyl}-amide,

(27) 5-bromo-thiophene-2-carboxylic acid-N-{5-dimethylamino-1-[3-methyl-4-(pyrrolidin-1-yl-carbonyl)-phenylcarbamoyl]-pentyl}-amide,

(28) 5-bromo-thiophene-2-carboxylic acid-N-{1-[3-methyl-4-(pyrrolidin-1-yl-carbonyl)-phenylcarbamoyl]-cyclopentyl}-amide,

(29) 5-bromo-thiophene-2-carboxylic acid-N-{1-[3-methyl-4-(pyrrolidin-1-yl-carbonyl)-phenylcarbamoyl]-cyclohexyl}-amide,

(30) 5-bromo-thiophene-2-carboxylic acid-N-{3-[3-chloro-4-(2-oxo-piperazin-4-yl-carbonyl)-phenylcarbamoyl]-tetrahydrofuran-3-yl}-amide,

(31) 5-bromo-thiophene-2-carboxylic acid-N-{3-[3-chloro-4-(pyrrolidin-1-yl-carbonyl)-phenylcarbamoyl]-tetrahydrofuran-3-yl}-amide,

(32) 5-bromo-thiophene-2-carboxylic acid-N-{4-[3-bromo-4-(2-oxo-piperazin-4-yl-carbonyl)-phenylcarbamoyl]-tetrahydropyran-4-yl}-amide,

(33) 5-bromo-thiophene-2-carboxylic acid-N-{4-[3-bromo-4-(pyrrolidin-1-yl-carbonyl)-phenylcarbamoyl]-tetrahydropyran-4-yl}-amide,

(34) 5-bromo-thiophene-2-carboxylic acid-N-{1-methyl-4-[3-chloro-4-(pyrrolidin-1-yl-carbonyl)-phenylcarbamoyl]-piperazin-4-yl}-amide,

(35) 5-chloro-thiophene-2-carboxylic acid-N-{(1R)-1-[3-chloro-4-(pyrrolidin-1-yl-carbonyl)-phenylcarbamoyl]-ethyl}-amide,

(36) 5-chloro-thiophene-2-carboxylic acid-N-{2-methoxy-1-[3-methyl-4-(pyrrolidin-1-yl-carbonyl)-phenylcarbamoyl]-ethyl}-amide,

(37) 5-chloro-thiophene-2-carboxylic acid-N-{(1R)-1-phenyl-1-[3-methyl-4-(pyrrolidin-1-yl-carbonyl)-phenylcarbamoyl]-methyl}-amide,

(38) 5-bromo-thiophene-2-carboxylic acid-N-{1-[3-methyl-4-(pyrrolidin-1-yl-carbonyl)-phenylcarbamoyl]-cyclobut-1-yl}-amide,

(39) 5-bromo-thiophene-2-carboxylic acid-N-{1-methyl-1-[4-(pyrrolidin-1-yl-carbonyl)-phenylcarbamoyl]-ethyl}-amide,

(40) 5-bromo-thiophene-2-carboxylic acid-N-{(1R)-2-[1-methyl-1H-imidazol-4-yl]-1-[3-methyl-4-(pyrrolidin-1-yl-carbonyl)-phenylcarbamoyl]-ethyl}-amide,

(41) 5-bromo-thiophene-2-carboxylic acid-N-{(1R)-2-[pyridin-4-yl]-1-[3-methyl-4-(pyrrolidin-1-yl-carbonyl)-phenylcarbamoyl]-ethyl}-amide,

(42) 5-chloro-thiophene-2-carboxylic acid-N-{(1R)-2-[pyridin-4-yl]-1-[3-methyl-4-(pyrrolidin-1-yl-carbonyl)-phenylcarbamoyl]-ethyl}-amide,

(43) 5-bromo-thiophene-2-carboxylic acid-N-{(1R)-2-[1H-imidazol-4-yl]-1-[3-methyl-4-(pyrrolidin-1-yl-carbonyl)-phenylcarbamoyl]-ethyl}-amide,

(44) 5-bromo-thiophene-2-carboxylic acid-N-{3-[3-methyl-4-(pyrrolidin-1-yl-carbonyl)-phenylcarbamoyl]-tetrahydrofuran-3-yl}-amide,

(45) 5-bromo-thiophene-2-carboxylic acid-N-{3-[4-(pyrrolidin-1-yl-carbonyl)-phenylcarbamoyl]-tetrahydrofuran-3-yl}-amide,

(46) 5-bromo-thiophene-2-carboxylic acid-N-{1-[3-methyl-4-(morpholin-4-yl-carbonyl)-phenylcarbamoyl]-cyclopent-1-yl}-amide,

(47) 5-bromo-thiophene-2-carboxylic acid-N-{1-methyl-1-[2-fluoro-4-(pyrrolidin-1-yl-carbonyl)-phenylcarbamoyl]-ethyl}-amide,

(48) 5-bromo-thiophene-2-carboxylic acid-N-{1-methyl-1-[3-methyl-4-((2S)-2-hydroxymethyl-pyrrolidin-1-yl-carbonyl)-phenylcarbamoyl]-ethyl}-amide,

(49) 5-bromo-thiophene-2-carboxylic acid-N-{1-methyl-1-[3-methyl-4-((2S)-2-methoxymethyl-pyrrolidin-1-yl-carbonyl)-phenylcarbamoyl]-ethyl}-amide,

(50) 5-bromo-thiophene-2-carboxylic acid-N-{1-methyl-1-[3-methyl-4-((2S)-2-{pyrrolidin-1-yl-methyl}-pyrrolidin-1-yl-carbonyl)-phenylcarbamoyl]-ethyl}-amide,

(51) 5-bromo-thiophene-2-carboxylic acid-N-{1-methyl-1-[3-methyl-4-(3-oxo-piperazin-1-yl-carbonyl)-phenylcarbamoyl]-ethyl}-amide,

(52) 5-bromo-thiophene-2-carboxylic acid-N-{1-methyl-1-[3-methyl-4-(5-oxo-[1,4]diazepan-1-yl-carbonyl)-phenylcarbamoyl]-ethyl}-amide,

(53) 5-bromo-thiophene-2-carboxylic acid-N-{1-methyl-1-[3-methyl-4-(3-oxo-[1,4]diazepan-1-yl-carbonyl)-phenylcarbamoyl]-ethyl}-amide,

(54) 5-bromo-thiophene-2-carboxylic acid-N-{1-methyl-1-[3-methyl-4-(4-formyl-piperazin-1-yl-carbonyl)-phenylcarbamoyl]-ethyl}-amide,

(55) 5-bromo-thiophene-2-carboxylic acid-N-{1-methyl-1-[3-methyl-4-(4-acetyl-piperazin-1-yl-carbonyl)-phenylcarbamoyl]-ethyl}-amide,

(56) 5-chloro-thiophene-2-carboxylic acid-N-{1-methyl-1-[3-methyl-4-((2S)-2-hydroxymethyl-pyrrolidin-1-yl-carbonyl)-phenylcarbamoyl]-ethyl}-amide,

(57) 5-chloro-thiophene-2-carboxylic acid-N-{1-methyl-1-[3-methyl-4-((2S)-2-methoxymethyl-pyrrolidin-1-yl-carbonyl)-phenylcarbamoyl]-ethyl}-amide,

(58) 5-chloro-thiophene-2-carboxylic acid-N-{1-methyl-1-[3-methyl-4-((2S)-2-{pyrrolidin-1-yl-methyl}-pyrrolidin-1-yl-carbonyl)-phenylcarbamoyl]-ethyl}-amide,

(59) 5-chloro-thiophene-2-carboxylic acid-N-{1-methyl-1-[3-methyl-4-(3-oxo-piperazin-1-yl-carbonyl)-phenylcarbamoyl]-ethyl}-amide,

(60) 5-chloro-thiophene-2-carboxylic acid-N-{1-methyl-1-[3-methyl-4-(5-oxo-[1,4]diazepan-1-yl-carbonyl)-phenylcarbamoyl]-ethyl}-amide,

(61) 5-chloro-thiophene-2-carboxylic acid-N-{1-methyl-1-[3-methyl-4-(3-oxo-[1,4]diazepan-1-yl-carbonyl)-phenylcarbamoyl]-ethyl}-amide,

(62) 5-chloro-thiophene-2-carboxylic acid-N-{1-methyl-1-[3-methyl-4-(4-formyl-piperazin-1-yl-carbonyl)-phenylcarbamoyl]-ethyl}-amide,

(63) 5-chloro-thiophene-2-carboxylic acid-N-{1-methyl-1-[3-methyl-4-(4-acetyl-piperazin-1-yl-carbonyl)-phenylcarbamoyl]-ethyl}-amide,

(64) 5-chloro-thiophene-2-carboxylic acid-N-{1-methyl-1-[3-methyl-4-(thiomorpholin-4-yl-carbonyl)-phenylcarbamoyl]-ethyl}-amide,

(65) 5-chloro-thiophene-2-carboxylic acid-N-{1-methyl-1-[3-methyl-4-(thiazolidin-1-yl-carbonyl)-phenylcarbamoyl]-ethyl}-amide,

(66) 5-chloro-thiophene-2-carboxylic acid-N-{1-methyl-1-[3-methyl-4-(3,6-dihydro-2H-pyridin-1-yl-carbonyl)-phenylcarbamoyl]-ethyl}-amide,

(67) 5-chloro-thiophene-2-carboxylic acid-N-{1-methyl-1-[3-methyl-4-(azepan-1-yl-carbonyl)-phenylcarbamoyl]-ethyl}-amide,

(68) 5-chloro-thiophene-2-carboxylic acid-N-{1-methyl-1-[3-methyl-4-(2-methyl-pyrrolidin-1-yl-carbonyl)-phenylcarbamoyl]-ethyl}-amide,

(69) 5-chloro-thiophene-2-carboxylic acid-N-{1-methyl-1-[3-methyl-4-(piperidin-1-yl-carbonyl)-phenylcarbamoyl]-ethyl}-amide,

(70) 5-chloro-thiophene-2-carboxylic acid-N-{1-methyl-1-[3-methyl-4-(morpholin-4-yl-carbonyl)-phenylcarbamoyl]-ethyl}-amide,

(71) 5-chloro-thiophene-2-carboxylic acid-N-{1-methyl-1-[3-methyl-4-(2-{pyridin-4-yl}-pyrrolidin-1-yl-carbonyl)-phenylcarbamoyl]-ethyl}-amide,

(72) 5-chloro-thiophene-2-carboxylic acid-N-{1-methyl-1-[3-methyl-4-((2S)-2-{phenylamino-methyl}-pyrrolidin-1-yl-carbonyl)-phenylcarbamoyl]-ethyl}-amide,

(73) 5-chloro-thiophene-2-carboxylic acid-N-{3-[3-methyl-4-((2S)-2-hydroxymethyl-pyrrolidin-1-yl-carbonyl)-phenylcarbamoyl]-tetrahydrofuran-3-yl}-amide,

(74) 5-chloro-thiophene-2-carboxylic acid-N-{3-[3-methyl-4-((2S)-2-{pyrrolidin-1-yl-methyl}-pyrrolidin-1-yl-carbonyl)-phenylcarbamoyl]-tetrahydrofuran-3-yl}-amide,

(75) 5-chloro-thiophene-2-carboxylic acid-N-{3-[3-methyl-4-(3-oxo-piperazin-1-yl-carbonyl)-phenylcarbamoyl]-tetrahydrofuran-3-yl}-amide,

(76) 5-chloro-thiophene-2-carboxylic acid-N-{3-[3-methyl-4-(5-oxo-[1,4]diazepan-1-yl-carbonyl)-phenylcarbamoyl]-tetrahydrofuran-3-yl}-amide,

(77) 5-chloro-thiophene-2-carboxylic acid-N-{3-[3-methyl-4-(3-oxo-[1,4]diazepan-1-yl-carbonyl)-phenylcarbamoyl]-tetrahydrofuran-3-yl}-amide,

(78) 5-chloro-thiophene-2-carboxylic acid-N-{3-[3-methyl-4-(4-formyl-piperazin-1-yl-carbonyl)-phenylcarbamoyl]-tetrahydrofuran-3-yl}-amide,

(79) 5-chloro-thiophene-2-carboxylic acid-N-{3-[3-methyl-4-(4-acetyl-piperazin-1-yl-carbonyl)-phenylcarbamoyl]-tetrahydrofuran-3-yl}-amide,

(80) 5-bromo-thiophene-2-carboxylic acid-N-{3-[3-methyl-4-((2S)-2-hydroxymethyl-pyrrolidin-1-yl-carbonyl)-phenylcarbamoyl]-tetrahydrofuran-3-yl}-amide,

(81) 5-bromo-thiophene-2-carboxylic acid-N-{3-[3-methyl-4-((2S)-2-{pyrrolidin-1-yl-methyl}-pyrrolidin-1-yl-carbonyl)-phenylcarbamoyl]-tetrahydrofuran-3-yl}-amide,

(82) 5-bromo-thiophene-2-carboxylic acid-N-{3-[3-methyl-4-(3-oxo-piperazin-1-yl-carbonyl)-phenylcarbamoyl]-tetrahydrofuran-3-yl}-amide,

(83) 5-bromo-thiophene-2-carboxylic acid-N-{3-[3-methyl-4-(5-oxo-[1,4]diazepan-1-yl-carbonyl)-phenylcarbamoyl]-tetrahydrofuran-3-yl}-amide,

(84) 5-bromo-thiophene-2-carboxylic acid-N-{3-[3-methyl-4-(3-oxo-[1,4]diazepan-1-yl-carbonyl)-phenylcarbamoyl]-tetrahydrofuran-3-yl}-amide,

(85) 5-bromo-thiophene-2-carboxylic acid-N-{3-[3-methyl-4-(4-formyl-piperazin-1-yl-carbonyl)-phenylcarbamoyl]-tetrahydrofuran-3-yl}-amide,

(86) 5-bromo-thiophene-2-carboxylic acid-N-{3-[3-methyl-4-(4-acetyl-piperazin-1-yl-carbonyl)-phenylcarbamoyl]-tetrahydrofuran-3-yl}-amide,

(87) 5-bromo-thiophene-2-carboxylic acid-N-{2-[3-chloro-4-((2S)-2-{pyrrolidin-1-yl-methyl}-pyrrolidin-1-yl-carbonyl)-phenylcarbamoyl]-bicyclo[2.2.1]hept-2-yl}-amide,

(88) 5-chloro-thiophene-2-carboxylic acid-N-{3-[3-chloro-4-(3-oxo-piperazin-1-yl-carbonyl)-phenylcarbamoyl]-tetrahydrofuran-3-yl}-amide,

(89) 5-chloro-thiophene-2-carboxylic acid-N-{2-[3-methyl-4-(5-oxo-[1,4]diazepan-1-yl-carbonyl)-phenylcarbamoyl]-7-oxa-bicyclo[2.2.1]hept-2-yl}-amide,

(90) 5-chloro-thiophene-2-carboxylic acid-N-{2-[3-methyl-4-(3-oxo-[1,4]diazepan-1-yl-carbonyl)-phenylcarbamoyl]-bicyclo[2.2.1]hept-2-yl}-amide,

(91) 5-chloro-thiophene-2-carboxylic acid-N-{2-[4-(4-formyl-piperazin-1-yl-carbonyl)-phenylcarbamoyl]-7-oxa-bicyclo[2.2.1]hept-2-yl}-amide,

(92) 5-chloro-thiophene-2-carboxylic acid-N-{2-[3-chloro-4-(4-acetyl-piperazin-1-yl-carbonyl)-phenylcarbamoyl]-7-oxa-bicyclo[2.2.1]hept-2-yl}-amide, the tautomers, the enantiomers, the diastereomers, the mixtures thereof and the salts thereof are particularly preferred.

According to the invention the compounds of general formula I are obtained by methods known per se, for example by the following methods:

1) In order to prepare compounds of general formula (I)

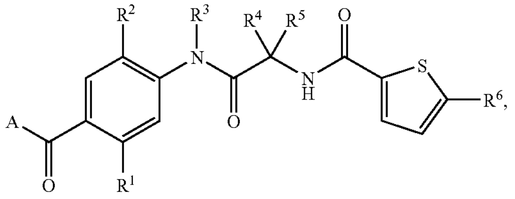

wherein A and $R^1$ to $R^6$ are as hereinbefore defined:

i) acylation of a compound of general formula $Z^1$-H (II)

with a compound of general formula (III)

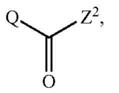

while the following combinations of options for general formulae (II) and (III) result in compounds of general formula (I), and also result in the definitions of $Z^1$ and $Z^2$ for the particular combinations:

a)

(IIa)

$Z^{1a}$—H = A—H and (IIIa)

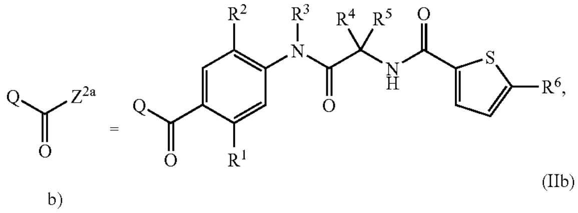

b)

(IIb)

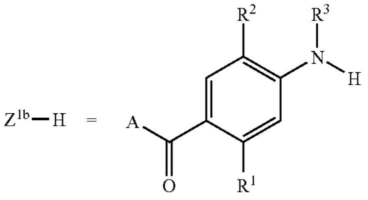

and (IIIb)

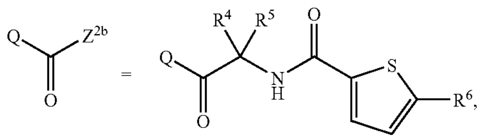

or c)

(IIc)

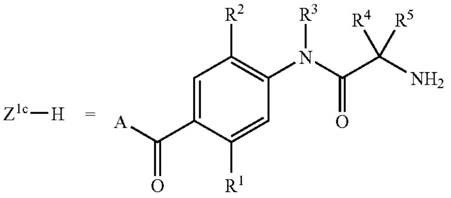

and (IIIc)

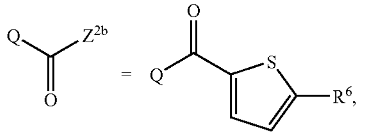

while in the above general formulae A and $R^1$ to $R^6$ are as hereinbefore defined and Q denotes a hydroxy or $C_{1-4}$-alkoxy group, a halogen atom or an acyloxy group.

The acylation is conveniently carried out with a corresponding halide or anhydride in a solvent such as methylene chloride, chloroform, carbon tetrachloride, ether, tetrahydrofuran, dioxane, benzene, toluene, acetonitrile, dimethylformamide, sodium hydroxide solution or sulpholane, optionally in the presence of an inorganic or organic base at temperatures between −20 and 200° C., but preferably at temperatures between −10 and 160° C.

The acylation may however also be carried out with the free acid, optionally in the presence of an acid-activating agent or a dehydrating agent, e.g. in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazole, N,N'-carbonyldiimidazole, O-(benzotriazol- 1-yl)-N,N,N',N'-tetramethyl-uronium tetrafluoroborate/N-methylmorpholine, O-(benzotriazol-1-yl)-N,N,N',N'-tetramethyl-uronium tetrafluoroborate/N-ethyldiisopropylamine, O-pentafluorophenyl-N,N,N',N'-tetramethyluronium-hexafluorophosphate/triethylamine, N,N'-thionyldiimidazole or triphenylphosphine/carbon tetrachloride, at temperatures between −20 and 200° C., but preferably at temperatures between −10 and 160° C.

ii) acylation of a compound of general formula (IIb), wherein A and $R^1$ to $R^3$ are as defined above, with a reactive carboxylic acid derivative of general formula (IX)

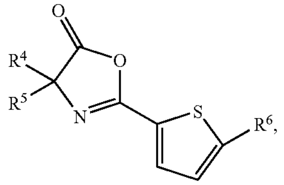

wherein $R^4$ to $R^6$ are as defined above.

The acylation is conveniently carried out in a solvent or mixture of solvents such as dichloromethane, trichloromethan, carbon tetrachloride, benzene, chlorobenzene, toluene, xylene, hexamethyldisiloxane, ether, tetrahydrofuran, dioxane, acetonitrile, N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, optionally in the presence of a Lewis acid such as aluminium chloride, zinc iodide, zinc chloride, boron trifluoride, titanium(IV)chloride or trimethylaluminium at temperatures between −20 and 200° C., but preferably at temperatures between −10 and 160° C., for example using a microwave oven.

Compounds of general formula (XXIII) may conveniently be prepared from compounds of general formula (XXII) in a solvent or mixture of solvents such as dichloromethane, trichloromethan, carbon tetrachloride, benzene, chlorobenzene, toluene, xylene, hexamethyldisiloxan, ether, tetrahydrofuran, dioxane, acetonitrile, pyridine, optionally in the presence of N,N'-dicyclohexylcarbodiimide, N,N'-dicyclohexylcarbodiimide/N-hydroxysuccinimide or 1-hydroxybenzotriazole, N,N'-carbonyldiimidazole, O-(benzotriazol-1-yl)-N,N,N',N'-tetramethyl-uronium tetrafluoroborate/N-methylmorpholine, O-(benzotriazol-1-yl)-N,N,N',N'-tetramethyl-uronium tetrafluoroborate/N-ethyldiisopropylamine, or in a solvent or mixture of solvents such as dichloromethane, trichloromethane, carbon tetrachloride, benzene, chlorobenzene, toluene, xylene, hexamethyldisiloxane, ether, tetrahydrofuran, dioxane, acetonitrile, formic acid, acetic acid, acetic anhydride or propionic acid, at temperatures between −20 and 200° C., but preferably at temperatures between −10 and 160° C.

Other methods of amide coupling are described for example in P. D. Bailey, I. D. Collier, K. M. Morgan in "Comprehensive Functional Group Interconversions", Vol. 5, page 257ff., Pergamon 1995.

2) In order to prepare compounds of general formula (IIb):

a) Acylation of compounds of general formula

A—H (IIa)

with compounds of general formula (IV)

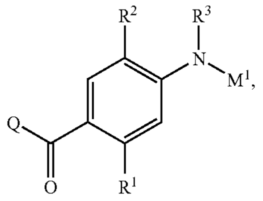

where A and $R^1$ to $R^3$ are as hereinbefore defined, Q denotes a hydroxy or $C_{1-4}$-alkoxy group, a halogen atom or an acyloxy group, and $M^1$ denotes a protective group which is optionally subsequently cleaved.

The acylation is carried out as described for the cases shown in 1)i).

b) Acylation of compounds of general formula

A—H (IIa)

with compounds of general formula (V)

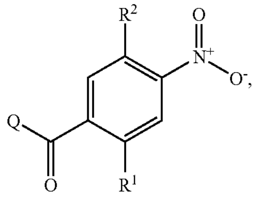

followed by reduction of the nitro group and optionally reductive amination in order to introduce an alkyl group for $R^3$, while A and $R^1$ to $R^3$ are as hereinbefore defined, Q denotes a hydroxy or $C_{1-4}$-alkoxy group, a halogen atom or an acyloxy group, and $M^1$ denotes a protective group which is subsequently cleaved.

The acylation is carried out as described for the cases shown in 1)i). The reduction of the nitro group is conveniently carried out for example in a solvent or mixture of solvents such as water, aqueous ammonium chloride solution, hydrochloric acid, sulphuric acid, phosphoric acid, formic acid, acetic acid, acetic anhydride with base metals such as iron, zinc, tin or sulphur compounds such as ammonium sulphide, sodium sulphide or sodium dithionite or by catalytic hydrogenation with hydrogen, for example under a pressure between 0.5 and 100 bar, but preferably between 1 and 50 bar, or with hydrazine as reducing agent, conveniently in the presence of a catalyst such as for example Raney nickel, palladium charcoal, platinum oxide, platinum on mineral fibres or rhodium, or with complex hydrides such as lithium aluminium hydride, sodium borohydride, sodium cyanoborohydride, diisobutylaluminium hydride, conveniently in a solvent or mixture of solvents such as water, methanol, ethanol, isopropanol, pentane, hexane, cyclohexane, heptane, benzene, toluene, xylene, ethyl acetate, methylpropionate, glycol, glycoldimethyl ether, diethyleneglycol dimethyl ether, dioxane, tetrahydrofuran, N-methylpyrrolidinone, or N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C.

The reductive amination is conveniently carried out with the corresponding $R^3$-aldehyde (formaldehyde or paraformaldehyde where $R^3$=methyl, acetaldehyde or paraldehyde where $R^3$=ethyl, propionaldehyde where $R^3$=propyl) in a solvent or mixture of solvents such as methanol, ethanol, propanol, isopropanol, butanol, tetrahydrofuran, dioxane, diethyl ether, tert.-butyl-methyl-ether, ethyleneglycol dimethylether, diethyleneglycol dimethylether, sulpholane, dimethylformamide, N-methylpyrrolidinone, tetralin, dimethylsulphoxide, methylene chloride, chloroform or tetrachloromethane, for example at temperatures between −30 and 250° C., but preferably between −10 and 150° C., optionally in the presence of a base such as sodium methoxide, sodium ethoxide, sodium-tert.-butoxide, potassium-tert.-butoxide, sodium-tert.-butyldimethyl-silanoate, potassium hexamethyldisilazane, lithium diisopropylamide, potassium carbonate, rubidium carbonate, caesium carbonate, potassium phosphate, sodium hydride, optionally in the presence of a complexing agent such as 18-crown-6-ether, followed by reduction of the resulting imide by hydrogenation with hydrogen, for example under a pressure between 0.5 and 100 bar, but preferably between 1 and 50 bar, conveniently in the presence of a catalyst such as for example Raney nickel, palladium charcoal, platinum oxide, platinum on mineral fibres or rhodium, or with complex hydrides such as lithium aluminium hydride, sodium borohydride, sodium cyanoborohydride, diisobutylaluminium hydride, for example at temperatures between −30 and 250° C., but preferably between 0 and 150° C.

3) In order to prepare compounds of general formula (IIc):

a) Acylation of compounds of general formula (IIb) with compounds of general formula (VI)

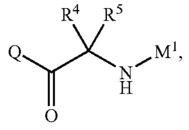

where A and $R^1$ to $R^5$ are as hereinbefore defined, Q denotes a hydroxy or $C_{1-4}$-alkoxy group, a halogen atom or an acyloxy group, and $M^1$ denotes a protective group which is optionally subsequently cleaved.

The acylation is carried out as described for the cases in 1)i).

b) Acylation of compounds of general formula (VII)

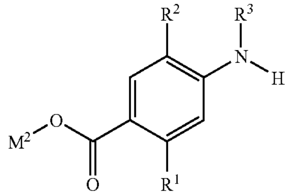

with compounds of general formula (VI) optionally followed by cleaving of the protective group $M^2$ and acylation of a compound of general formula (IIa) by means of the compound thus obtained, optionally followed by cleaving of the protective group $M^1$, while A and $R^1$ to $R^5$ are as hereinbefore defined, Q denotes a hydroxy or $C_{1-4}$-alkoxy group, a halogen atom or an acyloxy group, and both $M^1$ and $M^2$ denote protective groups.

The acylations are carried out as described in 1)i).

4) In order to prepare compounds of general formula (IIIb): Acylation of compounds of general formula (VIII)

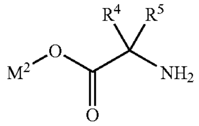

with compounds of general formula (IIIc) optionally followed by cleaving of the protective group $M^2$ and transformation into a reactive carboxylic acid derivative of formula (IIIb), where $R^4$ to $R^6$ are as hereinbefore defined, Q denotes a hydroxy or $C_{1-4}$-alkoxy group, a halogen atom or an acyloxy group, and $M^2$ denotes a protective group which is optionally subsequently cleaved.

The acylation is carried out as described in 1)i).

5) In order to prepare compounds of general formula (IIIa):

a) Acylation of compounds of general formula (VII) with compounds of general formula (IIIb), where $R^1$ to $R^6$ are as hereinbefore defined, Q denotes a hydroxy or $C_{1-4}$-alkoxy group, a halogen atom or an acyloxy group, and $M^2$ denotes a protective group which is optionally subsequently cleaved.

The acylation is carried out as for the cases illustrated in 1)i).

b) Acylation of compounds of general formula (VII) with compounds of general formula (VI) followed by cleaving of the protective group $M^1$ and acylation of the compound thus obtained with a compound of general formula (IIIc) optionally followed by cleaving of the protective group $M^2$, while $R^1$ to $R^6$ are as hereinbefore defined, Q in each case independently of one another denotes a hydroxy or $C_{1-4}$-alkoxy group, a halogen atom or an acyloxy group, and both $M^1$ and $M^2$ denote protective groups.

The acylations are carried out as described in 1)i).

In the reactions described above any reactive groups present such as hydroxy, carboxy, amino, alkylamino or imino groups may be protected during the reaction by conventional protective groups which are cleaved again after the reaction.

For example a suitable protective group for a hydroxy group is the methoxy, benzyloxy, trimethylsilyl, acetyl, benzoyl, tert.-butyl, trityl, benzyl or tetrahydro-pyranyl group, a suitable protective group for a carboxyl group is the trimethylsilyl, methyl, ethyl, tert.-butyl, benzyl or tetrahydropyranyl group and a suitable protective group for an amino, alkylamino or imino group is the acetyl, trifluoroacetyl, benzoyl, ethoxycarbonyl, tert.-butoxycarbonyl, benzyloxycarbonyl, benzyl, methoxybenzyl or 2,4-dimethoxybenzyl group and additionally a suitable protective group for the amino group is the phthalyl group.

Other protective groups and their cleaving are described in T. W. Greene, P. G. M. Wuts, "Protective Groups in Organic Synthesis", Wiley, 1991 and 1999.

Any protective group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by means of ether splitting, e.g. in the presence of iodotrimethylsilane, at temperatures between 0 and 100° C., preferably at temperatures between 10 and 50° C.

A benzyl, methoxybenzyl or benzyloxycarbonyl group, however, is cleaved by hydrogenolysis, for example, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and under a hydrogen pressure of 1 to 7 bar, but preferably 1 to 5 bar.

A methoxybenzyl group may also be cleaved in the presence of an oxidising agent such as cerium(IV)ammonium nitrate in a solvent such as methylene chloride, acetonitrile or acetonitrile/water at temperatures between 0 and 50° C., but preferably at ambient temperature.

A methoxy group is conveniently cleaved in the presence of boron tribromide in a solvent such as methylene chloride at temperatures between −35 and −25° C.

A 2,4-dimethoxybenzyl group, however, is preferably cleaved in trifluoroacetic acid in the presence of anisol.

A tert.-butyl or tert.-butyloxycarbonyl group is preferably cleaved by treatment with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treatment with a catalytic amount of tetrakis-(triphenylphosphine)-palladium (0), preferably in a solvent such as tetrahydrofuran and preferably in the presence of an excess of a base such as morpholine or 1,3-dimedone at temperatures between 0 and 100° C., preferably at ambient temperature and under inert gas, or by treatment with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

Moreover, the compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical enantiomers and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned hereinbefore, the compounds of general formula I and the tautomers, enantiomers, diastereomers and physiologically acceptable salts thereof have valuable pharmacological properties, particularly an antithrombotic activity which is preferably based on an effect on thrombin or factor Xa, for example on a thrombin-inhibiting or factor Xa-inhibiting activity, on a prolonging effect on the aPTT time and/or on an inhibitory effect on related serine proteases such as e.g. urokinase, factor VIIa, factor IXa, factor XIa and factor XIIa.

The compounds listed in the Experimental Section were investigated for their effect on the inhibition of factor Xa as follows:

Method:

Enzyme-kinetic measurement with chromogenic substrate. The quantity of p-nitroaniline (pNA) released from the colourless chromogenic substrate by human factor Xa is determined photometrically at 405 nm. It is proportional to the activity of the enzyme used. The inhibition of the enzyme activity by the test substance (in relation to the solvent control) is determined at various concentrations of test substance and from this the $IC_{50}$ is calculated, as the concentration which inhibits the factor Xa used by 50%.

Material:

Tris(hydroxymethyl)-aminomethane buffer (100 mMol) and sodium chloride (150 mMol), pH 8.0 plus 1 mg/ml Human Albumin Fraction V, protease-free Factor Xa (Calbiochem), spec. activity: 217 IU/mg, final concentration: 7 IU/ml for each reaction mixture Substrate S 2765 (Chromogenix), final concentration: 0.3 mM/l (1 KM) for each reaction mixture Test substance: final concentration 100, 30, 10, 3, 1, 0.3, 0.1, 0.03, 0.01, 0.003, 0.001 μMol/l Procedure:

10 μl of a 23.5-times concentrated starting solution of the test substance or solvent (control), 175 μl of TRIS/HSA buffer and 25 μl of a 65.8 U/L Factor Xa working solution are incubated for 10 minutes at 37° C. After the addition of 25 μl of S 2765 working solution (2.82 mMol/l) the sample is measured in a photometer (SpectraMax 250) at 405 nm for 600 seconds at 37° C.

Evaluation:

1. Determining the maximum increase (deltaOD/minutes) over 21 measuring points.

2. Determining the % inhibition based on the solvent control.

3. Plotting a dosage/activity curve (% inhibition vs substance concentration).

4. Determining the $IC_{50}$ by interpolating the X-value (substance concentration) of the dosage/activity curve at Y=50% inhibition.

All the compounds tested had an $IC_{50}$ value of less than 100 μmol/L.

The compounds prepared according to the invention are generally well tolerated.

In view of their pharmacological properties the new compounds and the physiologically acceptable salts thereof are suitable for the prevention and treatment of venous and arterial thrombotic diseases, such as for example the prevention and treatment of deep leg vein thrombosis, for preventing reocclusions after bypass operations or angioplasty (PT(C)A), and occlusion in peripheral arterial diseases, and for preventing and treating pulmonary embolism, disseminated intravascular coagulation and severe sepsis, for preventing and treating DVT in patients with exacerbated COPD, for treating ulcerative colitic, for preventing and treating coronary thrombosis, for preventing stroke and the occlusion of shunts.

In addition, the compounds according to the invention are suitable for antithrombotic support in thrombolytic treatment, such as for example with alteplase, reteplase, tenecteplase, staphylokinase or streptokinase, for preventing long-term restenosis after PT(C)A, for the prevention and treatment of ischaemic incidents in patients with all forms of coronary heart disease, for preventing metastasis and the growth of tumours and inflammatory processes, e.g. in the treatment of pulmonary fibrosis, for preventing and treating rheumatoid arthritis, for preventing and treating fibrin-dependent tissue adhesions and/or the formation of scar tissue and for promoting wound healing processes.

In view of their pharmacological properties the new compounds and the physiologically acceptable salts thereof are also suitable for the treatment of Alzheimer's and Parkinson's disease. One explanation for this arises for example from the following findings, from which it can be concluded that thrombin inhibitors or factor Xa inhibitors, by inhibiting thrombin formation or thrombin activity, may be valuable drugs for treating Alzheimer's and Parkinson's disease. Clinical and experimental studies indicate that neurotoxic mechanisms, for example the inflammation which is associated with the activation of proteases of the clotting cascade, are involved in the dying of neurones following brain injury. Various studies point to the involvement of thrombin in neurodegenerative processes, for example following a stroke, repeated bypass operations or traumatic brain injury. An increased thrombin activity has been demonstrated some days after peripheral nerve damage, for example. It has also been shown that thrombin causes a neurite retraction, as well as glia proliferation, and apoptosis in primary cultures of neurones and neuroblastoma cells (for a summary see: *Neurobiol. Aging* 2004, 25(6), 783-793). Moreover, various in vitro studies on the brains of patients with Alzheimer's disease indicated that thrombin plays a role in the pathogenesis of this disease (*Neurosci. Lett.* 1992, 146, 152-54). A concentration of immune-reactive thrombin has been detected in neurite plaques in the brains of Alzheimer's patients. It has been demonstrated in vitro that thrombin also plays a part in the regulation and stimulation of the production of the "Amyloid Precursor Protein" (APP) as well as in the cleaving of the APP into fragments which can be detected in the brains of Alzheimer's patients. Moreover, it has been demonstrated that the thrombin-induced microglial activation leads in vivo to the degeneration of nigral dopaminergic neurones. These findings lead one to conclude that microglial activation, triggered by endogenous substance(s) such as thrombin, for example, are involved in the neuropathological process of the cell death of dopaminergic neurones of the kind which occurs in patients with Parkinson's disease (*J. Neurosci.* 2003, 23, 5877-86).

The dosage required to achieve such an effect is appropriately 0.01 to 3 mg/kg, preferably 0.03 to 1.0 mg/kg by intravenous route, and 0.03 to 30 mg/kg, preferably 0.1 to 10 mg/kg by oral route, in each case administered 1 to 4 times a day.

For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. clopidogrel, ticlopidine), with $P_2T$ receptor antagonists (e.g. cangrelor) or with combined thromboxane receptor antagonists/synthetase inhibitors (e.g. terbogrel).

The Examples that follow are intended to illustrate the invention, without restricting its scope:

EXPERIMENTAL SECTION

As a rule, melting points, IR, UV, $^1$H-NMR and/or mass spectra have been obtained for the compounds prepared. Unless otherwise stated, $R_f$ values were determined using ready-made silica gel 60 $F_{254\,s}$ TLC plates (E. Merck, Darmstadt, Item no. 1.05714) without chamber saturation. The $R_f$ values given under the heading Alox were determined using ready-made aluminium oxide 60 $F_{254}$ TLC plates (E. Merck, Darmstadt, Item no. 1.05713) without chamber saturation. The $R_f$ values given under the heading Reversed-phase-8 (RP-8) were determined using ready-made RP-8 $F_{254}$, TLC plates (E. Merck, Darmstadt, Item no. 1.15684) without chamber saturation. The ratios given for the eluants refer to units by volume of the solvents in question. For chromato-graphic purification silica gel made by Messrs Millipore (MATREX™, 35-70 my) was used. Unless more detailed information is provided as to the configuration, it is not clear whether the products are pure stereoisomers or mixtures of enantiomers and diastereomers.

The HPLC-MS 1 data were obtained under the following conditions:

Waters Alliance 2690 HPLC, Waters 2700 Autosampler, Waters 996 Diode array detector The mobile phase used was:

A: water with 0.13% TFA

B: acetonitrile with 0.10% TFA

| time in min | % A | % B | flow rate in ml/min |
|---|---|---|---|
| 0.0 | 95 | 5 | 1.00 |
| 0.1 | 95 | 5 | 1.00 |
| 3.1 | 2 | 98 | 1.00 |
| 4.5 | 2 | 98 | 1.00 |
| 5.0 | 95 | 5 | 1.00 |

The stationary phaase used was a Waters column, Xterra MS $C_{18}$ 2.5 µm, 4.6 mm×30 mm, (column temperature: constant at 25° C.).

The diode array detection was carried out at a wavelength range of 210-500 nm.

The HPLC-MS 2 data, where specified, were obtained under the following conditions:

HP 1100 with quaternary pump, Gilson G215 Autosampler, HP diode array detector, Waters ZQ2000 mass spectrometer.

The mobile phase used was:

A: water with 0.1% TFA

B: acetonitrile with 0.1% TFA

| time in min | % A | % B | flow rate in ml/min |
|---|---|---|---|
| 0.00 | 95 | 5 | 1.0 |
| 0.40 | 95 | 5 | 1.0 |
| 4.00 | 2 | 98 | 1.0 |
| 4.35 | 2 | 98 | 1.0 |
| 4.50 | 95 | 5 | 1.0 |

The stationary phaase used was a Waters column, X-Terra™ MS $C_{18}$ 3.5 µm, 4.6 mm×50 mm (column temperature constant at 40° C.).

The diode array detection was carried out at a wavelength range from 210-550 nm

Range of mass-spectrometric detection: m/z 120 to m/z 1000.

The following abbreviations are used in the descriptions of the experiments:

Boc tert.-butoxycarbonyl
DIPEA N-ethyl-diisopropylamine
DMSO dimethylsulphoxide
DMF N,N-dimethylformamide
sat. saturated
h hour(s)
HATU O-(7-azabenzotriazol-1-yl)-N,N,N',N'-tetramethyluronium-hexafluorophosphate
i. vac. in vacuo
conc. concentrated
min minute(s)
NMM N-methyl-morpholine
NMP N-methyl-pyrrolidin-2-one
o ortho
PfTU O-pentafluorophenyl-N,N,N',N'-tetramethyluronium-hexafluorophosphate
PPA propanephosphonic acid cycloanhydride
quant. quantitative
$R_f$ retention factor
$R_t$ retention time
rac. racemic
TBTU O-(benzotriazol-1-yl)-N,N,N',N'-tetramethyluronium tetrafluoroborate
TEA triethylamine
TFA trifluoroacetic acid
THF tetrahydrofuran
tert. tertiary
Σ yield over all the steps carried out analogously as described

Example 1

5-chloro-thiophene-2-carboxylic acid-N-{1-[3-chloro-4-(pyrrolidin-1-yl-carbonyl)-phenylcarbamoly]-ethyl}-amide

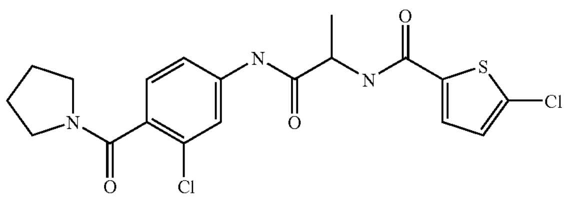

(a) 3-chloro-4-(pyrrolidin-1-yl-carbonyl)-1-nitro-benzene 9.92 g (49.2 mmol) 2-chloro-4-nitro-benzoic acid are combined with 16.94 g (52.8 mmol) TBTU and 18.4 ml DIPEA in 200 ml THF with stirring at ambient temperature and stirred for 15 min. Then 4.0 ml (3.41 g, 48.0 mmol) pyrrolidine are added and the mixture is stirred for 2 hours at ambient temperature. After evaporation i. vac. the residue is taken up in ethyl acetate, washed with 2-molar hydrochloric acid and sat. sodium hydrogen carbonate solution, dried over magnesium sulphate and evaporated down i. vac.

Yield: 11.56 g (95%)

$R_f$ value: 0.49 (silica gel; dichloromethane/ethanol=19:1)

$C_{11}H_{11}ClN_2O_3$ (254.67)

Mass spectrum: $(M+H)^+$=255/257 (chlorine isotope)

(b) 3-chloro-4-(pyrrolidin-1-yl-carbonyl)-aniline 10.10 g (40.0 mmol) 3-chloro-4-(pyrrolidin-1-yl-carbonyl)-1-nitro-benzene is combined with 5 ml (5.15 g, 100 mmol) hydrazine hydrate in 150 ml of methanol and 2.00 g Raney nickel are added. While stirring at ambient temperature a total of 9 ml (9.29 g, 186 mmol) hydrazine hydrate and 9.00 g Raney nickel are added batchwise over 36 hours, then the mixture is filtered and the filtrate is evaporated down i. vac. The residue is taken up in acetone and filtered again. The filtrate is evaporated down i. vac., dissolved in acetone and cooled in the ice bath. The resulting precipitate is filtered off and dried at ambient temperature.

Yield: 6.20 g (69%)

$R_f$ value: 0.34 (silica gel; dichloromethane/ethanol=19:1)

$C_{11}H_{13}ClN_2O$ (224.69)

Mass spectrum: $(M+H)^+$=225/227 (chlorine isotope)

(c) methyl 2-[(5-chloro-thiophene-2-carbonyl)-amino]-propionate

Prepared analogously to Example 1a from methyl 5-chloro-thiophene-2-carboxylic acid and 2-aminopropionate with TBTU and NMM in THF.

Yield: 81%

$R_f$ value: 0.63 (silica gel; petroleum ether/ethyl acetate=1:1)

$C_9H_{10}ClNO_3S$ (247.70)

Mass spectrum: $(M+H)^+$=248/250 (chlorine isotope)

(d) 2-[(5-chloro-thiophene-2-carbonyl)-amino]-propionic acid 3.80 g (15.3 mmol) methyl 2-[(5-chloro-thiophene-2-carbonyl)-amino]-propionate are suspended in 15.5 ml (15.5 mmol) 1-molar aqueous sodium hydroxide solution, combined with 15 ml of ethanol and then stirred for 4 hours at ambient temperature. After evaporation i. vac. the residue is combined with ice water, extracted with diethyl ether, the aqueous phase is poured into anice/acetic acid mixture and the resulting precipitate is suction filtered. After washing with water the precipitate is dried at 60° C.

Yield: 2.90 g (81%)

$R_f$ value: 0.28 (silica gel; petroleum ether/ethyl acetate=1:2)

$C_8H_8ClNO_3S$ (233.67)

(e) 5-chloro-thiophene-2-carboxylic acid-N-{1-[3-chloro-4-(pyrrolidin-1-yl-carbonyl)-phenylcarbamoyl]-ethyl}-amide Prepared analogously to Example 1a from 2-[(5-chloro-thiophene-2-carbonyl)-amino]-propionic acid and 3-chloro-4-(pyrrolidin-1-yl-carbonyl)-aniline with TBTU and NMM in DMF.

Yield: 77%

$R_f$ value: 0.24 (silica gel; petroleum ether/ethyl acetate=1:2)

$C_{19}H_{19}Cl_2N_3O_3S$ (440.34)

Mass spectrum: $(M+H)^+$=440/442/444 (chlorine isotope)

Example 2

5-chloro-thiophene-2-carboxylic acid-N-{(1R)-2-methoxy-1-[3-methyl-4-(pyrrolidin-1-yl-carbonyl)-phenylcarbamoly]-ethyl}-amide

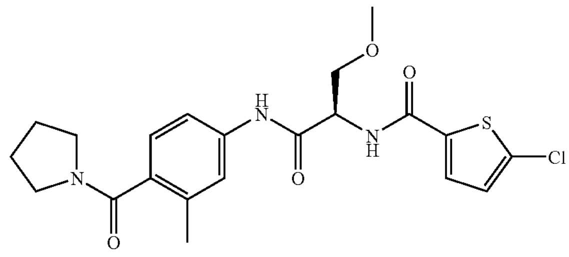

(a) (2R)-2-Boc-amino-3-methoxy-propionic acid 20 g (approx. 0.5 mol) sodium hydride is added batchwise to a mixture of 740 ml THF and 60 ml of methanol with cooling in a bath of isopropanol/dry ice and then stirred for 15 min at ambient temperature. 20.52 g (100 mmol) N-Boc-D-serine in 100 ml THF are combined with half the sodium methoxide solution thus obtained and stirred for one hour at ambient temperature under a nitrogen atmosphere. Then 10 ml (22.80 g, 0.16 mol) iodomethane are added and the mixture is again stirred for one hour at ambient temperature. Then the remaining half of the sodium methoxide solution is added, the mixture is again stirred for one hour at ambient temperature, and then 20 ml (45.60 g, 0.32 mol) iodomethane are added. The mixture is then stirred for 18 hours at ambient temperature under a nitrogen atmosphere. The reaction mixture is evaporated down i. vac., the residue is dissolved in water and extracted with diethyl ether. The aqueous phase is adjusted to pH 4 with citric acid solution and extracted with ethyl acetate. The combined organic phases are washed with sat. sodium chloride solution, dried over sodium sulphate and evaporated down i. vac. The residue is taken up in dichloromethane and water, extracted with dichloromethane, the combined organic phases are washed with sat. sodium chloride solution and dried over sodium sulphate. Then the mixture is evaporated down completely i. vac.

Yield: 6.15 g (28%)

$R_f$ value: 0.45 (RP-8; methanol/5% sodium chloride solution=7:3)

$C_9H_{17}NO_5$ (219.24)

Mass spectrum: $(M+H)^+$=220

(b) N-acetyl-3-methyl-4-(pyrrolidin-1-yl-carbonyl)-aniline 25.0 g (124 mmol) N-acetyl-4-amino-2-methyl-benzoic acid are combined with 3 drops DMF in 1000 ml dichloromethane and a solution of 21.0 ml (30.56 g, 241 mmol) oxalyl chloride in 100 ml TEA is added dropwise with stirring and cooling in the ice bath. Then the mixture is heated to 50° C. for 4.5 hours. The reaction mixture is filtered and the filtrate is evaporated down completely i. vac. The residue is taken up in 100 ml dichloromethane and this solution is added dropwise to a mixture of 10.4 ml (8.86 g, 125 mmol) pyrrolidine and 34.4 ml (25.0 g, 247 mmol) TEA in 500 ml dichloromethane with stirring and cooling in the ice bath. The mixture is stirred for 16 hours at ambient temperature. After filtering the filtrate is washed with 1-molar hydrochloric acid and sat. sodium chloride solution, combined with activated charcoal and dried over sodium sulphate. After evaporation i. vac. the residue is purified by chromatography on silica gel.

Yield: 9.50 g (31%)

$R_t$ value: 3.32 min $C_{14}H_{18}N_2O_2$ (246.31)

Mass spectrum: $(M+H)^+$=247

(c) 3-methyl-4-(pyrrolidin-1-yl-carbonyl)-aniline 2.00 g (7.31 mmol) N-acetyl-2-methyl-4-(pyrrolidin-1-yl-carbonyl)-aniline in 50 ml 6-molar hydrochloric acid is heated to 105° C. for 25 min. The reaction mixture is poured into ice water, filtered, and sodium chloride and conc. ammonia solution are added to the filtrate until a pH of 9 is obtained. Then it is extracted with ethyl acetate. The combined organic phases are washed with semisat. and sat. sodium chloride solution, dried over sodium sulphate and evaporated down i. vac. The residue is combined with diethyl ether and triturated, the solid precipitate is suction filtered and dried in the air. The remaining product is obtained by evaporation of the mother liquor.

Yield: 1.20 g (70%)

$R_f$ value: 0.50 (silica gel; ethyl acetate/ethanol=9:1+1% conc. ammonia solution)

$C_{12}H_{16}N_2O$ (204.27)

Mass spectrum: $(M+H)^+$=205

(d) (2R)-2-N-Boc-amino-3-methoxy-propionic acid-N'-[3-methyl-4-(pyrrolidin-1-yl-carbonyl)-phenyl]-amide Prepared analogously to Example 1a from (2R)-2-N-Boc-amino-3-methoxy-propionic acid and 3-methyl-4-(pyrrolidin-1-yl-carbonyl)-aniline with TBTU and NMM in DMF with subsequent purification by chromatography on silica gel.

Yield: 34%

$R_f$ value: 0.55 (silica gel; dichloromethane/ethanol=9:1)

$C_{21}H_{31}N_3O_5$ (405.49)

Mass spectrum: $(M+H)^+$=406

(e) (2R)-2-amino-3-methoxy-propionic acid-N-[3-methyl-4-(pyrrolidin-1-yl-carbonyl)-phenyl]-amide 200 mg (0.49 mmol) (2R)-2-N-Boc-amino-3-methoxy-propionic acid-N'-[3-methyl-4-(pyrrolidin-1-yl-carbonyl)-phenyl]-amide are combined with 0.5 ml trifluoroacetic acid in 10 ml dichloromethane and stirred for 20 hours at ambient temperature. After evaporation i. vac. the residue is taken up in dichloromethane and diethyl ether and evaporated down completely i. vac. The residue is stirred with a mixture of petroleum ether/diethyl ether 1:1 and then suction filtered.

Yield: 207 mg (99%)

$R_f$ value: 0.55 (RP-8; 5% sodium chloride solution/methanol=7:3)

$C_{16}H_{23}N_3O_3*CF_3COOH$ (419.40/305.38)

Mass spectrum: $(M+H)^+$=306

(f) 5-chloro-thiophene-2-carboxylic acid-N-{(1R)-2-methoxy-1-[3-methyl-4-(pyrrolidin-1-yl-carbonyl)-phenylcarbamoyl]-ethyl}-amide 81.3 mg (0.50 mmol) 5-chloro-thiophene-2-carboxylic acid are combined with one drop of DMF and 1 ml of thionyl chloride in 5 ml dichloromethane and refluxed for 2 hours. The mixture is then evaporated down completely i. vac., combined with dichloromethane and in each case evaporated down again completely. To the residue is added a mixture of 200 mg (0.48 mmol) (2R)-2-amino-3-methoxy-propionic acid-N-[3-methyl-4-(pyrrolidin-1-yl-carbonyl)-phenyl]-amide-trifluoroacetate combined with 0.21 ml (152 mg, 1.50 mmol) TEA in 15 ml dichloromethane and the mixture is stirred for 16 hours at ambient temperature. After evaporation i. vac. the residue is taken up in sat. sodium chloride solution and ethyl acetate and extracted with ethyl acetate. The combined organic phases are dried over sodium sulphate, evaporated down completely i. vac., the residue is stirred with petroleum ether/diethyl ether 1:1, suction filtered and dried in the air.

Yield: 115 mg (51%)

$R_f$ value: 0.55 (silica gel; dichloromethane/ethanol=9:1)

$C_{21}H_{24}ClN_3O_4S$ (449.95)

Mass spectrum: $(M+H)^+$=450/452 (chlorine isotope)

The following compounds may be prepared analogously:

(1) 5-chloro-thiophene-2-carboxylic acid-N-{(1S)-2-methoxy-1-[3-methyl-4-(pyrrolidin-1-yl-carbonyl)-phenylcarbamoyl]-ethyl}-amide, (2) 5-bromo-thiophene-2-carboxylic acid-N-{(1R)-2-methoxy-1-methyl-1-[3-methyl-4-(pyrrolidin-1-yl-carbonyl)-phenylcarbamoyl]-ethyl}-amide, (3) 5-bromo-thiophene-2-carboxylic acid-N-{(1S)-2-methoxy-1-methyl-1-[3-methyl-4-(pyrrolidin-1-yl-carbonyl)-phenylcarbamoyl]-ethyl}-amide, (4) 5-bromo-thiophene-2-carboxylic acid-N-{(1R)-2-methoxy-1-[3-methyl-4-(pyrrolidin-1-yl-carbonyl)-phenylcarbamoyl]-ethyl}-amide, (5) 5-bromo-thiophene-2-carboxylic acid-N-{(1S)-2-methoxy-1-[3-methyl-4-(pyrrolidin-1-yl-carbonyl)-phenylcarbamoyl]-ethyl}-amide, (6) 5-bromo-thiophene-2-carboxylic acid-N-{2-methoxy-1-[3-methyl-4-(pyrrolidin-1-yl-carbonyl)-phenylcarbamoyl]-propyl}-amide, Example 3

5-bromo-thiophene-2-carboxylic acid-N-{1-methyl-1-[3-methyl-4-(pyrrolidin-1-yl-carbonyl)-phenylcarbamoly]-ethyl}-amide

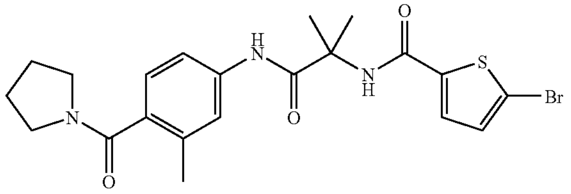

(a) 2-N-Boc-amino-isobutyric acid-N'-[3-methyl-4-(pyrrolidin-1-yl-carbonyl)-phenyl]-amide Prepared analogously to Example 1a from 2-N-Boc-amino-isobutyric acid and 3-methyl-4-(pyrrolidin-1-yl-carbonyl)-aniline with TBTU and TEA in DMF.

Yield: 66%

$R_f$ value: 0.62 (silica gel; ethyl acetate/ethanol=9:1+1% conc. ammonia solution)

$C_{21}H_{31}N_3O_4$ (389.49)

(b) 2-amino-isobutyric acid-N-[3-methyl-4-(pyrrolidin-1-yl-carbonyl)-phenyl]-amide 1.10 g (2.82 mmol) 2-N-Boc-amino-isobutyric acid-N'-[3-methyl-4-(pyrrolidin-1-yl-carbonyl)-phenyl]-amide are combined with 15 ml 6-molar hydrochloric acid in 5 ml dioxane and stirred for one hour at ambient temperature. Then the mixture is extracted with diethyl ether, the aqueous phase is poured into in ice water and adjusted to approx. pH 9 with conc. ammonia. Then it is extracted with dichloromethane, the combined organic phases are dried over magnesium sulphate and evaporated down completely i. vac.

Yield: 680 mg (79%)

$R_f$ value: 0.30 (silica gel; ethyl acetate/ethanol=9:1+1% conc. ammonia solution)

$C_{16}H_{23}N_3O_2$ (289.37)

(c) 5-bromo-thiophene-2-carboxylic acid-N-{1-methyl-1-[3-methyl-4-(pyrrolidin-1-yl-carbonyl)-phenylcarbamoyl]-ethyl}-amide Prepared analogously to Example 1a from 5-bromo-thiophene-2-carboxylic acid and 2-amino-isobutyric acid-N-[3-methyl-4-(pyrrolidin-1-yl-carbonyl)-phenyl]-amide with TBTU and NMM in THF.

Yield: 50%

$R_f$ value: 0.52 (silica gel; ethyl acetate/ethanol=9:1+1% conc. ammonia solution)

$C_{21}H_{24}BrN_3O_3S$ (478.40)

Mass spectrum: $(M+H)^+$=479/481 (bromine isotope)

The following compounds were prepared analogously:

| No. | Structural formula / Name | Yield | Mass peak(s) | $R_f$ value or $R_t$ |
|---|---|---|---|---|
| 4 | 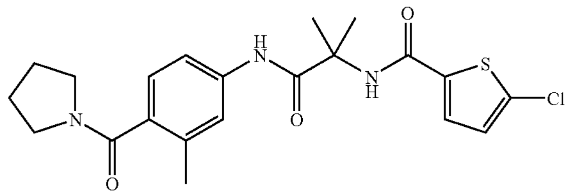 5-chloro-thiophene-2-carboxylic acid-N-{1-methyl-1-[3-methyl-4-(pyrrolidin-1-yl-carbonyl)-phenylcarbamoyl]-ethyl}-amide | Σ: 29% | $(M + H)^+$ = 434/436 (chlorine isotope) | 0.52 (silica gel; ethyl acetate/ethanol = 9:1 + 1% ammonia) |
| 11 | 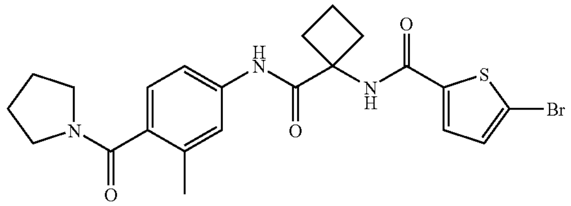 5-bromo-thiophene-2-carboxylic acid-N-{1-[3-methyl-4-(pyrrolidin-1-yl-carbonyl)-phenylcarbamoyl]-cyclobut-1-yl)-amide | Σ: 57% | $(M + H)^+$ = 490/492 (bromine isotope) | 0.55 (silica gel; dichloromethane/ ethanol = 9:1) |
| 14 | 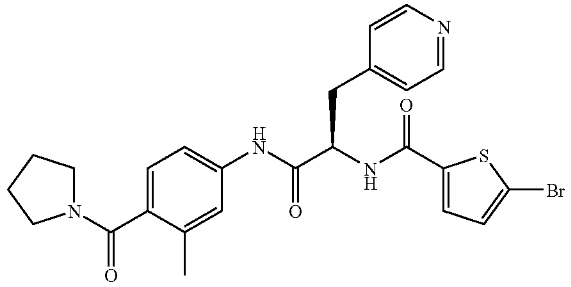 5-bromo-thiophene-2-carboxylic acid-N-{(1R)-2-[pyridin-4-yl]-1-[3-methyl-4-(pyrrolidin-1-yl-carbonyl)-phenylcarbamoyl]-ethyl)-amide | Σ: 16% | $(M + H)^+$ = 541/543 (bromine isotope) | 2.43 min (HPLC-MS 1) |
| 15 | 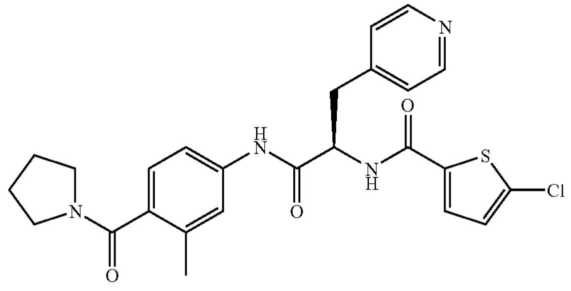 5-chloro-thiophene-2-carboxylic acid-N-{(1R)-2-[pyridin-4-yl]-1-[3-methyl-4-(pyrrolidin-1-yl-carbonyl)-phenylcarbamoyl]-ethyl)-amide | Σ: 21% | $(M + H)^+$ = 497/499 (chlorine isotope) | 2.41 min (HPLC-MS 1) |

-continued

| No. | Structural formula / Name | Yield | Mass peak(s) | $R_f$-value or $R_t$ |
|---|---|---|---|---|
| 17 | 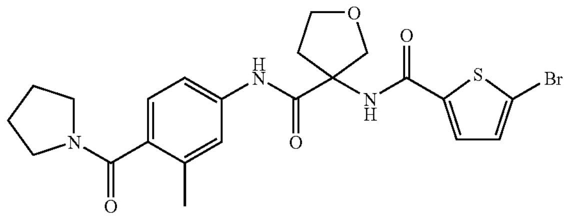 5-bromo-thiophene-2-carboxylic acid-N-{3-[3-methyl-4-(pyrrolidin-1-yl-carbonyl)-phenylcarbamoyl]-tetrahydrofuran-3-yl)-amide | Σ: 44% | $(M + H)^+$ = 506/508 (bromine isotope) | 0.58 (silica gel; ethyl acetate/ethanol = 9:1 + 1% ammonia) |
| 18 | 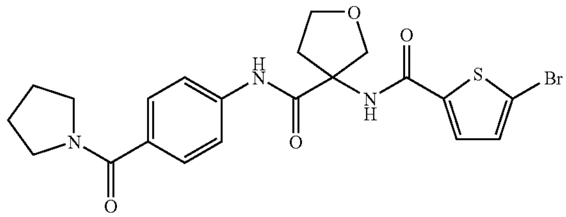 5-bromo-thiophene-2-carboxylic acid-N-{3-[4-(pyrrolidin-1-yl-carbonyl)-phenylcarbamoyl]-tetrahydrofuran-3-yl}-amide | Σ: 23% | $(M + H)^+$ = 492/494 (bromine isotope) | 0.40 (silica gel; ethyl acetate/ethanol = 9:1 + 1% ammonia) |

The following compounds may be prepared analogously:

(1) 5-bromo-thiophene-2-carboxylic acid-N-{3-methylsulphanyl-1-[3-methyl-4-(pyrrolidin-1-yl-carbonyl)-phenylcarbamoyl]-propyl}-amide, (2) 5-bromo-thiophene-2-carboxylic acid-N-{3-methyl-1-[3-methyl-4-(pyrrolidin-1-yl-carbonyl)-phenylcarbamoyl]-butyl}-amide, (3) 5-bromo-thiophene-2-carboxylic acid-N-{3-methyloxycarbonyl-1-[3-methyl-4-(pyrrolidin-1-yl-carbonyl)-phenylcarbamoyl]-propyl}-amide, (4) 5-bromo-thiophene-2-carboxylic acid-N-{3-dimethylaminocarbonyl-1-[3-methyl-4-(pyrrolidin-1-yl-carbonyl)-phenylcarbamoyl]-propyl}-amide, (5) 5-bromo-thiophene-2-carboxylic acid-N-{2-phenyl-1-[3-methyl-4-(pyrrolidin-1-yl-carbonyl)-phenylcarbamoyl]-ethyl}-amide, (6) 5-bromo-thiophene-2-carboxylic acid-N-{1-(thiophenyl-3-yl)-1-[3-methyl-4-(pyrrolidin-1-yl-carbonyl)-phenylcarbamoyl]-methyl}-amide, (7) 5-bromo-thiophene-2-carboxylic acid-N-{5-dimethylamino-1-[3-methyl-4-(pyrrolidin-1-yl-carbonyl)-phenylcarbamoyl]-pentyl}-amide, (8) 5-bromo-thiophene-2-carboxylic acid-N-{1-[3-methyl-4-(pyrrolidin-1-yl-carbonyl)-phenylcarbamoyl]-cyclohexyl}-amide,

Example 5

5-bromo-thiophene-2-carboxylic acid-N-{1-[3-chloro-4-(pyrrolidin-1-yl-carbonyl)-phenylcarbamoly]-1-methyl-ethyl}-amide

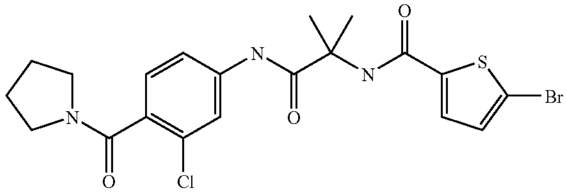

(a) tert.-butyl 2-[(5-bromo-thiophen-2-yl)-carbonylamino]-isobutyrate 2.63 g (12.3 mmol) 5-bromo-thiophene-2-carboxylic acid are refluxed in 15 ml dichloromethane together with 7.0 ml of thionyl chloride for 2 h with stirring. The mixture is then evaporated down i. vac. and the residue is twice taken up in toluene and evaporated down completely i. vac. The residue is added dropwise to 10 ml dichloromethane with stirring at ambient temperature in a mixture of 2.41 g (12.3 mmol) tert.-butyl 2-amino-isobutyrate hydrochloride in 20 ml dichloromethane with 5.14 ml (36.9 mmol) TEA and stirred for 16 h. The mixture is poured into water and extracted with dichloromethane, the combined organic phases are dried over magnesium sulphate and evaporated down i. vac.

Yield: 3.83 g (89%)

$C_{13}H_{18}BrNO_3S$ (348.26)

Mass spectrum: $(M+H)^+$=348/350 (bromine isotope)

(b) 2-[(5-bromo-thiophen-2-yl)-carbonylamino]-isobutyric acid

Prepared analogously to Example 2e from tert.-butyl 2-[(5-bromo-thiophen-2-yl)-carbonylamino]-isobutyrate with trifluoroacetic acid in dichloromethane.

Yield: 88%

$R_f$ value: 0.33 (silica gel; dichloromethane/methanol=9:1)

$C_9H_{10}BrNO_3S$ (292.15)

Mass spectrum: $(M+H)^+$=292/294 (bromine isotope)

(c) 5-bromo-thiophene-2-carboxylic acid-N-{1-[3-chloro-4-(pyrrolidin-1-yl-carbonyl)-phenylcarbamoyl]-1-methyl-ethyl}-amide 350 mg (1.20 mmol) 2-[(5-bromo-thiophen-2-yl)-carbonylamino]-isobutyric acid are stirred together with 450 mg (1.18 mmol) HATU and 100 μl (0.91 mmol) NMM in 12 ml THF for 45 min at ambient temperature. Then 250 mg (1.11 mmol) 3-chloro-4-(pyrrolidin-1-yl-carbonyl)-aniline and a further 250 μl (2.27 mmol) NMM are added and the mixture is stirred for 4 h at 120° C. and 300 W radiation energy in a microwave oven. After standing for 11 h at ambient temperature the mixture is stirred for a further 2.5 h at 120° C. and 300 W radiation energy in the microwave oven. After evaporation i. vac. sat. sodium hydrogen carbonate solution is added and the mixture is extracted with ethyl acetate. The combined organic phases are washed with semisat. sodium chloride solution, extracted with 0.5-normal potassium hydrogen sulphaet solution and extracted with semisat. and sat. sodium chloride solution. After drying over sodium sulphate and evaporation i. vac. the residue is purified by chromatography on silica gel.

Yield: 235 mg (42%)

$R_f$ value: 0.65 (silica gel; ethyl acetate/ethanol=9:1)

$C_{20}H_{21}BrClN_3O_3S$ (498.82)

Mass spectrum: $(M+H)^+$=498/500/502 (bromo- and chlorine isotope)

The following compound may be prepared analogously:

(1) 5-chloro-thiophene-2-carboxylic acid-N-{1-methyl-1-[3-chloro-4-(pyrrolidin-1-yl-carbonyl)-phenylcarbamoyl]-ethyl}-amide, Example 6

5-bromo-thiophene-2-carboxylic acid-N-{1-[3-bromo-4-(pyrrolidine-1-carbonyl)-phenylcarbamoyl]-1-methyl-ethyl}-amide

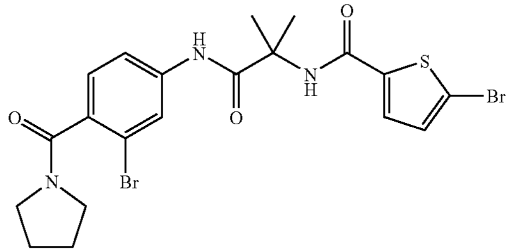

(a) 3-bromo-4-(pyrrolidin-1-yl-carbonyl)-1-nitro-benzene

Prepared analogously to Example 1a from 2-bromo-4-nitro-benzoic acid and pyrrolidine with TBTU and NMM in DMF.

Yield: (77%)

$R_f$ value: 0.25 (silica gel; petroleum ether/ethyl acetate=1:1)

$C_{11}H_{11}BrN_2O_3$ (299.12)

Mass spectrum: $(M+Na)^+$=321/323 (bromine isotope)

(b) 3-bromo-4-(pyrrolidin-1-yl-carbonyl)-aniline 27.50 g (73.55 mmol) 3-bromo-4-(pyrrolidin-1-yl-carbonyl)-1-nitro-benzene are dissolved in 100 ml of ethyl acetate and combined with 2.5 g 10% Pd/C. The mixture is hydrogenated in a Parr apparatus at ambient temperature at 5 bar hydrogen pressure for two hours. Then the catalyst is filtered off and the filtrate is evaporated down i. vac. The residue is combined with petroleum ether, the precipitate is filtered off and dried.

Yield: 5.60 g (28%)

$R_f$ value: 0.33 (silica gel; ethyl acetate/petroleum ether=9:1+1% conc. ammonia solution)

$C_{11}H_{13}BrN_2O$ (269.14)

Mass spectrum: $(M+Na)^+$=291/293 (bromine isotope)

(c) 5-bromo-thiophene-2-carboxylic acid-N-{1-[3-bromo-4-(pyrrolidine-1-carbonyl)-phenylcarbamoyl]-1-methyl-ethyl}-amide 165.0 mg (0.57 mmol) 2-[(5-bromo-thiophene-2-carbonyl)-amino]-2-methyl-propionic acid are combined with 215.0 mg (0.57 mmol) HATU and 60.0 μl (0.54 mmol) NMM in 6 ml THF with stirring at ambient temperature and stirred for 45 min. Then 150.0 mg (0.50 mmol) 3-bromo-4-(pyrrolidin-1-yl-carbonyl)-aniline and 100.0 μl (0.91 mmol) NMM are added and the mixture is stirred for 5 hours at 120° C. and 150 W radiation energy and stirred in a microwave oven. After evaporation i. vac. 0.5-normal potassium hydrogen sulphate solution is added and the mixture is extracted with ethyl acetate. The combined organic phases are washed with semisat. and sat. sodium chloride solution. After drying over magnesium sulphate and evaporation i. vac. the residue is purified by chromatography on silica gel (eluant gradient: ethyl acetate/ethanol=100:0->95:5).

Yield: 53.0 mg (19%)

$R_f$ value: 0.65 (silica gel; ethyl acetate/ethanol=9:1)

$C_{20}H_{21}Br_2N_3O_3S$ (543.27)

Mass spectrum: $(M+H)^+$=542/544/546 (bromine isotope)

The following compounds may be prepared analogously:

(1) 5-chloro-thiophene-2-carboxylic acid-N-{1-methyl-1-[3-bromo-4-(pyrrolidin-1-yl-carbonyl)-phenylcarbamoyl]-ethyl}-amide, (2) 5-bromo-thiophene-2-carboxylic acid-N-{1-methyl-1-[3-methyl-4-(2,5-dihydropyrrol-1-yl-carbonyl)-phenylcarbamoyl]-ethyl}-amide, (3) 5-bromo-thiophene-2-carboxylic acid-N-{1-methyl-1-[3-methyl-4-(thiazolidin-3-yl-carbonyl)-phenylcarbamoyl]-ethyl}-amide, (4) 5-bromo-thiophene-2-carboxylic acid-N-{1-methyl-1-[3-methyl-4-(2-dimethylaminomethylpyrrolidin-1-yl-carbonyl)-phenylcarbamoyl]-ethyl}-amide, (5) 5-bromo-thiophene-2-carboxylic acid-N-{1-methyl-1-[3-methyl-4-(3-fluorpyrrolidin-1-yl-carbonyl)-phenylcarbamoyl]-ethyl}-amide, (6) 5-bromo-thiophene-2-carboxylic acid-N-{1-methyl-1-[3-methyl-4-(2-methylpyrrolidin-1-yl-carbonyl)-phenylcarbamoyl]-ethyl}-amide, (7) 5-bromo-thiophene-2-carboxylic acid-N-{1-methyl-1-[3-methyl-4-(piperidin-1-yl-carbonyl)-phenylcarbamoyl]-ethyl}-amide, (8) 5-bromo-thiophene-2-carboxylic acid-N-{1-methyl-1-[3-methyl-4-(morpholin-4-yl-carbonyl)-phenylcarbamoyl]-ethyl}-amide, (9) 5-bromo-thiophene-2-carboxylic acid-N-{1-methyl-1-[3-chloro-4-(morpholin-4-yl-carbonyl)-phenylcarbamoyl]-ethyl}-amide,

(10) 5-bromo-thiophene-2-carboxylic acid-N-{1-methyl-1-[3-methyl-4-(1-methypiperazin-4-yl-carbonyl)-phenylcarbamoyl]-ethyl}-amide,

(11) 5-bromo-thiophene-2-carboxylic acid-N-{1-methyl-1-[3-methyl-4-(1-methyl-1,4-diazepan-4-yl-carbonyl)-phenylcarbamoyl]-ethyl}-amide,

(12) 5-bromo-thiophene-2-carboxylic acid-N-{1-[3-methyl-4-(2,2-dimethyl-pyrrolidin-1-yl-carbonyl)-phenylcarbamoyl]-cyclopentyl}-amide,

(13) 5-bromo-thiophene-2-carboxylic acid-N-{3-[3-chloro-4-(2-oxo-piperazin-4-yl-carbonyl)-phenylcarbamoyl]-tetrahydrofuran-3-yl}-amide,

(14) 5-bromo-thiophene-2-carboxylic acid-N-{3-[3-chloro-4-(pyrrolidin-1-yl-carbonyl)-phenylcarbamoyl]-tetrahydrofuran-3-yl}-amide,

(15) 5-bromo-thiophene-2-carboxylic acid-N-{4-[3-bromo-4-(2-oxo-piperazin-4-yl-carbonyl)-phenylcarbamoyl]-tetrahydropyran-4-yl}-amide,

(16) 5-bromo-thiophene-2-carboxylic acid-N-{4-[3-bromo-4-(pyrrolidin-1-yl-carbonyl)-phenylcarbamoyl]-tetrahydropyran-4-yl}-amide,

(17) 5-bromo-thiophene-2-carboxylic acid-N-{1-methyl-4-[3-trifluoromethyl-4-(2-oxo-piperazin-4-yl-carbonyl)-phenylcarbamoyl]-piperazin-4-yl}-amide,

(18) 5-bromo-thiophene-2-carboxylic acid-N-{1-methyl-4-[3-chloro-4-(pyrrolidin-1-yl-carbonyl)-phenylcarbamoyl]-piperazin-4-yl}-amide,

(19) 5-bromo-thiophene-2-carboxylic acid-N-{1-[3-methoxy-4-(2-oxo-piperazin-4-yl-carbonyl)-phenylcarbamoyl]-cycloheptyl}-amide,

(20) 5-chloro-thiophene-2-carboxylic acid-N-{3-[3-methyl-4-((2S)-2-hydroxymethyl-pyrrolidin-1-yl-carbonyl)-phenylcarbamoyl]-tetrahydrofuran-3-yl}-amide,

(21) 5-chloro-thiophene-2-carboxylic acid-N-{3-[3-methyl-4-((2S)-2-{pyrrolidin-1-yl-methyl}-pyrrolidin-1-yl-carbonyl)-phenylcarbamoyl]-tetrahydrofuran-3-yl}-amide,

(22) 5-chloro-thiophene-2-carboxylic acid-N-{3-[3-methyl-4-(3-oxo-piperazin-1-yl-carbonyl)-phenylcarbamoyl]-tetrahydrofuran-3-yl}-amide,

(23) 5-chloro-thiophene-2-carboxylic acid-N-{3-[3-methyl-4-(5-oxo-[1,4]diazepan-1-yl-carbonyl)-phenylcarbamoyl]-tetrahydrofuran-3-yl}-amide,

(24) 5-chloro-thiophene-2-carboxylic acid-N-{3-[3-methyl-4-(3-oxo-[1,4]diazepan-1-yl-carbonyl)-phenylcarbamoyl]-tetrahydrofuran-3-yl}-amide,

(25) 5-chloro-thiophene-2-carboxylic acid-N-{3-[3-methyl-4-(4-formyl-piperazin-1-yl-carbonyl)-phenylcarbamoyl]-tetrahydrofuran-3-yl}-amide,

(26) 5-chloro-thiophene-2-carboxylic acid-N-{3-[3-methyl-4-(4-acetyl-piperazin-1-yl-carbonyl)-phenylcarbamoyl]-tetrahydrofuran-3-yl}-amide,

(27) 5-bromo-thiophene-2-carboxylic acid-N-{3-[3-methyl-4-((2S)-2-hydroxymethyl-pyrrolidin-1-yl-carbonyl)-phenylcarbamoyl]-tetrahydrofuran-3-yl}-amide,

(28) 5-bromo-thiophene-2-carboxylic acid-N-{3-[3-methyl-4-((2S)-2-{pyrrolidin-1-yl-methyl}-pyrrolidin-1-yl-carbonyl)-phenylcarbamoyl]-tetrahydrofuran-3-yl}-amide,

(29) 5-bromo-thiophene-2-carboxylic acid-N-{3-[3-methyl-4-(3-oxo-piperazin-1-yl-carbonyl)-phenylcarbamoyl]-tetrahydrofuran-3-yl}-amide,

(30) 5-bromo-thiophene-2-carboxylic acid-N-{3-[3-methyl-4-(5-oxo-[1,4]diazepan-1-yl-carbonyl)-phenylcarbamoyl]-tetrahydrofuran-3-yl}-amide,

(31) 5-bromo-thiophene-2-carboxylic acid-N-{3-[3-methyl-4-(3-oxo-[1,4]diazepan-1-yl-carbonyl)-phenylcarbamoyl]-tetrahydrofuran-3-yl}-amide,

(32) 5-bromo-thiophene-2-carboxylic acid-N-{3-[3-methyl-4-(4-formyl-piperazin-1-yl-carbonyl)-phenylcarbamoyl]-tetrahydrofuran-3-yl}-amide,

(33) 5-bromo-thiophene-2-carboxylic acid-N-{3-[3-methyl-4-(4-acetyl-piperazin-1-yl-carbonyl)-phenylcarbamoyl]-tetrahydrofuran-3-yl}-amide,

(34) 5-bromo-thiophene-2-carboxylic acid-N-{2-[3-chloro-4-((2S)-2-{pyrrolidin-1-yl-methyl}-pyrrolidin-1-yl-carbonyl)-phenylcarbamoyl]-bicyclo[2.2.1]hept-2-yl}-amide,

(35) 5-chloro-thiophene-2-carboxylic acid-N-{3-[3-chloro-4-(3-oxo-piperazin-1-yl-carbonyl)-phenylcarbamoyl]-tetrahydrofuran-3-yl}-amide,

(36) 5-chloro-thiophene-2-carboxylic acid-N-{2-[3-methyl-4-(5-oxo-[1,4]diazepan-1-yl-carbonyl)-phenylcarbamoyl]-7-oxa-bicyclo[2.2.1]hept-2-yl}-amide,

(37) 5-chloro-thiophene-2-carboxylic acid-N-{2-[3-methyl-4-(3-oxo-[1,4]diazepan-1-yl-carbonyl)-phenylcarbamoyl]-bicyclo[2.2.1]hept-2-yl}-amide,

(38) 5-chloro-thiophene-2-carboxylic acid-N-{2-[4-(4-formyl-piperazin-1-yl-carbonyl)-phenylcarbamoyl]-7-oxa-bicyclo[2.2.1]hept-2-yl}-amide,

(39) 5-chloro-thiophene-2-carboxylic acid-N-{2-[3-chloro-4-(4-acetyl-piperazin-1-yl-carbonyl)-phenylcarbamoyl]-7-oxa-bicyclo[2.2.1]hept-2-yl}-amide,

Example 7

5-bromo-thiophene-2-carboxylic acid-N-{1-[3-methyl-4-(pyrrolidin-1-yl-carbonyl)-phenylcarbamoyl]-cyclopentyl}-amide

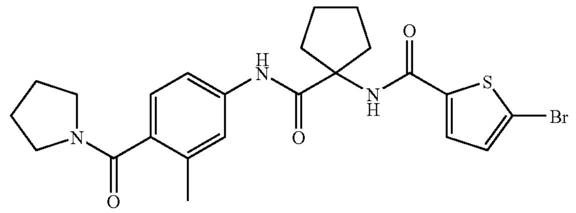

(a) methyl 1-[(5-bromo-thiophene-2-carbonyl)-amino]-cyclopentanecarboxylate

Prepared analogously to Example 2f from 5-bromo-thiophene-2-carboxylic acid and methyl 1-amino-cyclopentanecarboxylate with thionyl chloride and TEA in dichloromethane.

Yield: 87%

$R_f$ value: 0.91 (silica gel; dichloromethane/methanol=9:1)

$C_{12}H_{14}BrNO_3S$ (332.22)

Mass spectrum: $(M+H)^+$=332/334 (bromine isotope)

(b) 1-[(5-bromo-thiophene-2-carbonyl)-amino]-cyclopentanecarboxylic acid

Prepared analogously to Example 1d from methyl 1-[(5-bromo-thiophene-2-carbonyl)-amino]-cyclopentanecarboxylate with 1-molar aqueous sodium hydroxide solution in methanol at 55° C.

Yield: 52%

$R_f$ value: 0.31 (silica gel; dichloromethane/methanol=9:1)

$C_{11}H_{12}BrNO_3S$ (318.19)

Mass spectrum: $(M+H)^+$=318/320 (bromine isotope)

(c) 5-bromo-thiophene-2-carboxylic acid-N-{1-[3-methyl-4-(pyrrolidin-1-yl-carbonyl)-phenylcarbamoyl]-cyclopentyl}-amide 257.0 mg (0.81 mmol) 1-[(5-bromo-thiophene-2-carbonyl)-amino]-cyclopentanecarboxylic acid are combined with 307.0 mg (0.81 mmol) HATU and 202.0 µl (1.84 mmol) NMM in 2 ml DMF with stirring at ambient temperature and stirred for 30 min. Then 150.0 mg (0.73 mmol) (3-methyl-4-(pyrrolidin-1-yl-carbonyl)-aniline are added and the mixture is stirred overnight at 85° C. Sodium hydrogen carbonate solution is added to the reaction mixture and extracted with ethyl acetate. The combined organic phases are washed with 0.5-molar potassium hydrogen sulphate solution and sat. sodium chloride solution. After drying over magnesium sulphate and evaporation i. vac. the residue is purified by chromatography on silica gel (eluant gradient: dichloromethane/methanol=98:2->90:10).

Yield: 205.0 mg (55%)

$R_f$ value: 0.45 (silica gel; dichloromethane/methanol=9:1)

$C_{23}H_{26}BrN_3O_3S$ (504.44)

Mass spectrum: $(M+H)^+$=504/506 (bromine isotope)

Example 8

5-chloro-thiophene-2-carboxylic acid-N-{(1R)-1-[3-chloro-4-(pyrrolidin-1-yl-carbonyl)-phenylcarbamoyl]-ethyl}-amide

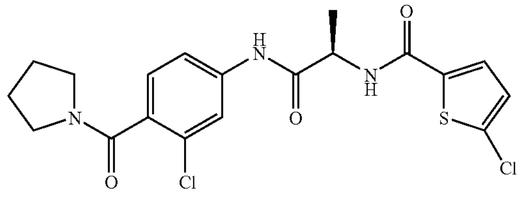

(a) tert.-butyl(R)-2-[(5-chloro-thiophene-2-carbonyl)-amino]-propionate

Prepared analogously to Example 1a from tert.-butyl 5-chloro-thiophene-2-carboxylic acid and (R)-2-amino-propionate with TBTU and NMM in THF.

Yield: 98%

$R_f$ value: 0.75 (silica gel; petroleum ether/ethyl acetate=1:1)

$C_{12}H_{16}ClNO_3S$ (289.78)

(b) (R)-2-[(5-chloro-thiophene-2-carbonyl)-amino]-propionic acid

Prepared analogously to Example 2e from tert.-butyl(R)-2-[(5-chloro-thiophene-2-carbonyl)-amino]-propionate with TFA in dichloromethane.

Yield: 69%

$R_f$ value: 0.0-0.3 (silica gel; ethyl acetate/petroleum ether=4:1)

$C_8H_8ClNO_3S$ (233.67)

Mass spectrum: $(M+H)^+$=234/236 (chlorine isotope)

(c) 5-chloro-thiophene-2-carboxylic acid-N-{(R)-1-[3-chloro-4-(pyrrolidine-1-carbonyl)-phenylcarbamoyl]-ethyl}-amide Prepared analogously to Example 1a from (R)-2-[(5-chloro-thiophene-2-carbonyl)-amino]-propionic acid and 3-chloro-4-(pyrrolidin-1-yl-carbonyl)-aniline with TBTU and NMM in DMF.

Yield: 23%

$R_f$ value: 0.2 (silica gel; ethyl acetate+1% conc. ammonia solution)

$C_{19}H_{19}Cl_2N_3O_3S$ (440.34)

Mass spectrum: $(M+H)^+$=438/440/442 (chlorine isotope)

Example 9

5-chloro-thiophene-2-carboxylic acid-N-{2-methoxy-1-[3-methyl-4-(pyrrolidin-1-yl-carbonyl)-phenylcarbamoyl]-ethyl}-amide

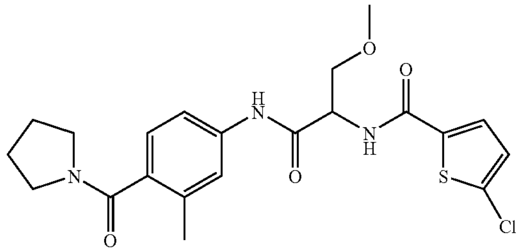

(a) 2-tert.-butoxycarbonylamino-3-methoxy-propionic acid 1.90 g (16.0 mmol) 2-amino-3-methoxy-propionic acid in 30 ml dioxane and 12.5 ml of water are combined with a solution of 7.10 g (32.5 mmol) di-tert.-butyldicarbonate in 20 ml 1,4-dioxane and stirred for 4.5 hours at 40° C. At ambient temperature 20 ml 2-molar aqueous sodium hydroxide solution is added and the mixture is stirred overnight. After filtering the filtrate is extracted with ethyl acetate. The aqueous phase is adjusted to pH 3.5 with acetic acid and extracted with ethyl acetate. The combined organic phases are washed with semisat. and sat. sodium chloride solution, dried over magnesium sulphate and evaporated down i. vac.

Yield: 2.10 g (60%)

$C_9H_{17}NO_5$ (219.24)

Mass spectrum: (M−H)-=218

(b) 2-Boc-amino-3-methoxy-N-[3-methyl-4-(pyrrolidine-1-carbonyl)-phenyl]-propionic acid-amide Prepared analogously to Example 1a from 2-tert.-butoxycarbonylamino-3-methoxy-propionic acid and 3-methyl-4-(pyrrolidin-1-yl-carbonyl)-aniline with TBTU and NMM in DMF.

Yield: quant.

$R_f$ value: 0.55 (silica gel; ethyl acetate/ethanol=9:1)

$C_{21}H_{31}N_3O_5$ (405.49)

Mass spectrum: $(M+H)^+$=406

(c) 2-amino-3-methoxy-N-[3-methyl-4-(pyrrolidine-1-carbonyl)-phenyl]-propionic acid-amide Prepared analogously to Example 3b from 2-Boc-amino-3-methoxy-N-[3-methyl-4-(pyrrolidine-1-carbonyl)-phenyl]-propionic acid-amide and 6-molar hydrochloric acid in dioxane.

Yield: 74%

$R_f$ value: 0.1 (silica gel; ethyl acetate/ethanol=9:1)

$C_{16}H_{23}N_3O_3$ (305.37)

(d) 5-chloro-thiophene-2-carboxylic acid-N-{2-methoxy-1-[3-methyl-4-(pyrrolidin-1-yl-carbonyl)-phenylcarbamoyl]-ethyl}-amide Prepared analogously to Example 1a from 5-chloro-thiophene-2-carboxylic acid and 2-amino-3-methoxy-N-[3-methyl-4-(pyrrolidine-1-carbonyl)-phenyl]-propionamide with TBTU and TEA in DMF.

Yield: (60%)

$R_f$ value: 0.45 (silica gel; ethyl acetate/ethanol=9:1)

$C_{21}H_{24}ClN_3O_5S$ (449.95)

Mass spectrum: $(M+H)^+$=450/452 (chlorine isotope)

Example 10

5-chloro-thiophene-2-carboxylic acid-N-{(1R)-1-phenyl-1-[3-methyl-4-(pyrrolidin-1-yl-carbonyl)-phenylcarbamoyl]-methyl}-amide

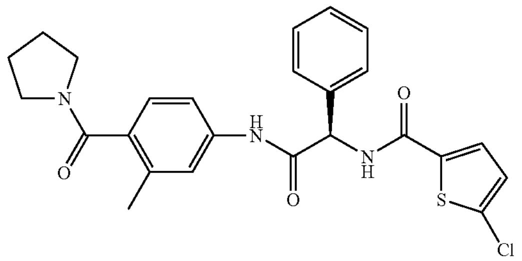

(a) ethyl(R)-[(5-chloro-thiophene-2-carbonyl)-amino]-phenyl-acetate

Prepared analogously to Example 1a from 5-chloro-thiophene-2-carboxylic acid and ethyl(R)-amino-phenyl-acetate with TBTU and NMM in THF.

Yield: 96%

$R_f$ value: 0.61 (silica gel; dichloromethane/ethanol=98:2)

$C_{15}H_{14}ClNO_3S$ (323.80)

Mass spectrum: $(M+H)^+$=324/326 (chlorine isotope)

(b) (R)-[(5-chloro-thiophene-2-carbonyl)-amino]-phenyl-acetic acid

Prepared analogously to Example 1d from ethyl(R)-[(5-chloro-thiophene-2-carbonyl)-amino]-phenyl-acetate with 1-molar aqueous sodium hydroxide solution in ethanol.

Yield: 96%

$R_f$ value: 0.10 (silica gel; dichloromethane/ethanol=9:1)

$C_{13}H_{10}ClNO_3S$ (295.74)

Mass spectrum: $(M+H)^+$=296/298 (chlorine isotope)

(c) 5-chloro-thiophene-2-carboxylic acid-N-{(1R)-1-phenyl-1-[3-methyl-4-(pyrrolidin-1-yl-carbonyl)-phenylcarbamoyl]-methyl}-amide 300.0 mg (1.01 mmol) (R)-[(5-chloro-thiophene-2-carbonyl)-amino]-phenyl-acetic acid, 207.0 mg (1.01 mmol) (3-methyl-4-(pyrrolidin-1-yl-carbonyl)-aniline and 335.0 µl (3.04 mmol) NMM in 60 ml dichloromethane are combined at 0° C. with 1.19 ml (2.03 mmol) PPA (50% in ethyl acetate) and stirred overnight at ambient temperature. After evaporation i. vac. the residue is purified by chromatography on silica gel (eluant gradient: dichloromethane/ethanol=100:0->94:6).

Yield: 180.0 mg (37%)

$R_f$ value: 0.61 (silica gel; dichloromethane/ethanol=9:1)

$C_{25}H_{24}ClN_3O_3S$ (482.00)

Mass spectrum: $(M+H)^+$=482/484 (chlorine isotope)

Example 12

5-bromo-thiophene-2-carboxylic acid-N-{1-methyl-1-[4-(pyrrolidin-1-yl-carbonyl)-phenylcarbamoyl]-ethyl}-amide

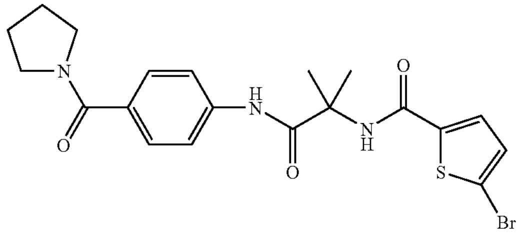

(a) 4-(pyrrolidin-1-yl-carbonyl)-nitro-benzene

Prepared analogously to Example 1a from 4-nitrobenzoic acid and pyrrolidine with TBTU and TEA in THF.

Yield: quant.

$R_f$ value: 0.36 (silica gel; dichloromethane/ethanol=95:5)

$C_{11}H_{12}N_2O_3$ (220.23)

Mass spectrum: $(M+H)^+$=221

(b) 4-(pyrrolidin-1-yl-carbonyl)-aniline

Prepared analogously to Example 6b from 4-(pyrrolidin-1-yl-carbonyl)-nitro-benzene by hydrogenation with hydrogen with Pd/C 10% in methanol.

Yield: quant.

$R_f$ value: 0.33 (silica gel; dichloromethane/ethanol=95:5)

$C_{11}H_{14}N_2O$ (190.24)

Mass spectrum: $(M+H)^+$=191

(c) 5-bromo-thiophene-2-carboxylic acid-N-{-1-methyl-1-[4-(pyrrolidin-1-yl-carbonyl)-phenylcarbamoyl]-ethyl}-amide Prepared analogously to Example 10c from 2-[(5-bromo-thiophene-2-carbonyl)-amino]-2-methyl-propionic acid and 4-(pyrrolidin-1-yl-carbonyl)-aniline with PPA and NMM in dichloromethane.

Yield: 65%

$R_f$ value: 0.26 (silica gel; dichloromethane/ethanol=95:5)

$C_{20}H_{22}BrN_3O_3S$ (464.38)

Mass spectrum: $(M+H)^+$=464/466 (bromine isotope)

Example 13

5-bromo-thiophene-2-carboxylic acid-N-{(1R)-2-[1-methyl-1H-imidazol-4-yl]-1-[3-methyl-4-(pyrrolidin-1-yl-carbonyl)-phenylcarbamoyl]-ethyl}-amide

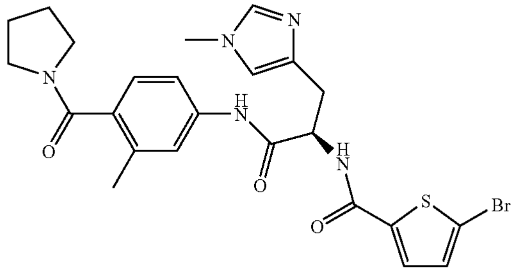

(a) (2R)-2-Boc-amino-3-(1-methyl-1H-imidazol-4-yl)-N-[3-methyl-4-(pyrrolidin-1-yl-carbonyl)-phenyl]-propionic acid-amide Prepared analogously to Example 1a from (R)-2-tert.-butoxycarbonylamino-3-(1-methyl-1H-imidazol-4-yl)-propionic acid and 3-methyl-4-(pyrrolidin-1-yl-carbonyl)-aniline with TBTU and DIPEA in THF.

Yield: quant.

$R_f$ value: 0.66 (silica gel; dichloromethane/ethanol=8:2)

$C_{24}H_{33}N_5O_4$ (455.55)

Mass spectrum: $(M+H)^+$=456

(b) (2R)-2-amino-3-(1-methyl-1H-imidazol-4-yl)-N-[3-methyl-4-(pyrrolidin-1-yl-carbonyl)-phenyl]-propionamide-triflate Prepared analogously to Example 2e from (2R)-2-Boc-amino-3-(1-methyl-1H-imidazol-4-yl)-N-[3-methyl-4-(pyrrolidin-1-yl-carbonyl)-phenyl]-propionic acid-amide with TFA in dichloromethane.

Yield: 57%

$R_f$ value: 0.20 (silica gel; dichloromethane/ethanol=8:2)

$C_{19}H_{25}N_5O_2$*$CF_3COOH$ (469.46/355.44)

Mass spectrum: $(M+CF_3COO)^-$=468

(c) 5-bromo-thiophene-2-carboxylic acid-N-{(1R)-2-[1-methyl-1H-imidazol-4-yl]-1-[3-methyl-4-(pyrrolidin-1-yl-carbonyl)-phenylcarbamoyl]-ethyl}-amide Prepared analogously to Example 10c from 5-bromo-thiophene-2-carboxylic acid and (2R)-2-amino-3-(1-methyl-1H-imidazol-4-yl)-N-[3-methyl-4-(pyrrolidine-1-carbonyl)-phenyl]-propionamide-triflate with PPA and NMM in THF.

Yield: 52%

$R_f$ value: 0.40 (silica gel; dichloromethane/ethanol=9:1)

$C_{24}H_{26}BrN_5O_3S$ (544.47)

Mass spectrum: $(M+H)^+$=544/546 (bromine isotope)

Example 16

5-bromo-thiophene-2-carboxylic acid-N-{(1R)-2-[1H-imidazol-4-yl]-1-[3-methyl-4-(pyrrolidin-1-yl-carbonyl)-phenylcarbamoyl]-ethyl}-amide

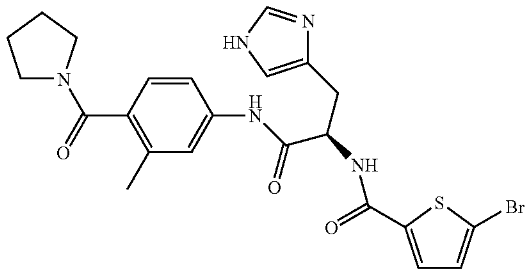

(a) (R)-2-Boc-amino-3-(1-benzyl-1H-imidazol-4-yl]-N-[3-methyl-4-(pyrrolidin-1-yl-carbonyl)-phenyl]-propionic acid-amide Prepared analogously to Example 1a from (R)-3-(1-benzyl-1H-imidazol-4-yl)-2-tert.-butoxycarbonylamino-propionic acid and 3-methyl-4-(pyrrolidin-1-yl-carbonyl)-aniline with TBTU and DIPEA in THF.

Yield: quant.

$R_f$ value: 0.56 (silica gel; dichloromethane/ethanol=9:1)

$C_{30}H_{37}N_5O_4$ (531.65)

Mass spectrum: $(M+H)^+$=532

(b) (R)-2-amino-3-(1-benzyl-1H-imidazol-4-yl)-N-[3-methyl-4-(pyrrolidin-1-yl-carbonyl)-phenyl]-propionamide Prepared analogously to Example 2e from (R)-2-Boc-amino-3-(1-benzyl-1H-imidazol-4-yl)-N-[3-methyl-4-(pyrrolidin-1-yl-carbonyl)-phenyl]-propionic acid-amide with TFA in dichloromethane.

Yield: 88%

$R_f$ value: 0.15 (silica gel; dichloromethane/ethanol=9:1)

$C_{25}H_{29}N_5O_2$ (431.53)

Mass spectrum: $(M+H)^+$=432

(c) (R)-2-amino-3-(1H-imidazol-4-yl)-N-[3-methyl-4-(pyrrolidin-1-yl-carbonyl)-phenyl]-propionamide 350.0 mg (0.81 mmol) (R)-2-amino-3-(1-benzyl-1H-imidazol-4-yl)-N-[3-methyl-4-(pyrrolidin-1-yl-carbonyl)-phenyl]-propionamide are dissolved in 10.0 ml acetic acid and combined with 150.0 mg $Pd(OH)_2$. The mixture is hydrogenated in a Parr apparatus at ambient temperature at 3 bar hydrogen pressure for eight hours. Then the catalyst is filtered off and the filtrate is evaporated down i. vac.

Yield: 210 mg (76%)

$C_{18}H_{23}N_5O_2$ (341.41)

Mass spectrum: $(M+H)^+=342$ (d) 5-bromo-thiophene-2-carboxylic acid-N-{(1R)-2-[1H-imidazol-4-yl]-1-[3-methyl-4-(pyrrolidin-1-yl-carbonyl)-phenylcarbamoyl]-ethyl}-amide Prepared analogously to Example 10c from 5-bromo-thiophene-2-carboxylic acid and (R)-2-amino-3-(1H-imidazol-4-yl)-N-[3-methyl-4-(pyrrolidin-1-yl-carbonyl)-phenyl]-propionamide with PPA and NMM in THF.

Yield: 4%

$R_t$ value: 5.5 min (HPLC-MS 2)

$C_{23}H_{24}BrN_5O_3S$ (530.44)

Mass spectrum: $(M+H)^+=530/532$ (bromine isotope)

Example 19

5-bromo-thiophene-2-carboxylic acid-N-{1-[3-methyl-4-(morpholin-4-yl-carbonyl)-phenylcarbamoyl]-cyclopent-1-yl}-amide

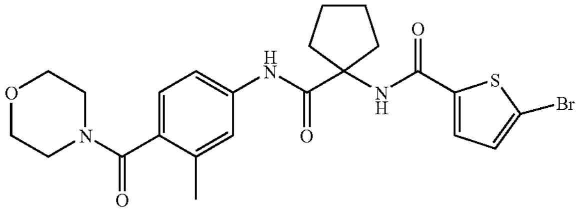

(a) N-[3-methyl-4-(morpholin-4-yl-carbonyl)-phenyl]-acetamide

Prepared analogously to Example 1a from 4-acetylamino-2-methyl-benzoic acid and morpholine with TBTU and TEA in THF.

Yield: 66%

$R_f$ value: 0.35 (silica gel; dichloromethane/methanol=9:1)

$C_{14}H_{18}N_2O_3$ (262.30)

Mass spectrum: $(M+H)^+=263$ (b) 3-methyl-4-(morpholin-4-yl-carbonyl)-aniline 700.0 mg (2.67 mmol) N-[3-methyl-4-(morpholin-4-yl-carbonyl)-phenyl]-acetamide are combined with 7 ml 4-molar sodium hydroxide solution and stirred overnight at 65° C. The reaction mixture is poured onto ice water and extracted with ethyl acetate. The organic phase is dried over magnesium sulphate and evaporated down i. vac.

Yield: 580.0 mg (99%)

$C_{12}H_{16}N_2O_2$ (220.27)

Mass spectrum: $(M+H)^+=221$ (c) 5-bromo-thiophene-2-carboxylic acid-N-{1-[3-methyl-4-(morpholin-4-yl-carbonyl)-phenylcarbamoyl]-cyclopent-1-yl}-amide Prepared analogously to Example 7c from 1-[(5-bromo-thiophene-2-carbonyl)-amino]-cyclopentanecarboxylic acid and 3-methyl-4-(morpholin-4-yl-carbonyl)-aniline with HATU and NMM in DMF.

Yield: 49%

$R_f$ value: 0.27 (silica gel; dichloromethane/methanol=9:1)

$C_{23}H_{26}BrN_3O_4S$ (520.44)

Mass spectrum: $(M+H)^+=520/522$ (bromine isotope)

Example 20

5-bromo-thiophene-2-carboxylic acid-N-{1-methyl-1-[2-fluoro-4-(pyrrolidin-1-yl-carbonyl)-phenylcarbamoyl]-ethyl}-amide

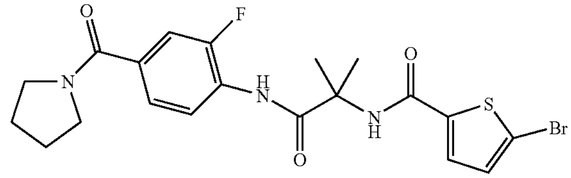

(a) 2-fluoro-4-(pyrrolidin-1-yl-carbonyl)-aniline

Prepared analogously to Example 1a from 4-amino-3-fluoro-benzoic acid and pyrrolidine with TBTU and TEA in DMF.

Yield: 58%

$R_f$ value: 0.70 (silica gel; ethyl acetate)

$C_{11}H_{13}FN_2O$ (208.23)

Mass spectrum: $(M+H)^+=209$ (b) 5-bromo-thiophene-2-carboxylic acid-N-{1-methyl-1-[2-fluoro-4-(pyrrolidin-1-yl-carbonyl)-phenylcarbamoyl]-ethyl}-amide Prepared analogously to Example 7c from 2-[(5-bromo-thiophene-2-carbonyl)-amino]-2-methyl-propionic acid and 2-fluoro-4-(pyrrolidin-1-yl-carbonyl)-aniline with HATU and NMM in DMF.

Yield: 4%

$R_f$ value: 0.53 (silica gel; ethyl acetate)

$C_{20}H_{21}BrFN_3O_3S$ (482.37)

Mass spectrum: $(M+H)^+=482/484$ (bromine isotope)

Example 21

5-bromo-thiophene-2-carboxylic acid-N-{1-methyl-1-[3-methyl-4-((2S)-2-hydroxymethyl-pyrrolidin-1-yl-carbonyl)-phenylcarbamoyl]-ethyl}-amide

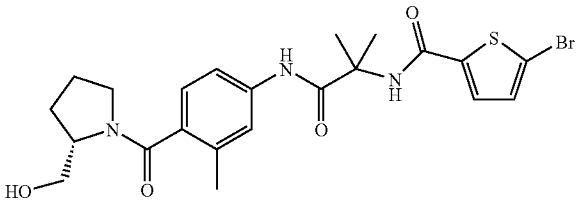

(a) methyl 4-amino-2-methyl-benzoate 20.0 g (0.10 mol) 4-acetylamino-2-methyl-benzoic acid in 200 ml of methanol are combined with 15 ml (0.28 mol) conc. sulphuric acid and refluxed for 3 hours with stirring. After evaporation i. vac. the residue is poured onto ice water and adjusted to pH 9 with sodium hydrogen carbonate solution. The precipitate is filtered off and dried at 40° C. in the vacuum drying cupboard.

Yield: 15.1 g (88%)

$R_f$ value: 0.81 (silica gel; dichloromethane/methanol 9:1)

$C_9H_{11}NO_2$ (165.19)

Mass spectrum: $(M+H)^+$=166

(b) 4-{2-[(5-bromo-thiophene-2-carbonyl)-amino]-2-methyl-propionylamino}-2-methyl-benzoic acid-methylester Prepared analogously to Example 7c from 2-[(5-bromo-thiophene-2-carbonyl)-amino]-2-methyl-propionic acid and methyl 4-amino-2-methyl-benzoate with HATU and NMM in DMF.

Yield: 80%

$R_f$ value: 0.62 (silica gel; dichloromethane/methanol 9:1)

$C_{18}H_{19}BrN_2O_4S$ (439.33)

Mass spectrum: $(M+H)^+$=439/441 (bromine isotope)

(c) 4-{2-[(5-bromo-thiophene-2-carbonyl)-amino]-2-methyl-propionylamino}-2-methyl-benzoic acid Prepared analogously to Example 1d from methyl 4-{2-[(5-bromo-thiophene-2-carbonyl)-amino]-2-methyl-propionylamino}-2-methyl-benzoate with 1-molar sodium hydroxide solution in methanol.

Yield: 69%

$R_f$ value: 0.31 (silica gel; dichloromethane/methanol 9:1)

$C_{17}H_{17}BrN_2O_4S$ (425.30)

Mass spectrum: $(M+H)^+$=425/427 (bromine isotope)

(d) 5-bromo-thiophene-2-carboxylic acid-N-{1-methyl-1-[3-methyl-4-((2S)-2-hydroxymethyl-pyrrolidin-1-yl-carbonyl)-phenylcarbamoyl]-ethyl}-amide Prepared analogously to Example 1a from 4-{2-[(5-bromo-thiophene-2-carbonyl)-amino]-2-methyl-propionylamino}-2-methyl-benzoic acid and (S)-2-hydroxymethyl-pyrrolidine with TBTU and TEA in DMF.

Yield: 46%

$R_f$ value: 0.70 (silica gel; ethyl acetate/ethanol 8:2+1% acetic acid)

$C_{22}H_{26}BrN_3O_4S$ (508.43)

Mass spectrum: $(M+H)^+$=508/510 (bromine isotope)

The following compounds were prepared analogously:

| No. | Structural formula / Name | Yield | Mass peak(s) | $R_f$ value or $R_t$ |
|---|---|---|---|---|
| 22 | 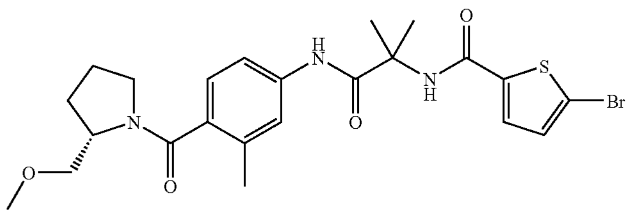 5-bromo-thiophene-2-carboxylic acid-N-{1-methyl-1-[3-methyl-4-((2S)-2-methoxymethyl-pyrrolidin-1-yl-carbonyl)-phenylcarbamoyl]-ethyl}-amide | Σ: 18% | $(M + H)^+$ = 522/524 (bromine isotope) | 0.52 (silica gel; ethyl acetate/ethanol = 8:2 + 1% acetic acid) |
| 23 | 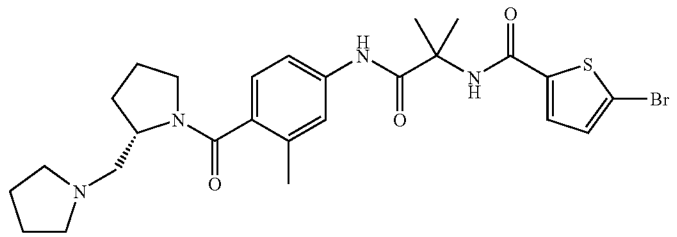 5-bromo-thiophene-2-carboxylic acid-N-{1-methyl-1-[3-methyl-4-((2S)-2-{pyrrolidin-1-yl-methyl}-pyrrolidin-1-yl-carbonyl)-phenylcarbamoyl]-ethyl}-amide | Σ: 11% | $(M + H)^+$ = 561/563 (bromine isotope) | 0.38 (RP-(C18); 5% NaCl solution/methanol = 2:3) |

-continued

| No. | Structural formula<br>Name | Yield | Mass peak(s) | $R_f$-value or $R_t$ |
|---|---|---|---|---|
| 24 | 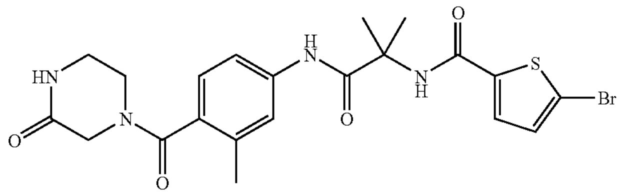<br>5-bromo-thiophene-2-carboxylic acid-N-{1-methyl-1-[3-methyl-4-(3-oxo-piperazln-1-yl-carbonyl)-phenylcarbamoyl]-ethyl}-amide | Σ: 18% | $(M + H)^+$ = 507/509 (bromine isotope) | 0.42 (silica gel; ethyl acetate/ethanol = 8:2 + 1% acetic acid) |
| 25 | 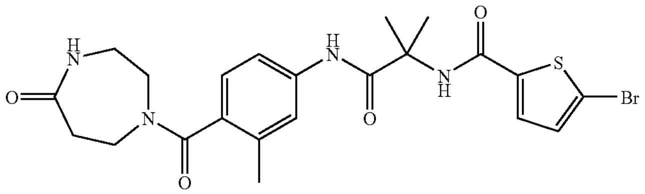<br>5-bromo-thiophene-2-carboxylic acid-N-{1-methyl-1-[3-methyl-4-(5-oxo-[1,4]diazepan-1-yl-carbonyl)-phenylcarbamoyl]-ethyl}-amide | Σ: 12% | $(M + H)^+$ = 521/523 (bromine isotope) | 0.33 (silica gel; ethyl acetate/ethanol = 8:2 + 1% acetic acid) |
| 26 | 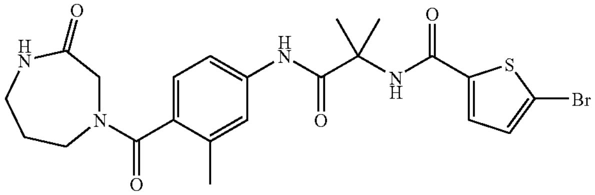<br>5-bromo-thiophene-2-carboxylic acid-N-{1-methyl-1-[3-methyl-4-(3-oxo-[1,4]diazepan-1-yl-carbonyl)-phenylcarbamoyl]-ethyl}-amide | Σ: 15% | $(M + H)^+$ = 521/523 (bromine isotope) | 0.32 (silica gel; ethyl acetate/ethanol = 9:1 + 1% ammonia) |
| 27 | 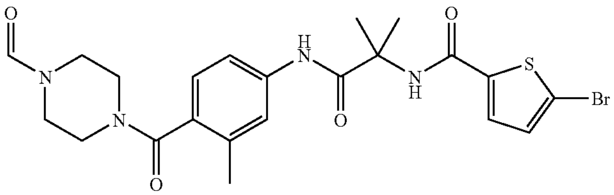<br>5-bromo-thiophene-2-carboxylic acid-N-{1-methyl-1-[3-methyl-4-(4-formyl-piperazin-1-yl-carbonyl)-phenylcarbamoyl]-ethyl}-amide | Σ: 16% | $(M + H)^+$ = 521/523 (bromine isotope) | 0.41 (silica gel; ethyl acetate/ethanol = 9:1 + 1% ammonia) |
| 28 | 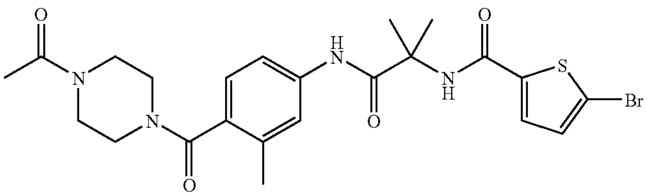<br>5-bromo-thiophene-2-carboxylic acid-N-{1-methyl-1-[3-methyl-4-(4-acetyl-piperazin-1-yl-carbonyl)-phenylcarbamoyl]-ethyl}-amide, | Σ: 16% | $(M + H)^+$ = 535/537 (bromine isotope) | 0.39 (silica gel; ethyl acetate/ethanol = 9:1 + 1% ammonia) |

-continued

| No. | Structural formula / Name | Yield | Mass peak(s) | $R_f$-value or $R_t$ |
|---|---|---|---|---|
| 29 | 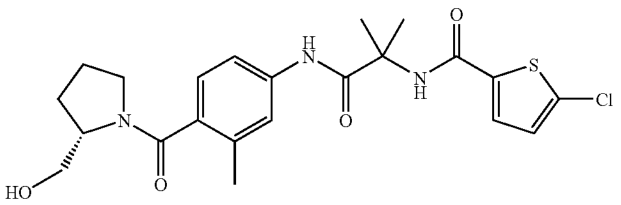 5-chloro-thiophene-2-carboxylic acid-N-{1-methyl-1-[3-methyl-4-((2S)-2-hydroxymethyl-pyrrolidin-1-yl-carbonyl)-phenylcarbamoyl]-ethyl}-amide, | Σ: 22% | $(M + H)^+$ = 464/466 (chlorine isotope) | 0.59 (silica gel; ethyl acetate/ethanol = 8:2 + 1% ammonia) |
| 30 | 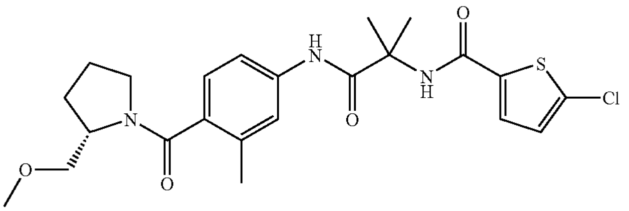 5-chloro-thiophene-2-carboxylic acid-N-{1-methyl-1-[3-methyl-4-((2S)-2-methoxymethyl-pyrrolidin-1-yl-carbonyl)-phenylcarbamoyl]-ethyl}-amide, | Σ: 30% | $(M + H)^+$ = 478/480 (chlorine isotope) | 0.58 (silica gel; ethyl acetate/ethanol = 8:2 + 1% ammonia) |
| 31 | 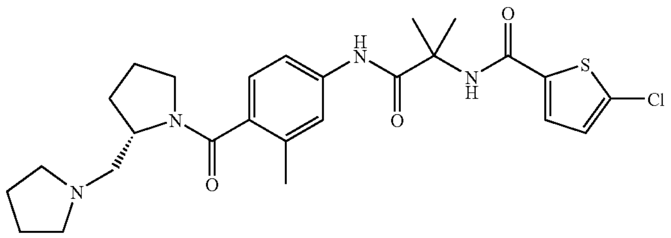 5-chloro-thiophene-2-carboxylic acid-N-{1-methyl-1-[3-methyl-4-((2S)-2-{pyrrolidin-1-yl-methyl}-pyrrolidin-1-yl-carbonyl)-phenylcarbamoyl]-ethyl}-amide, | Σ: 16% | $(M + H)^+$ = 517/519 (chlorine isotope) | 0.39 (RP-(C18); 5% NaCl solution/ methanol = 2:3) |
| 32 | 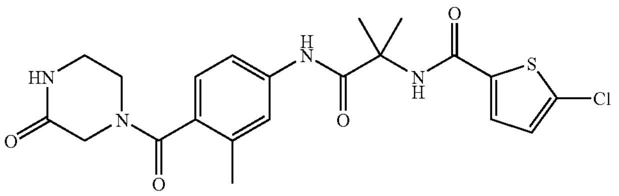 5-chloro-thiophene-2-carboxylic acid-N-{1-methyl-1-[3-methyl-4-((2S)-2-methoxymethyl-pyrrolidin-1-yl-carbonyl)-phenylcarbamoyl]-ethyl}-amide, | Σ: 1% | $(M + H)^+$ = 463/465 (chlorine isotope) | 0.36 (silica gel; ethyl acetate/ethanol = 8:2 + 1% ammonia) |
| 33 | 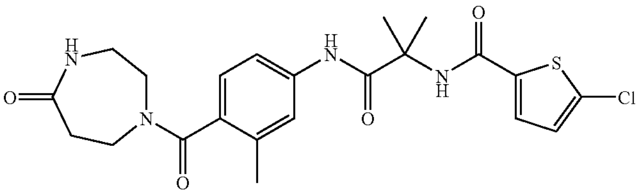 5-chloro-thiophene-2-carboxylic acid-N-{1-methyl-1-[3-methyl-4-(5-oxo-[1,4]diazepan-1-yl-carbonyl)-phenylcarbamoyl]-ethyl}-amide, | Σ: 32% | $(M + H)^+$ = 477/479 (chlorine isotope) | 0.34 (silica gel; ethyl acetate/ethanol = 8:2 + 1% ammonia) |

-continued

| No. | Structural formula / Name | Yield | Mass peak(s) | $R_f$-value or $R_t$ |
| --- | --- | --- | --- | --- |
| 34 | 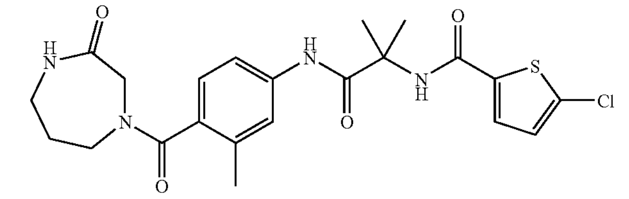 5-chloro-thiophene-2-carboxylic acid-N-{1-methyl-1-[3-methyl-4-(3-oxo-[1,4]diazepan-1-yl-carbonyl)-phenylcarbamoyl]-ethyl}-amide | Σ: 32% | $(M + H)^+$ = 477/479 (chlorine isotope) | 0.32 (silica gel; ethyl acetate/ethanol = 8:2 + 1% ammonia) |
| 35 | 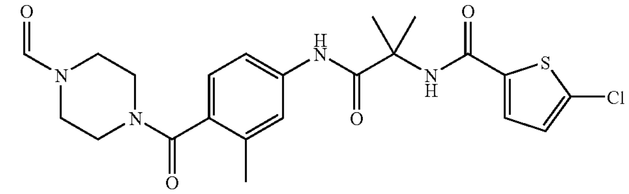 5-chloro-thiophene-2-carboxylic acid-N-{1-methyl-1-[3-methyl-4-(4-formyl-piperazin-1-yl-carbonyl)-phenylcarbamoyl]-ethyl}-amide | Σ: 30% | $(M + H)^+$ = 477/479 (chlorine isotope) | 0.35 (silica gel; ethyl acetate/ethanol = 8:2 + 1% ammonia) |
| 36 | 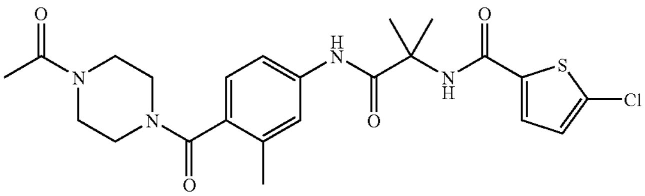 5-chloro-thiophene-2-carboxylic acid-N-{1-methyl-1-[3-methyl-4-(4-acetyl-piperazin-1-yl-carbonyl)-phenylcarbamoyl]-ethyl}-amide | Σ: 32% | $(M + H)^+$ = 491/493 (chlorine isotope) | 0.34 (silica gel; ethyl acetate/ethanol = 8:2 + 1% ammonia) |

Example 37

5-chloro-thiophene-2-carboxylic acid-N-{1-methyl-1-[3-methyl-4-(2-{3-hydroxy-prop-1-yl}-piperidin-1-yl-carbonyl)-phenylcarbamoyl]-ethyl}-amide

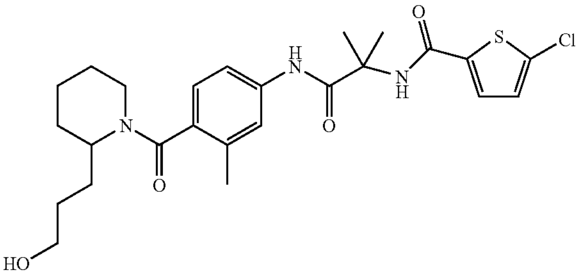

200 μl of a 0.05 molar solution of 4-{2-[(5-chloro-thiophene-2-carbonyl)-amino]-2-methyl-propionylamino}-2-methyl-benzoic acid, which additionally contains 0.05 mol/l DIPEA, in DMF are combined with 100 μl of a 0.1-molar solution of TBTU in DMF on a microtitre plate and mixed for 10 mins on a shaker. Then 200 μl of a 0,05-molar solution of (3-hydroxy-prop-1-yl)-piperidine, which additionally contains 0.05 mol/l DIPEA, are pipetted in and again mixed in by shaking. After 16 h at ambient temperature the mixture is filtered through basic aluminium oxide and washed with DMF/methanol=9:1. Then it is evaporated down i. vac.

$R_t$ value: 3.77 min (HPLC-MS 2)

$C_{25}H_{32}ClN_3O_4S$ (506.06)

Mass spectrum: $(M+H)^+$=507.07

The following compounds were prepared analogously:

| No. | Structural formula<br>Name | Mass peak(s) | $R_f$ value or $R_t$ |
|---|---|---|---|
| 38 | 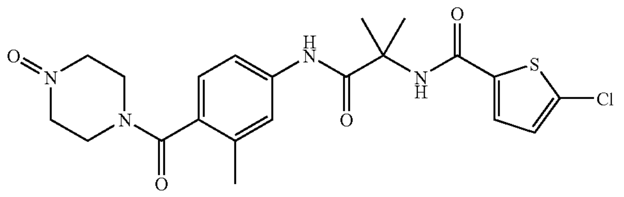<br>5-chloro-thiophene-2-carboxylic acid-N-{1-methyl-1-[3-methyl-4-(1-oxo-thiomorpholin-4-yl-carbonyl)-phenylcarbamoyl]-ethyl}-amide | $(M + H)^+$ = 483.03 | 3.35 min (HPLC-MS 2) |
| 39 | 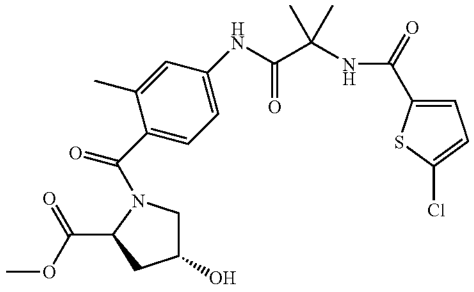<br>5-chloro-thiophene-2-carboxylic acid-N-{1-methyl-1-[3-methyl-4-((2S,4R)-2-methoxycarbonyl-4-hydroxy-pyrrolidin-1-yl-carbonyl)-phenylcarbamoyl]-ethyl}-amide | $(M + H)^+$ = 509.00 | 3.51 min (HPLC-MS 2) |
| 40 | 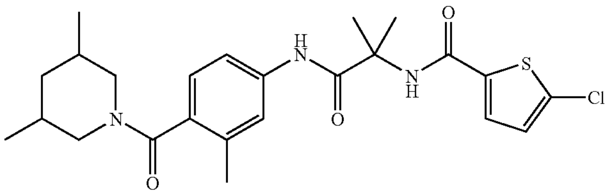<br>5-chloro-thiophene-2-carboxylic acid-N-{1-methyl-1-[3-methyl-4-(3,5-dimethyl-piperidin-1-yl-carbonyl)-phenylcarbamoyl]-ethyl}-amide | $(M + H)^+$ = 477.05 | 4.35 min (HPLC-MS 2) |
| 41 | 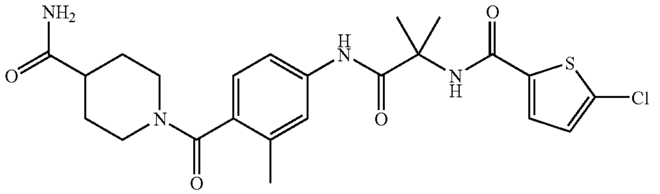<br>5-chloro-thiophene-2-carboxylic acid-N-{1-methyl-1-(3-methyl-4-(4-aminocarbonyl-piperidin-1-yl-carbonyl)-phenylcarbamoyl]-ethyl}-amide | $(M + H)^+$ = 492.02 | 3.36 min (HPLC-MS 2) |
| 42 | 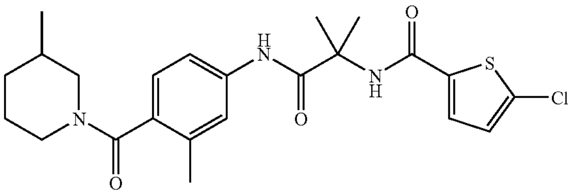<br>5-chloro-thiophene-2-carboxylic acid-N-{1-methyl-1-[3-methyl-4-(3-methyl-piperidin-1-yl-carbonyl)-phenylcarbamoyl]-ethyl}-amide | $(M + H)^+$ = 463.02 | 4.17 min (HPLC-MS 2) |

-continued

| No. | Structural formula / Name | Mass peak(s) | $R_f$-value or $R_t$ |
|---|---|---|---|
| 43 | 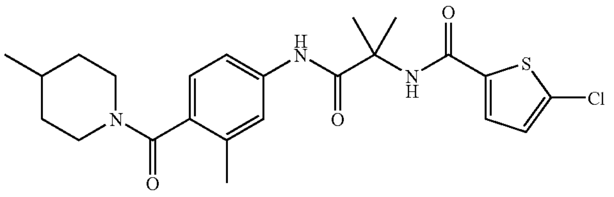 5-chloro-thiophene-2-carboxylic acid-N-{1-methyl-1-[3-methyl-4-(4-methyl-piperidin-1-yl-carbonyl)-phenylcarbamoyl]-ethyl}-amide | $(M + H)^+$ = 463.02 | 4.19 min (HPLC-MS 2) |
| 44 | 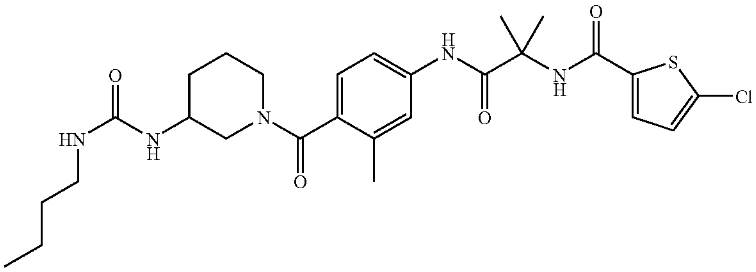 5-chloro-thiophene-2-carboxylic acid-N-{1-methyl-1-[3-methyl-4-(3-{3-butyl-ureido}-piperidin-1-yl-carbonyl)-phenylcarbamoyl]-ethyl}-amide | $(M + H)^+$ = 563.14 | 3.83 min (HPLC-MS 2) |
| 45 | 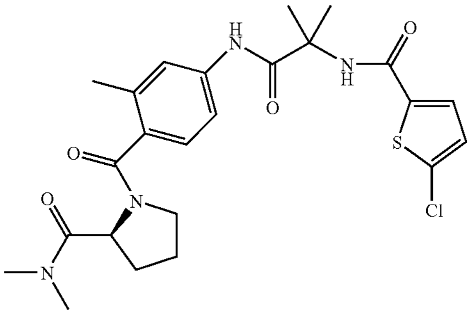 5-chloro-thiophene-2-carboxylic acid-N-{1-methyl-1-[3-methyl-4-((2S)-2-{dimethylaminocarbonyl}-pyrrolidin-1-yl-carbonyl)-phenylcarbamoyl]-ethyl}-amide | $(M + H)^+$ = 506.05 | 3.56 min (HPLC-MS 2) |
| 46 | 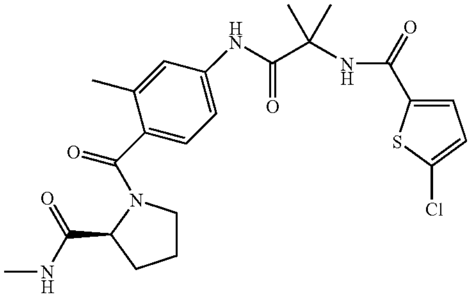 5-chloro-thiophene-2-carboxylic acid-N-{1-methyl-1-[3-methyl-4-((2S)-2-{methylaminocarbonyl}-pyrrolidin-1-yl-carbonyl)-phenylcarbamoyl]-ethyl}-amide | $(M + H)^+$ = 492.02 | 3.46 min (HPLC-MS 2) |

-continued

| No. | Structural formula<br>Name | Mass peak(s) | $R_f$ value or $R_t$ |
|---|---|---|---|
| 47 | 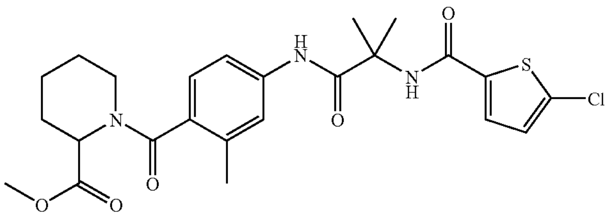<br>5-chloro-thiophene-2-carboxylic acid-N-{1-methyl-1-[3-methyl-4-(2-methoxycarbonyl-piperidun-1-yl-carbonyl)-phenylcarbamoyl]-ethyl}-amide | $(M + H)^+ =$ 507.03 | 4.09 min (HPLC-MS 2) |
| 48 | 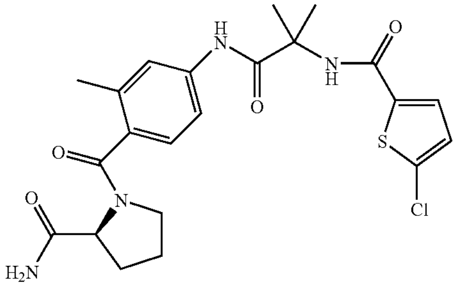<br>5-chloro-thiophene-2-carboxylic acid-N-{1-methyl-1-[3-methyl-4-((2R)-2-aminocarbonyl-pyrrolidin-1-yl-carbonyl)-phenylcarbamoyl]-ethyl}-amide | $(M + H)^+ =$ 477.99 | 3.42 min (HPLC-MS 2) |
| 49 | 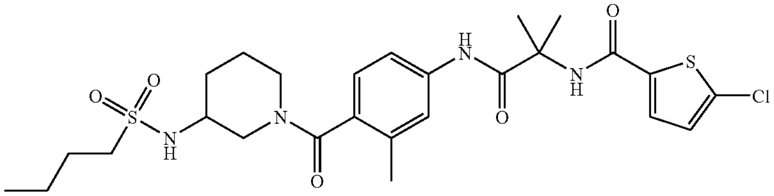<br>5-chloro-thiophene-2-carboxylic acid-N-{1-methyl-1-[3-methyl-4-(3-{1-butyl-sulphonylamino}-piperidin-1-yl-carbonyl)-phenylcarbamoyl]-ethyl}-amide | $(M + H)^+ =$ 584.18 | 3.94 min (HPLC-MS 2) |
| 50 | 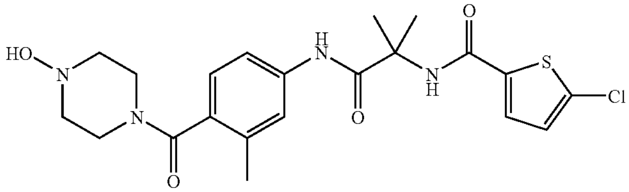<br>5-chloro-thiophene-2-carboxylic acid-N-{1-methyl-1-[3-methyl-4-(4-hydroxy-piperazin-1-yl-carbonyl)-phenylcarbamoyl]-ethyl}-amide | $(M + H)^+ =$ 465.98 | 3.20 min (HPLC-MS 2) |
| 51 | 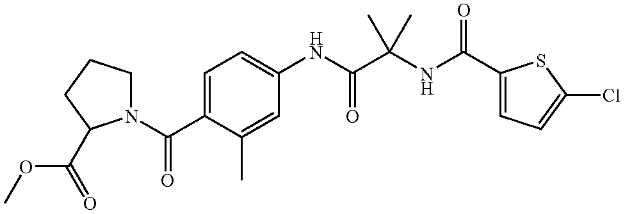<br>5-chloro-thiophene-2-carboxylic acid-N-{1-methyl-1-[3-methyl-4-(2-methoxycarbonyl-pyrrolidin-1-yl-carbonyl)-phenylcarbamoyl]-ethyl}-amide | $(M + H)^+ =$ 493.00 | 3.86 min (HPLC-MS 2) |

-continued

| No. | Structural formula<br>Name | Mass peak(s) | $R_f$-value or $R_t$ |
|---|---|---|---|
| 52 | 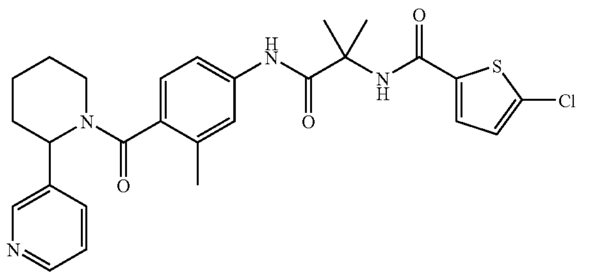<br>5-chloro-thiophene-2-carboxylic acid-N-{1-methyl-1-[3-methyl-4-(2-{pyridin-3-yl}-piperidin-1-yl-carbonyl)-phenylcarbamoyl]-ethyl}-amide | $(M + H)^+$ = 526.08 | 3.35 min (HPLC-MS 2) |
| 53 | 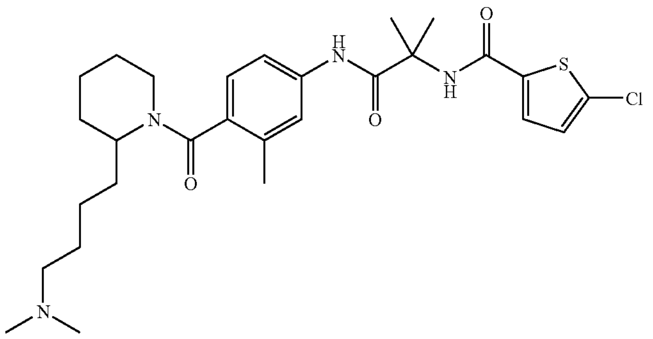<br>5-chloro-thiophene-2-carboxylic acid-N-{1-methyl-1-[3-methyl-4-(2-{4-dimethylamino-but-1-yl}-piperidin-1-yl-carbonyl)-phenylcarbamoyl]-ethyl}-amide | $(M + H)^+$ = 548.17 | 3.44 min (HPLC-MS 2) |
| 54 | 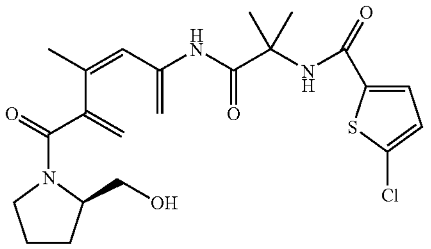<br>5-chloro-thiophene-2-carboxylic acid-N-{1-methyl-1-[3-methyl-4-((2R)-2-hydroxymethyl-pyrrolidin-1-yl-carbonyl)-phenylcarbamoyl]-ethyl}-amide | $(M + H)^+$ = 464.99 | 3.58 min (HPLC-MS 2) |
| 55 | 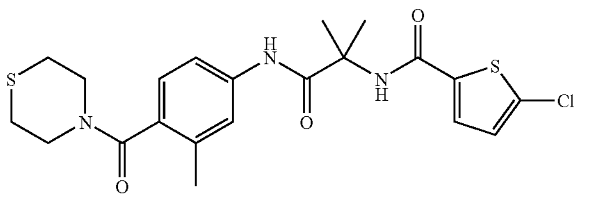<br>5-chloro-thiophene-2-carboxylic acid-N-{1-methyl-1-[3-methyl-4-(thiomorpholin-4-yl-carbonyl)-phenylcarbamoyl]-ethyl}-amide | $(M + H)^+$ = 467.03 | 3.95 min (HPLC-MS 2) |

-continued

| No. | Structural formula<br>Name | Mass peak(s) | $R_f$-value or $R_t$ |
|---|---|---|---|
| 56 | 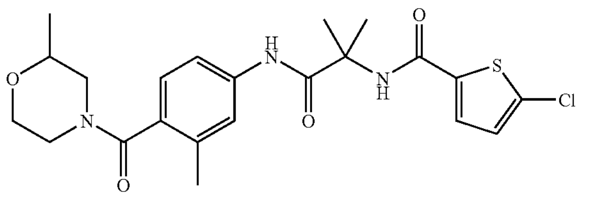<br>5-chloro-thiophene-2-carboxylic acid-N-{1-methyl-1-[3-methyl-4-(2-methyl-morpholin-4-yl-carbonyl)-phenylcarbamoyl]-ethyl}-amide | $(M + H)^+$ = 464.99 | 3.78 min (HPLC-MS 2) |
| 57 | 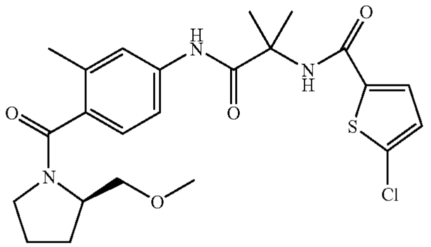<br>5-chloro-thiophene-2-carboxylic acid-N-{1-methyl-1-[3-methyl-4-((2R)-2-methoxymethyl-pyrrolidin-1-yl-carbonyl)-phenylcarbamoyl]-ethyl}-amide | $(M + H)^+$ = 479.02 | 3.89 min (HPLC-MS 2) |
| 58 | 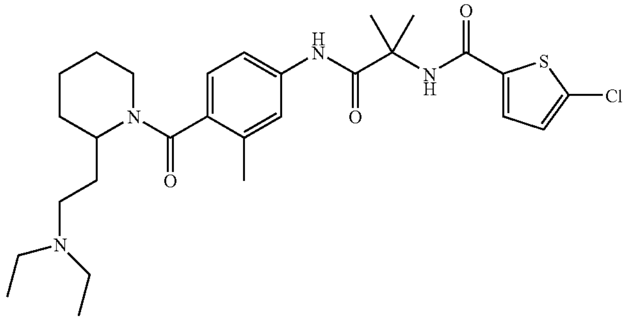<br>5-chloro-thiophene-2-carboxylic acid-N-{1-methyl-1-[3-methyl-4-(2-{2-diethylamino-eth-1-yl)-piperidin-1-yl-carbonyl)-phenylcarbamoyl]-ethyl}-amide, | $(M + H)^+$ = 548.17 | 3.43 min (HPLC-MS 2) |
| 59 | 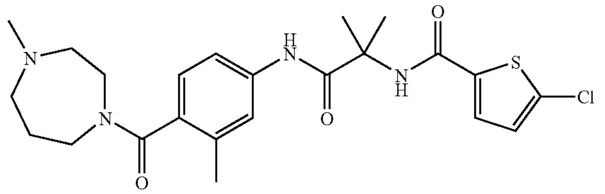<br>5-chloro-thiophene-2-carboxylic acid-N-{1-methyl-1-[3-methyl-4-(4-methyl-[1,4]diazepan-1-yl-carbonyl)-phenylcarbamoyl]-ethyl}-amide | $(M + H)^+$ = 478.04 | 3.14 min (HPLC-MS 2) |
| 60 | 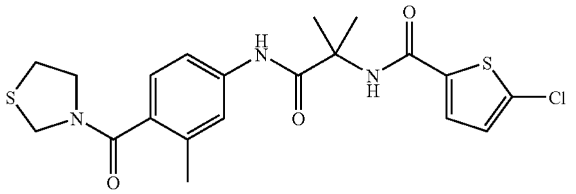<br>5-chloro-thiophene-2-carboxylic acid-N-{1-methyl-1-[3-methyl-4-(thiazolidin-1-yl-carbonyl)-phenylcarbamoyl]-ethyl}-amide | $(M + H)^+$ = 453.01 | 3.90 min (HPLC-MS 2) |

-continued

| No. | Structural formula<br>Name | Mass peak(s) | $R_f$-value or $R_t$ |
|---|---|---|---|
| 61 | 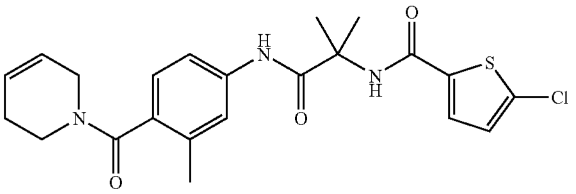<br>5-chloro-thiophene-2-carboxylic acid-N-{1-methyl-1-[3-methyl-4-(3,6-dihydro-2H-pyridin-1-yl-carbonyl)-phenylcarbamoyl]-ethyl}-amide | $(M + H)^+ =$ 446.98 | 3.97 min (HPLC-MS 2) |
| 62 | 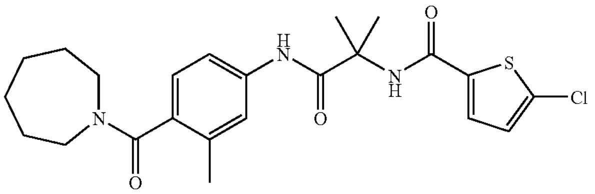<br>5-chloro-thiophene-2-carboxylic acid-N-{1-methyl-1-[3-methyl-4-(azepan-1-yl-carbonyl)-phenylcarbamoyl]-ethyl}-amide | $(M + H)^+ =$ 463.02 | 4.11 min (HPLC-MS 2) |
| 63 | 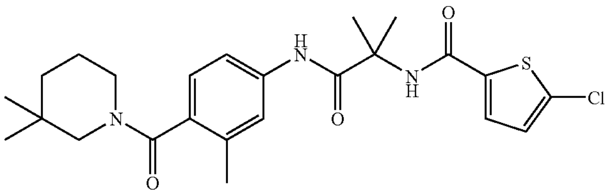<br>5-chloro-thiophene-2-carboxylic acid-N-{1-methyl-1-[3-methyl-4-(3,3-dimethyl-piperidin-1-yl-carbonyl)-phenylcarbamoyl]-ethyl}-amide | $(M + H)^+ =$ 477.05 | 4.29 min (HPLC-MS 2) |
| 64 | 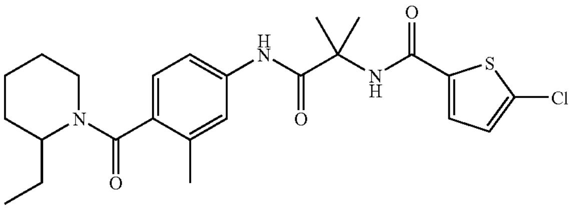<br>5-chloro-thiophene-2-carboxylic acid-N-{1-methyl-1-[3-methyl-4-(2-ethyl-piperidin-1-yl-carbonyl)-phenylcarbamoyl]-ethyl}-amide | $(M + H)^+ =$ 477.05 | 4.27 min (HPLC-MS 2) |
| 65 | 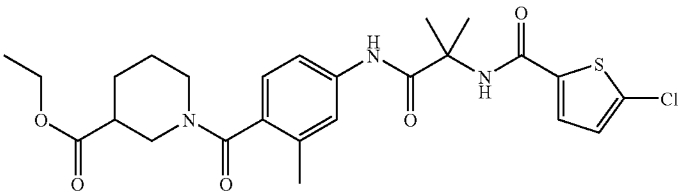<br>5-chloro-thiophene-2-carboxylic acid-N-{1-methyl-1-[3-methyl-4-(2-ethyl-piperidin-1-yl-carbonyl)-phenylcarbamoyl]-ethyl}-amide | $(M + H)^+ =$ 521.06 | 4.07 min (HPLC-MS 2) |

-continued

| No. | Structural formula<br>Name | Mass peak(s) | $R_f$-value or $R_t$ |
|---|---|---|---|
| 66 | 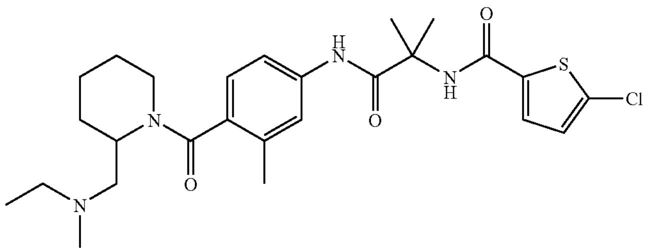<br>5-chloro-thiophene-2-carboxylic acid-N-{1-methyl-1-[3-methyl-4-(3-ethoxycarbonyl-piperidin-1-yl-carbonyl)-phenylcarbamoyl]-ethyl}-amide | $(M + H)^+$ = 520.12 | 3.36 min (HPLC-MS 2) |
| 67 | 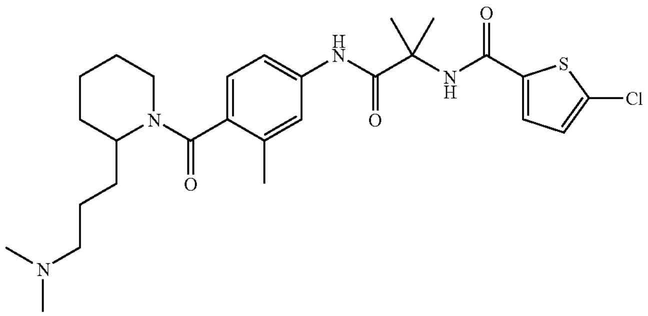<br>5-chloro-thiophene-2-carboxylic acid-N-{1-methyl-1-[3-methyl-4-(2-{3-dimethylamino-prop-1-yl}-piperidin-1-yl-carbonyl)-phenylcarbamoyl]-ethyl} amide | $(M + H)^+$ = 534.14 | 3.38 min (HPLC-MS 2) |
| 68 | 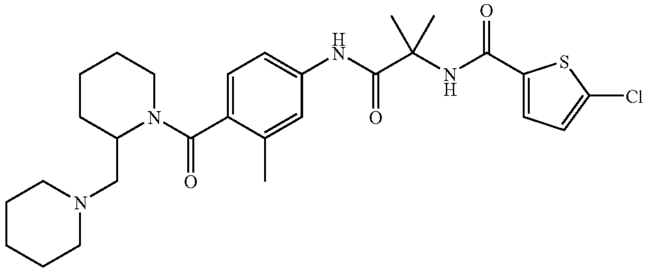<br>5-chloro-thiophene-2-carboxylic acid-N-{1-methyl-1-[3-methyl-4-(2-{piperidin-1-yl-methyl}-piperidin-1-yl-carbonyl)-phenylcarbamoyl]-ethyl}-amide | $(M + H)^+$ = 546.15 | 3.42 min (HPLC-MS 2) |
| 69 | 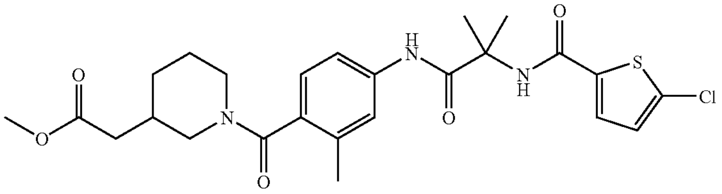<br>5-chloro-thiophene-2-carboxylic acid-N-{1-methyl-1-[3-methyl-4-(2-{methoxy-carbonyl-methyl}-piperidin-1-yl-carbonyl)-phenylcarbamoyl]-ethyl}-amide | $(M + H)^+$ = 521.06 | 3.97 min (HPLC-MS 2) |

-continued

| No. | Structural formula<br>Name | Mass peak(s) | $R_f$ value or $R_t$ |
|---|---|---|---|
| 70 | 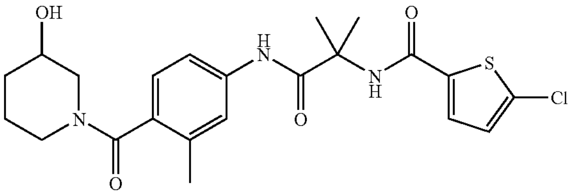<br>5-chloro-thiophene-2-carboxylic acid-N-{1-methyl-1-[3-methyl-4-(3-hydroxyl-piperidin-1-yl-carbonyl)-phenylcarbamoyl]-ethyl}-amide | $(M + H)^+$ = 464.99 | 3.52 min (HPLC-MS 2) |
| 71 | 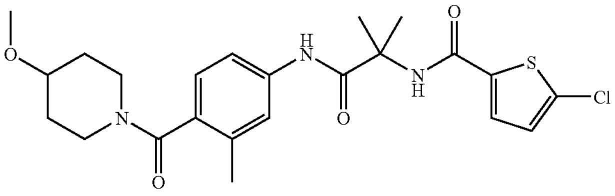<br>5-chloro-thiophene-2-carboxylic acid-N-{1-methyl-1-[3-methyl-4-(4-methoxy-piperidin-1-yl-carbonyl)-phenylcarbamoyl]-ethyl}-amide | $(M + H)^+$ = 479.02 | 3.79 min (HPLC-MS 2) |
| 72 | 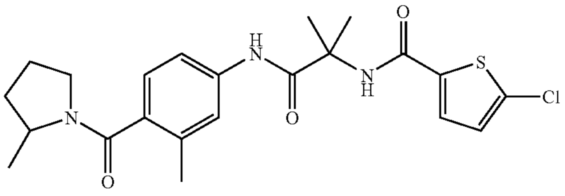<br>5-chloro-thiophene-2-carboxylic acid-N-{1-methyl-1-[3-methyl-4-(2-methyl-pyrrolidin-1-yl-carbonyl)-phenylcarbamoyl]-ethyl}-amide | $(M + H)^+$ = 448.99 | 3.94 min (HPLC-MS 2) |
| 73 | 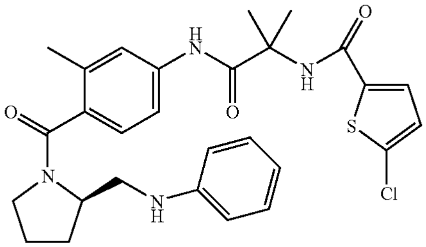<br>5-chloro-thiophene-2-carboxylic acid-N-{1-methyl-1-[3-methyl-4-((2R)-2-{phenylamino-methyl}-pyrrolidin-1-yl-carbonyl)-phenylcarbamoyl]-ethyl}-amide | $(M + H)^+$ = 540.11 | 3.82 min (HPLC-MS 2) |
| 74 | 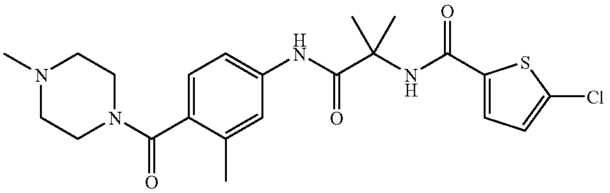<br>5-chloro-thiophene-2-carboxylic acid-N-{1-methyl-1-[3-methyl-4-(4-methyl-piperazin-1-yl-carbonyl)-phenylcarbamoyl]-ethyl}-amide | $(M + H)^+$ = 464.01 | 3.12 min (HPLC-MS 2) |

-continued

| No. | Structural formula<br>Name | Mass peak(s) | $R_f$-value or $R_t$ |
|---|---|---|---|
| 75 | 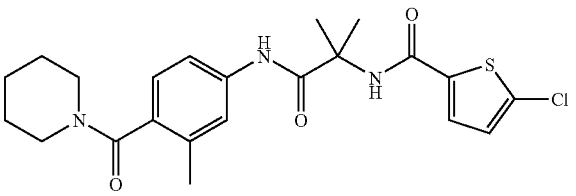<br>5-chloro-thiophene-2-carboxylic acid-N-{1-methyl-1-[3-methyl-4-(piperidin-1-yl-carbonyl)-phenylcarbamoyl]-ethyl}-amide | $(M + H)^+ =$ 448.99 | 4.01 min (HPLC-MS 2) |
| 76 | 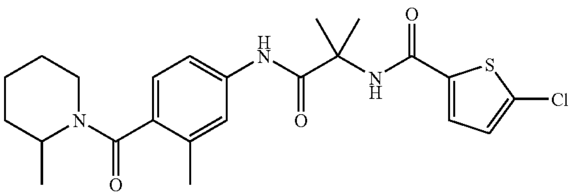<br>5-chloro-thiophene-2-carboxylic acid-N-{1-methyl-1-[3-methyl-4-(2-methyl-piperidin-1-yl-carbonyl)-phenylcarbamoyl]-ethyl}-amide | $(M + H)^+ =$ 463.02 | 4.13 min (HPLC-MS 2) |
| 77 | 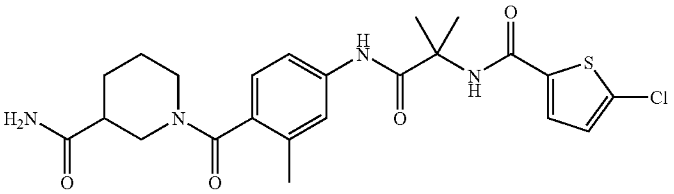<br>5-chloro-thiophene-2-carboxylic acid-N-{1-methyl-1-[3-methyl-4-(3-aminocarbonyl-piperidin-1-yl-carbonyl)-phenylcarbamoyl]-ethyl}-amide | $(M + H)^+ =$ 492.02 | 3.44 min (HPLC-MS 2) |
| 78 | 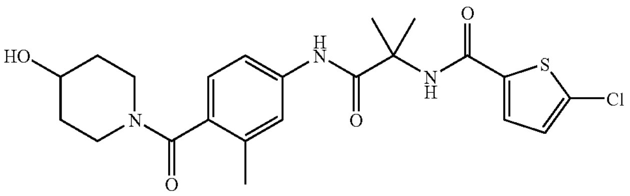<br>5-chloro-thiophene-2-carboxylic acid-N-{1-methyl-1-[3-methyl-4-(4-hydroxyl-piperidin-1-yl-carbonyl)-phenylcarbamoyl]-ethyl}-amide | $(M + H)^+ =$ 464.99 | 3.43 min (HPLC-MS 2) |
| 79 | 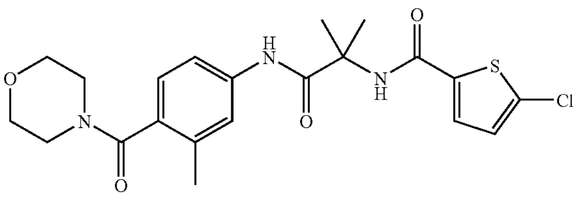<br>5-chloro-thiophene-2-carboxylic acid-N-{1-methyl-1-[3-methyl-4-(morpholin-4-yl-carbonyl)-phenylcarbamoyl]-ethyl}-amide | $(M + H)^+ =$ 450.97 | 3.64 min (HPLC-MS 2) |

-continued

| No. | Structural formula<br>Name | Mass peak(s) | $R_f$-value or $R_t$ |
|---|---|---|---|
| 80 | 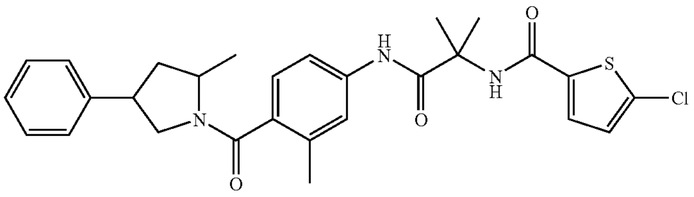<br>5-chloro-thiophene-2-carboxyiic acid-N-{1-methyl-1-[3-methyl-4-(2-methyl-4-phenyl-pyrrolidin-1-yl-carbonyl)-phenylcarbamoyl]-ethyl}-amide | $(M + H)^+$ = 525.09 | 4.41 min (HPLC-MS 2) |
| 81 | 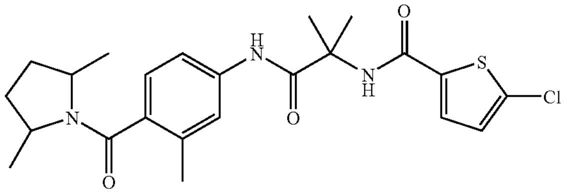<br>5-chloro-thiophene-2-carboxylic acid-N-{1-methyl-1-[3-methyl-4-(2,5-dimethyl-pyrrolidin-1-yl-carbonyl)-phenylcarbamoyl]-ethyl}-amide | $(M + H)^+$ = 463.02 | 4.09 min (HPLC-MS 2) |
| 82 | 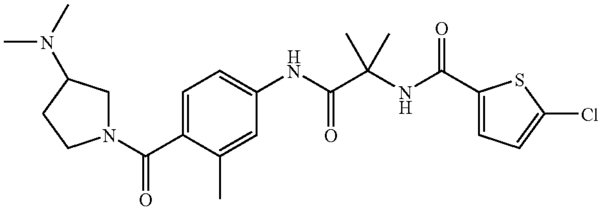<br>5-chloro-thiophene-2-carboxylic acid-N-{1-methyl-1-[3-methyl-4-(3-dimethylamino-pyrrolidin-1-yl-carbonyl)-phenylcarbamoyl]-ethyl}-amide | $(M + H)^+$ = 478.04 | 3.12 min (HPLC-MS 2) |
| 83 | 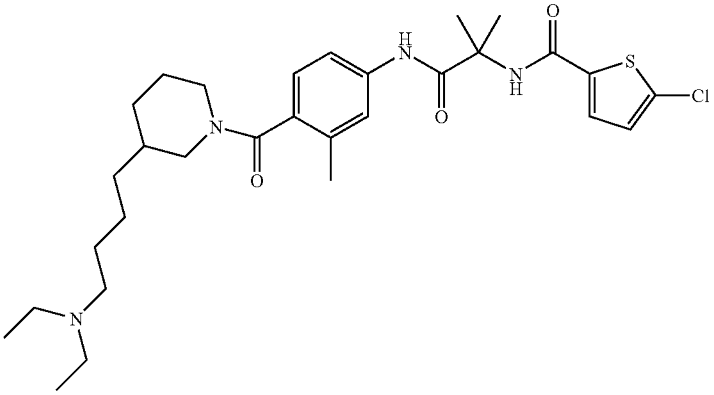<br>5-chloro-thiophene-2-carboxylic acid-N-{1-methyl-1-[3-methyl-4-(3-{4-diethylamino-but-1-yl}-piperidin-1-yl-carbonyl)-phenylcarbamoyl]-ethyl}-amide | $(M + H)^+$ = 576.22 | 3.50 min (HPLC-MS 2) |
| 84 | 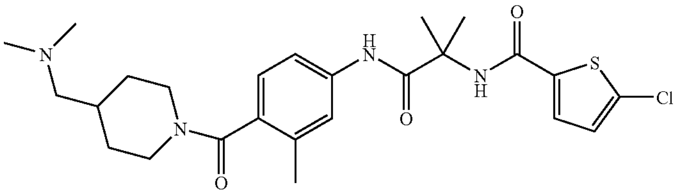<br>5-chloro-thiophene-2-carboxylic acid-N-{1-methyl-1-[3-methyl-4-(4-{dimethylamino-methyl}-piperidin-1-yl-carbonyl)-phenylcarbamoyl]-ethyl}-amide | $(M + H)^+$ = 506.09 | 3.16 min (HPLC-MS 2) |

-continued

| No. | Structural formula<br>Name | Mass peak(s) | $R_f$-value or $R_t$ |
|---|---|---|---|
| 85 | 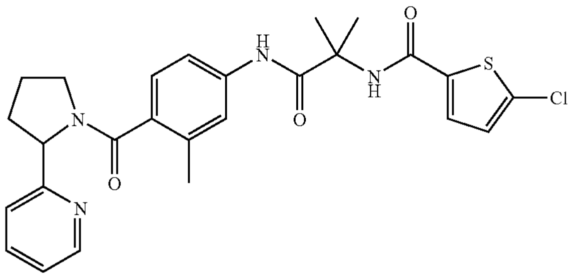<br>5-chloro-thiophene-2-carboxylic acid-N-{1-methyl-1-[3-methyl-4-(2-{pyridin-2-yl)-pyrrolidin-1-yl-carbonyl)-phenylcarbamoyl]-ethyl}-amide | $(M + H)^+ =$ 512.05 | 3.30 min (HPLC-MS 2) |
| 86 | 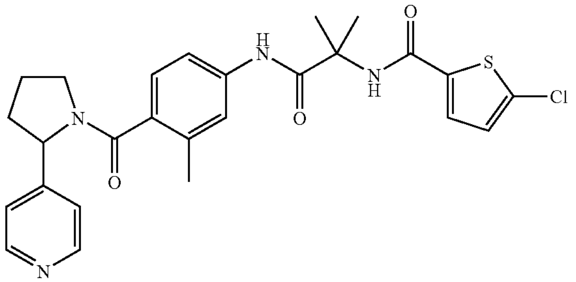<br>5-chloro-thiophene-2-carboxylic acid-N-{1-methyl-1-[3-methyl-4-(2-{pyridin-4-yl}-pyrrolidin-1-yl-carbonyl)-phenylcarbamoyl]-ethyl}-amide | $(M + H)^+ =$ 512.05 | 3.26 min (HPLC-MS 2) |
| 87 | 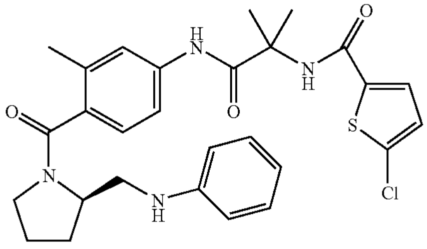<br>5-chloro-thiophene-2-carboxylic acid-N-{1-methyl-1-[3-methyl-4-((2S)-2-{phenylamino-methyl}-pyrrolidin-1-yl-carbonyl)-phenylcarbamoyl]-ethyl}-amide | $(M + H)^+ =$ 540.11 | 3.82 min (HPLC-MS 2) |

Example 88

5-chloro-thiophene-2-carboxylic acid-N-{1-[3-methyl-4-(4-ethyl-piperazin-1-yl-carbonyl)-phenylcarbamoyl]-ethyl}-amide

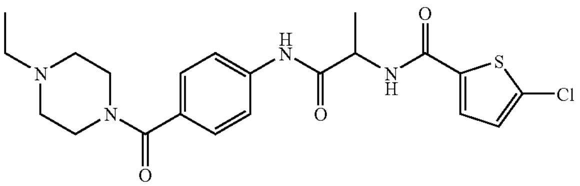

200 μl of a 0.05-molar solution of 2-[(5-chloro-thiophene-2-carbonyl)-amino]-propionic acid, which additionally contains 0.05 mol/l DIPEA, in DMF are combined with 100 μl of a 0.1-molar solution of HATU in DMF on a microtitre plate and mixed for 10 min on a shaker. Then 200 μl of a 0.05-molar solution of 4-(4-ethyl-piperazin-1-yl-carbonyl)-aniline which additionally contains 0.05 mol/l DIPEA are pipetted in and the mixture is again combined by jogging. After 16 h at 80° C. the mixture is filtered through basic aluminium oxide and washed again with DMF/methanol=9:1. Then it is evaporated down i. vac.

$R_t$ value: 3.10 min (HPLC-MS 2)

$C_{21}H_{25}ClN_4O_3S$ (448.98)

Mass spectrum: $(M+H)^+=449$

The Examples that follow describe the preparation of pharmaceutical formulations which contain as active substance any desired compound of general formula I:

Example I

Dry Ampoule Containing 75 mg of Active Substance Per 10 ml

Composition:

| | |
|---|---|
| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use for injections, the product is dissolved in water.

Example II

Dry Ampoule Containing 35 mg of Active Substance Per 2 ml

Composition:

| | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use for injections, the product is dissolved in water.

Example III

Tablet Containing 50 mg of Active Substance

Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

Example IV

Tablet Containing 350 mg of Active Substance

Composition:

| | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

Example V

Capsules Containing 50 mg of Active Substance

Composition:

| | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatine capsules in a capsule filling machine.

Example VI

Capsules Containing 350 mg of Active Substance

Composition:

| | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatine capsules in a capsule filling machine.

Example VII

Suppositories Containing 100 mg of Active Substance

1 Suppository Contains:

| | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylenesorbitan monostearate. At 40° C. the ground active substance is homogeneously dispersed in the melt. It is cooled to 38° C. and poured into slightly chilled suppository moulds.

What is claimed is:

1. A compound of the formula (I)

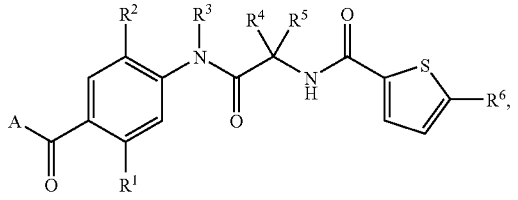

wherein

A denotes a 5- to 7-membered cycloalkyleneimino group wherein a methylene group in the 3 position of a 5-membered cycloalkyleneimino group may be replaced by a sulphur atom, or a methylene group in the 4 position of a 6- or 7-membered cycloalkyleneimino group may be replaced by an oxygen or sulphur atom, a sulphinyl or a —$NR^{8c}$— group and additionally a methylene group adjacent to an above-mentioned —$NR^{8c}$— group may be replaced by a carbonyl group, a methylene group of the cycloalkyleneimino group may be substituted by one or two $C_{1-4}$-alkyl groups optionally substituted by a group $R^{7a}$, $R^{7b}$ or $R^{7c}$, or by groups $R^{7b}$ or $R^{7c}$, and/or one or two methylene groups of the cycloalkyleneimino moiety not adjacent to the imino group may be substituted by a group $R^{7a}$, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a $C_{1-3}$-alkyl group, $R^3$ denotes a hydrogen atom or a $C_{1-3}$-alkyl group, $R^4$ and $R^5$ in each case independently of one another denote a hydrogen atom, a straight-chain or branched $C_{1-6}$-alkyl group, while the hydrogen atoms of the straight-chain or branched $C_{1-6}$-alkyl group may optionally be substituted by a $C_{1-4}$-alkyloxy, hydroxy, pyridine, or an imidazole group, a phenyl, pyridinyl or imidazolyl, or $R^4$ and $R^5$ together with the carbon atom to which they are bound form a cyclobutyl, tetrahydrofuranyl, or $C_{3-8}$-cycloalkyl group, $R^6$ denotes a hydrogen, fluorine, chlorine, bromine or iodine atom, a nitrile group, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms, $R^{7a}$ in each case independently of one another denotes a hydroxy, $C_{1-4}$-alkoxy, while the hydrogen atoms of the $C_{1-4}$-alkoxy group may optionally be wholly or partly replaced by allyloxy, benzyloxy, $C_{1-4}$-alkylcarbonyloxy, $C_{1-4}$-alkyloxycarbonyloxy, amino, $C_{1-3}$-alkylamino, arylamino, heteroarylamino, di-($C_{1-3}$-alkyl)-amino, piperidin-4-yl, N—$C_{1-3}$-alkyl-piperidin-4-yl, N—$C_{1-3}$-alkylcarbonyl-piperidin-4-yl, $C_{1-5}$-alkylcarbonylamino, $C_{1-5}$-alkylsulphonylamino, N—($C_{1-5}$-alkylsulphonyl)-$C_{1-5}$-alkylamino, $C_{1-5}$-alkoxycarbonylamino, aminocarbonylamino, $C_{1-4}$-alkylaminocarbonylamino or a di-($C_{1-3}$-alkyl)-aminocarbonylamino group, phenyl, pyridinyl, pyrrolidinyl, $R^{7b}$ in each case independently of one another denotes a carboxy, $C_{1-3}$-alkoxycarbonyl, aminocarbonyl, $C_{1-3}$-alkylaminocarbonyl, di-($C_{1-3}$-alkyl)-aminocarbonyl, nitrile, aminosulphonyl, $C_{1-4}$-alkylaminosulphonyl, or di-($C_{1-4}$-alkyl)-aminosulphonyl group, $R^{7c}$ in each case independently of one another denotes an aryl or heteroaryl group, $R^{8a}$ in each case independently of one another denotes a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, $C_{3-6}$-cycloalkyleneimino, carboxy, nitrile, $C_{1-3}$-alkoxycarbonyl, aminocarbonyl, $C_{1-3}$-alkylaminocarbonyl or a di-($C_{1-3}$-alkyl)-aminocarbonyl group, $R^{8b}$ in each case independently of one another denotes a hydrogen atom or a $C_{1-5}$-alkyl group, $R^{8c}$ in each case independently of one another denotes a hydrogen atom, a hydroxyl, $C_{1-5}$-alkyl, $C_{1-5}$-alkoxy, formyl, $C_{1-5}$-alkylcarbonyl, $C_{1-5}$-alkyloxycarbonyl or $C_{1-5}$-alkylsulphonyl, aryl or heteroaryl group, which may optionally be substituted by one or two fluorine, chlorine or bromine atom or a group $R^{8a}$, and moreover a phenyl ring optionally substituted by a fluorine, chlorine or bromine atom or a group $R^{8a}$ may be fused to the above-mentioned monocyclic aryl groups via two adjacent carbon atoms, while, unless otherwise stated, by the term “heteroaryl group” mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkyl-amino-$C_{2-3}$- alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an optionally by a $C_{1-3}$-alkyl or phenyl-$C_{1-3}$-alkyl group substituted imino group and two or three nitrogen atoms, and the above-mentioned monocyclic heteroaryl groups may be substituted in the carbon skeleton by one or two groups $R^{8a}$, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the previously mentioned definitions, which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, or a tautomer or salt thereof.

2. A compound of the formula I according to claim 1, wherein:

A denotes a 5- to 7-membered cycloalkyleneimino group, wherein a methylene group in the 3 position of a 5-membered cycloalkyleneimino group may be replaced by a sulphur atom, or a methylene group in the 4 position of a 6- or 7-membered cycloalkyleneimino group may be replaced by an oxygen or sulphur atom or a —$NR^{8c}$— group and additionally a methylene group adjacent to an above-mentioned —$NR^{8c}$— group may be replaced by a carbonyl group, a methylene group of the cycloalkyleneimino group may be substituted by one or two $C_{1-4}$-alkyl groups optionally substituted by a group $R^{7a}$, $R^{7b}$ or $R^{7c}$, or by groups $R^{7b}$ or $R^{7c}$, and/or one or two methylene groups of the cycloalkyleneimino moiety not adjacent to the imino group may be substituted by a group $R^{7a}$, $R^1$ denotes a hydrogen, fluorine, chlorine, bromine atom or a methyl or methoxy group, while the hydrogen atoms of the methyl or methoxy group may optionally be wholly or partly replaced by fluorine atoms, $R^2$ denotes a hydrogen or fluorine atom, $R^3$ denotes a hydrogen atom, $R^4$ denotes a straight-chain or branched $C_{1-3}$-alkyl group which may optionally be substituted by a $C_{1-2}$-alkyloxy group, hydroxy, pyridine or an imidazole group, $R^5$ denotes a hydrogen atom, or a methyl group, or $R^4$ and $R^5$ together with the carbon atom to which they are bound form a cyclobutyl, tetrahydrofuranyl, or $C_{3-6}$-cycloalkyl group, $R^6$ denotes a chlorine or bromine atom, $R^{7a}$ in each case independently of one another denotes a hydroxy, $C_{1-4}$-alkoxy, $C_{1-4}$-alkylcarbonyloxy, amino, $C_{1-3}$-alkylamino, phenylamino, di-($C_{1-3}$-alkyl)-amino, piperidin-4-yl, N—$C_{1-3}$-alkyl-piperidin-4-yl, N—$C_{1-3}$-alkylcarbonyl-piperidin-4-yl, $C_{1-5}$-alkylcarbonylamino, $C_{1-4}$-alkylaminocarbonylamino, $C_{1-5}$-alkylsulphonylamino, N—($C_{1-5}$-alkylsulphonyl)-$C_{1-5}$-alkylamino or $C_{1-5}$-alkoxycarbonylamino group, $R^{7b}$ in each case independently of one another denotes a $C_{1-3}$-alkoxycarbonyl, aminocarbonyl, $C_{1-3}$-alkylaminocarbonyl, di-($C_{1-3}$-alkyl)-aminocarbonyl, aminosulphonyl, $C_{1-4}$-alkylaminosulphonyl or di-($C_{1-4}$-alkyl)-aminosulphonyl group, $R^{7c}$ in each case independently of one another denotes an aryl or heteroaryl group, $R^{7d}$ in each case independently of one another denotes a hydroxy, $C_{1-4}$-alkoxy, while the hydrogen atoms of the $C_{1-4}$-alkoxy group may optionally be wholly or partly replaced by fluorine atoms, $C_{1-4}$-alkylcarbonyloxy, $C_{1-3}$-alkylamino, di-($C_{1-3}$-alkyl)-amino, $C_{1-5}$-alkylcarbonylamino or $C_{1-5}$-alkoxycarbonylamino group, $R^{7e}$ in each case independently of one another denotes a $C_{1-3}$-alkoxycarbonyl, aminocarbonyl, $C_{1-3}$-alkylaminocarbonyl, di-($C_{1-3}$-alkyl)-aminocarbonyl, nitrile, aminosulphonyl, $C_{1-4}$-alkylaminosulphonyl or di-($C_{1-4}$-alkyl)-aminosulphonyl group, $R^{8a}$ in each case independently of one another denotes a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, nitrile, $C_{1-3}$-alkylaminocarbonyl or a di-($C_{1-3}$-alkyl)-aminocarbonyl group, $R^{8c}$ in each case independently of one another denotes a hydrogen atom, a $C_{1-3}$-alkyl, $C_{1-3}$-alkoxy, formyl, $C_{1-3}$-alkylcarbonyl or $C_{1-4}$-alkyloxycarbonyl group, while, unless otherwise stated, by the term "aryl group" mentioned hereinbefore in the definitions is meant a phenyl group, which may optionally be substituted by one or two fluorine, chlorine or bromine atoms or a group $R^{8a}$, while the "heteroaryl group" mentioned in the definitions given hereinbefore is selected from the group consisting of imidazolyl, furanyl, oxazolyl, tetrazolyl, pyridinyl, pyrimidinyl and pyrazinyl, while one or two carbon atoms or the NH group contained in 5-membered heteroaryl groups may be substituted by a group $R^{8b}$, while, unless otherwise stated, by the term "halogen atom" mentioned hereinbefore in the definitions is meant an atom selected from among fluorine, chlorine, bromine and iodine, while the alkyl and alkoxy groups contained in the definitions given hereinbefore which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, or a tautomer or salt thereof.

3. A compound of the formula I according to claim 1, wherein:

A denotes a 5- to 7-membered cycloalkyleneimino group, wherein a methylene group in the 3 position of a 5-membered cycloalkyleneimino group may be replaced by a sulphur atom, or a methylene group in the 4 position of a 6- or 7-membered cycloalkyleneimino group may be replaced by an oxygen or sulphur atom or a —$NR^{8c}$— group and additionally a methylene group adjacent to an above-mentioned —$NR^{8c}$— group may be replaced by a carbonyl group, a methylene group of the cycloalkyleneimino group may be substituted by one or two $C_{1-4}$-alkyl groups optionally substituted by a group $R^{7a}$, $R^{7b}$ or $R^{7c}$, or by groups $R^{7b}$ or $R^{7c}$, and/or one or two methylene groups of the cycloalkyleneimino moiety not adjacent to the imino group may be substituted by a group $R^{7a}$, $R^1$ denotes a hydrogen, chlorine or bromine atom or a methyl group, $R^2$ denotes a hydrogen or fluorine atom, $R^3$ denotes a hydrogen atom, $R^4$ denotes a straight-chain or branched $C_{1-3}$-alkyl group which may optionally be substituted by hydroxy, pyridine, or an imidazole group, $R^5$ denotes a hydrogen atom, or a methyl group, or $R^4$ and $R^5$ together with the carbon atom to which they are bound form a $C_{3-6}$-cycloalkyl group, cyclobutyl or tetrahydrofuranyl group, $R^6$ denotes a chlorine or bromine atom, $R^{7a}$ in each case independently of one another denotes a hydroxy, $C_{1-4}$-alkoxy, amino, $C_{1-3}$-alkylamino, phenylamino, di-($C_{1-3}$-alkyl)-amino, $C_{1-5}$-alkylsulphonylamino, or $C_{1-4}$-alkylaminocarbonylamino group, $R^{7b}$ in each case independently of one another denotes a $C_{1-3}$-alkoxycarbonyl, aminocarbonyl, $C_{1-3}$-alkylaminocarbonyl or di-($C_{1-3}$-alkyl)-aminocarbonyl group, $R^{7c}$ in each case independently of one another denotes an aryl or heteroaryl group, $R^{7d}$ in each case independently of one another denotes a hydroxy or $C_{1-3}$-alkoxy group, $R^{8c}$ in each case independently of one another denotes a hydrogen atom, a $C_{1-3}$-alkyl, formyl, or $C_{1-3}$-alkylcarbonyl group, while the "heteroaryl group" mentioned in the definitions given hereinbefore is selected from the group consisting of imidazolyl and pyridinyl, while, unless otherwise stated, by the term "halogen atom" mentioned hereinbefore in the definitions is meant an atom selected from among fluorine, chlorine, bromine and iodine, while the alkyl and alkoxy groups contained in the definitions given hereinbefore which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, or a tautomer or salt thereof.

4. A compound of the formula I according to claim 1, wherein $R^4$ and $R^5$ do not denote hydrogen.

5. A compound of the formula I according to claim 1, wherein $R^4$ and $R^5$ together with the carbon atom to which they are bound form a cyclic group.

6. A compound of the formula I according to claim 1, wherein $R^4$ and $R^5$ together with the carbon atom to which they are bound form a cyclic group, while in the cyclic group or the corresponding bridged bicyclic group or the spirocyclic group a methylene group is replaced by an oxygen atom or a $N(R^{8c})$ group according to the specified method.

7. A compound of the formula I according to claim 1, wherein $R^4$ and $R^5$ together with the carbon atom to which they are bound denote a cyclic group of the formula

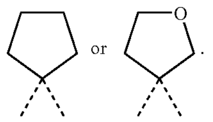

8. A compound of the formula I according to claim 1, wherein:

A denotes a 5- to 7-membered cycloalkyleneimino group, where a methylene group of the cycloalkyleneimino moiety may be substituted by a $C_{1-3}$-alkyl or pyridyl group optionally substituted by a hydroxy, $C_{1-3}$-alkoxy, di-($C_{1-3}$-alkyl)-amino, a 5- to 6-membered cycloalkyleneimino, $C_{1-3}$-alkylcarbonylamino or $C_{1-3}$-alkylsulphonylamino group.

9. A compound of the formula I according to claim 1, wherein:

A denotes a 5- to 7-membered cycloalkyleneimino group, while a methylene group in the 4 position of a 6- or 7-membered cycloalkyleneimino group may be replaced by an oxygen atom or by a —$NR^{8c}$— group and additionally a methylene group adjacent to an above-mentioned —$NR^{8c}$— group may be replaced by a carbonyl group.

10. A compound of the formula I according to claim 1, wherein $R^6$ denotes a bromine atom.

11. A compound of the formula I according to claim 1, wherein $R^6$ denotes a chlorine atom.

12. A physiologically acceptable salt of a compound according to any one of claims 1 to 11.

13. A pharmaceutical composition containing a compound according to claim 1 or a physiologically acceptable salt thereof together with one or more inert carriers and/or diluents.

14. A compound of the formula I according to claim 1, wherein the 5- to 7-membered cycloalkyleneimino group is selected from the group consisting of pyrrolidine, morpholine, thiomorpholine, piperidine, piperazine, diazepane, azepane and thiazole.

* * * * *